US011844613B2

(12) United States Patent
Arai et al.

(10) Patent No.: US 11,844,613 B2
(45) **Date of Patent: *Dec. 19, 2023**

(54) FATIGUE STATE DETERMINATION DEVICE AND FATIGUE STATE DETERMINATION METHOD

(71) Applicants: DAIKIN INDUSTRIES, LTD., Osaka (JP); TOKYO INSTITUTE OF TECHNOLOGY, Tokyo (JP)

(72) Inventors: Junichiro Arai, Osaka (JP); Yasunori Kotani, Tokyo (JP); Taro Tomatsu, Tokyo (JP); Yoshimi Ohgami, Tokyo (JP)

(73) Assignees: Daikin Industries, Ltd., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 1098 days.

This patent is subject to a terminal disclaimer.

(21) Appl. No.: 16/080,516

(22) PCT Filed: Feb. 28, 2017

(86) PCT No.: PCT/JP2017/007989
§ 371 (c)(1),
(2) Date: Aug. 28, 2018

(87) PCT Pub. No.: WO2017/150575
PCT Pub. Date: Sep. 8, 2017

(65) Prior Publication Data

US 2019/0059799 A1 Feb. 28, 2019

(30) Foreign Application Priority Data

Feb. 29, 2016 (JP) ................................ 2016-038479

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0006* (2013.01); *A61B 5/0008* (2013.01);
(Continued)

(58) Field of Classification Search
CPC ......... A61B 5/02; A61B 5/026; A61B 5/0261; A61B 5/16; A61B 5/165
See application file for complete search history.

(56) References Cited

U.S. PATENT DOCUMENTS

| | | | | |
|---|---|---|---|---|
| 6,092,058 | A | 7/2000 | Smyth | |
| 2004/0210159 | A1* | 10/2004 | Kibar .................. | A61B 5/4803 600/558 |

(Continued)

FOREIGN PATENT DOCUMENTS

| | | | |
|---|---|---|---|
| CN | 106793958 | A | 5/2017 |
| CN | 108135498 | A | 6/2018 |

(Continued)

OTHER PUBLICATIONS

International Preliminary Report of corresponding PCT Application No. PCT/JP2017/007989 dated Sep. 13, 2018.

(Continued)

*Primary Examiner* — Christopher A Flory
(74) *Attorney, Agent, or Firm* — Global IP Counselors, LLP

(57) ABSTRACT

A fatigue state determination device and a fatigue state determination method determine a fatigue state of a subject. The fatigue state determination device includes a brain-function activation information provision unit and a fatigue state determination unit. The brain-function activation infor-
(Continued)

mation provision unit provides brain-function activation information in order to activate a human brain function of a subject. The fatigue state determination unit determines a fatigue state of the subject based on facial-surface change information indicative of a time-series change of facial surface data on the subject while the brain-function activation information is being provided.

14 Claims, 30 Drawing Sheets

(51) Int. Cl.
*A61B 5/026* (2006.01)
*A61B 5/01* (2006.01)

(52) U.S. Cl.
CPC .......... *A61B 5/0013* (2013.01); *A61B 5/0075* (2013.01); *A61B 5/0077* (2013.01); *A61B 5/01* (2013.01); *A61B 5/015* (2013.01); *A61B 5/0261* (2013.01); *A61B 5/16* (2013.01); *A61B 5/162* (2013.01); *A61B 5/168* (2013.01); *A61B 5/4809* (2013.01); *A61B 5/7264* (2013.01)

(56) References Cited

U.S. PATENT DOCUMENTS

| | | | | |
|---|---|---|---|---|
| 2009/0080730 | A1* | 3/2009 | Pavlidis | G06K 9/00268 382/128 |
| 2011/0251493 | A1* | 10/2011 | Poh | G06K 9/624 600/477 |
| 2014/0107439 | A1* | 4/2014 | Atsumori | A61B 5/165 600/322 |
| 2014/0200416 | A1* | 7/2014 | Kashef | G16H 40/67 600/301 |
| 2014/0375785 | A1 | 12/2014 | Kogut et al. | |
| 2015/0164418 | A1* | 6/2015 | Johnson | A61B 5/4884 434/236 |
| 2015/0282724 | A1* | 10/2015 | McDuff | A61B 5/02427 600/479 |
| 2016/0098592 | A1* | 4/2016 | Lee | G06K 9/00315 434/236 |
| 2017/0281070 | A1 | 10/2017 | Arai et al. | |
| 2017/0347967 | A1* | 12/2017 | Guazzi | A61B 5/0077 |
| 2018/0289266 | A1 | 10/2018 | Arai et al. | |

FOREIGN PATENT DOCUMENTS

| | | | |
|---|---|---|---|
| EP | 2 371 286 | A1 | 10/2010 |
| JP | 9-28679 | A | 2/1997 |
| JP | 2007-233479 | A | 9/2007 |
| JP | 2013-176406 | A | 9/2013 |
| WO | 2014/204567 | A1 | 12/2014 |
| WO | 2015175435 | A1 | 11/2015 |
| WO | 2017/065315 | A1 | 4/2017 |

OTHER PUBLICATIONS

European Search Report of corresponding EP Application No. 17 760 039.2 dated Sep. 18, 2019.

International Search Report of corresponding PCT Application No. PCT/JP2017/007989 dated May 23, 2017.

* cited by examiner

FATIGUE STATE DETERMINATION DEVICE AND FATIGUE STATE DETERMINATION METHOD

CROSS-REFERENCE TO RELATED APPLICATIONS

This U.S. National stage application claims priority under 35 U.S.C. § 119(a) to Japanese Patent Application No. 2016-038479, filed in Japan on Feb. 29, 2016, the entire contents of which are hereby incorporated herein by reference.

TECHNICAL FIELD

The present invention relates to a fatigue state determination device and a fatigue state determination method.

BACKGROUND ART

In recent years, estimation of human brain activity has been attempted using data detected by electroencephalography (EEG), magnetic resonance imaging (fMRI: functional Magnetic Resonance imaging), and near infrared spectroscopy (NIRS) as disclosed in Japanese Laid-open Patent Publication No. 2013-176406. Furthermore, applications, such as determination of the physical condition and the mental state of a human, have been researched based on the estimated brain activity.

SUMMARY

Technical Problem

However, the electroencephalography and the near infrared spectroscopy require preprocessing, such as forcing a subject to attach electrodes thereon. The magnetic resonance imaging method requires measurement in a predetermined MRI room. In short, these methods have drawbacks of a complicated operation at the preparation stage, and a limited condition for measurement. All of these methods require enormous costs. Consequently, these methods may make it difficult to determine the physical condition and mental state of the subject or the like.

It is an object of the present invention to provide a device and method which can easily determine the physical condition and mental state of a subject. Specifically, it is an object of the present invention to provide a fatigue state determination device and a fatigue state determination method for easily determining a fatigue state of the subject.

A fatigue state determination device according to a first aspect of the present invention includes a brain-function activation information provision unit and a fatigue state determination unit. The brain-function activation information provision unit provides brain-function activation information for activating human brain function to a subject. The fatigue state determination unit determines a fatigue state of the subject based on facial-surface change information indicative of a time-series change of facial surface data on the subject while the brain-function activation information is being provided.

The fatigue state determination device according to the first aspect determines the state of the subject based on the facial-surface change information on the subject while the brain-function activation information is being provided, so that the fatigue state of the subject can be determined with a simple configuration.

A fatigue state determination device according to a second aspect of the present invention is the fatigue state determination device according to the first aspect, wherein the brain-function activation information provision unit provides working memory related information as the brain-function activation information.

The fatigue state determination device according to the second aspect provides the working memory related information as the brain-function activation information, thereby enabling extraction of the determination component related to the brain activity. Consequently, the fatigue of the subject can be easily determined.

Note that the "working memory related information" in the present invention is information on tasks requiring memory ability and judgment ability, and includes mental arithmetic tasks, calculation tasks, memorization tasks, such as an N back task, tasks of making an optimal selection from a plurality of pieces of information, such as pictogram tasks, and attention switching tasks which involves switching problems halfway, by way of example.

A fatigue state determination device according to a third aspect of the present invention is the fatigue state determination device according to the first or second aspect, further including a determination information generating unit that generates determination information from the facial-surface change information.

The fatigue determination device according to the third aspect determines the fatigue state of the subject by generating the determination information for determining the fatigue from the facial-surface change information, thereby making it possible to enhance the determination accuracy of the fatigue state of the subject.

A fatigue state determination device according to a fourth aspect of the present invention is the fatigue state determination device according to the third aspect, further including a facial-surface change information decomposition unit. The facial-surface change information decomposition unit decomposes the facial-surface change information into a plurality of components by singular value decomposition, principal component analysis, or independent component analysis. Further, the determination information generating unit extracts a component related to the brain-function activation information from the plurality of components as a determination component, and generates the determination information from the determination component.

The fatigue state determination device according to the fourth aspect extracts the determination component related to the brain-function activation information, from a plurality of components obtained by conducting the singular value decomposition, the principal component analysis, or the independent component analysis on the facial-surface change information. Thus, the presence or absence of the brain activity of the subject can be easily estimated without using any electrode or the like that requires preprocessing before attachment. Consequently, the fatigue state of the subject can be easily determined based on the determination component corresponding to the brain function of the subject.

A fatigue state determination device according to a fifth aspect of the present invention is any fatigue state determination device according to the fourth aspect, wherein the determination information generating unit extracts the determination component based on a value of a significance level.

The fatigue state determination device according to the fifth aspect extracts the component related to the brain-function activation information based on the value of the significance level, thereby making it possible to enhance the reliability of the determination.

A fatigue state determination device according to a sixth aspect of the present invention is the fatigue state determination device according to any one of the third to fifth aspects, further including a reference information storage unit. The reference information storage unit stores, as reference information in relation to a fatigue state level, an amount of change within a predetermined range from a reference correlation value to a correlation value of the determination information calculated with respect to the brain-function activation information. Furthermore, the fatigue state determination unit calculates a correlation value of the determination information with respect to the brain-function activation information, and determines a fatigue state level of the subject based on the calculated correlation value and the reference information.

The fatigue state determination device according to the sixth aspect can easily determine the fatigue state level using the reference information acquired before the predetermined action.

Note that in the present embodiment, the term “predetermined action” as used herein means at least one or both of a physical activity and an intellectual activity. Examples of the physical activity include various physical labor, such as line work in factories and civil engineering work, and various exercises, such as fitness, running, ball games, mountain climbing, and muscle training. Examples of the intellectual activity include learning, discussion, decision making, situation judgement, management and supervision, and the like.

A fatigue state determination device according to a seventh aspect of the present invention is the fatigue state determination device according to any one of the first to sixth aspects, wherein a facial-surface change information acquisition unit acquires data on a paranasal sinus peripheral region and/or a forehead of the subject as the facial surface data.

In the fatigue state determination device according to the seventh aspect, the facial surface data is the data on the paranasal sinus peripheral region and/or the forehead of the subject, thereby making it possible to extract the determination component related to a brain activity with high accuracy.

A fatigue state determination device according to an eighth aspect of the present invention is the fatigue state determination device according to any one of the first to seventh aspects, wherein a facial-surface change information acquisition unit acquires facial skin temperature data indicative of a facial skin temperature of the subject as the facial surface data.

In the fatigue state determination device according to the eighth aspect, the facial surface data is the facial skin temperature data indicative of the facial skin temperature of the subject. Because of this, the fatigue state of the subject can be determined using an infrared camera or the like.

A fatigue state determination device according to a ninth aspect of the present invention is the fatigue state determination device according to any one of the first to eighth aspects, wherein a facial-surface change information acquisition unit acquires facial blood-circulation-amount data based on RGB data regarding a facial surface of the subject as the facial surface data.

In the fatigue state determination device according to the ninth aspect, the facial surface data is the facial blood-circulation-amount data based on the RGB data regarding the facial surface of the subject. Because of this, the fatigue state of the subject can be determined using a solid-state imaging device or the like.

A fatigue state determination device according to a tenth aspect of the present invention is the fatigue state determination device according to any one of the third to ninth aspects, wherein the fatigue state determination unit calculates a correlation value of the determination component with respect to the brain-function activation information, and determines a fatigue state level of the subject based on the calculated correlation value and the reference information. Here, a determination information provision device on a network includes a reference information storage unit that stores, as reference information in relation to a fatigue state level, an amount of change within a predetermined range, from a reference correlation value of a reference determination component calculated with respect to the brain-function activation information, to a correlation value of the determination component calculated with respect to the brain-function activation information.

The fatigue state determination device according to the tenth aspect can determine the fatigue state level of the subject using the determination information provision device on the network.

A fatigue state determination method according to an eleventh aspect of the present invention includes a brain-function activation information provision step, a facial-surface change information acquisition step, and a fatigue state determination step. The brain-function activation information provision step provides brain-function activation information for activating human brain function to a subject after a predetermined action. The fatigue state determination step determines the fatigue state of the subject based on the facial-surface change information.

In the fatigue state determination method according to the eleventh aspect, the fatigue state of the subject is determined based on facial-surface change information regarding the subject provided with the brain-function activation information after the predetermined action, so that the fatigue state of the subject can be determined with a simple configuration.

A fatigue state determination method according to a twelfth aspect of the present invention is the fatigue state determination method according to the eleventh aspect, further including a determination information generating step of generating determination information from the facial-surface change information.

In the fatigue determination method according to the twelfth aspect, the fatigue state of the subject is determined by generating the determination information usable for determining the fatigue from the facial-surface change information, thereby making it possible to enhance the determination accuracy of the fatigue state of the subject.

A fatigue state determination method according to a thirteenth aspect of the present invention is the fatigue state determination method according to the twelfth aspect, further including a facial-surface change information decomposition step. In the facial-surface change information decomposition step, the facial-surface change information is decomposed into a plurality of components by singular value decomposition, principal component analysis, or independent component analysis. Furthermore, in the determination information generating step, a component related to the brain-function activation information is extracted as a determination component from the plurality of components, and the determination information is generated from the determination component.

In the fatigue state determination method according to the thirteenth aspect, the plurality of components is obtained by conducting the singular value decomposition, the principal component analysis, or the independent component analysis on the facial-surface change information after the predetermined action, and then the determination component related to the brain-function activation information is extracted from the plurality of components, thereby determining the fatigue state. Thus, the influence of the fatigue of the subject given by the predetermined action can be easily determined.

A fatigue state determination method according to a fourteenth aspect of the present invention is the fatigue state determination method according to the twelfth or thirteenth aspect, wherein in the fatigue state determination step, a correlation value of the determination information with respect to the brain-function activation information is calculated, and a fatigue state level of the subject is determined based on the calculated correlation value and the reference information. Here, an amount of change within a predetermined range from a reference correlation value to a correlation value of the determination information calculated with respect to the brain-function activation information is stored as reference information in relation to a fatigue state level, in a reference information storage unit.

In the fatigue state determination method according to the fourteenth aspect, the fatigue state level can be easily determined using the reference information stored in the reference information storage unit.

A fatigue state determination method according to a fifteenth aspect of the present invention is the fatigue state determination method according to the fourteenth aspect, wherein before the predetermined action, the brain-function activation information provision step, the facial-surface change information acquisition step, the facial-surface change information decomposition step, and the determination information generating step are executed to generate the reference information.

In the fatigue state determination method according to the fifteenth aspect, the reference information is extracted from the facial-surface change information on the subject before the predetermined action. Thus, the influence of the fatigue of the subject given by the predetermined action can be determined with high accuracy.

A fatigue state determination method according to a sixteenth aspect of the present invention is the fatigue state determination method according to the fourteenth or fifteenth aspect, wherein the fatigue state determination step includes accessing the determination information provision device when determining the fatigue state level. Here, the reference information storage unit is installed in a determination information provision device on a network.

In the fatigue state determination method according to the sixteenth aspect, the fatigue state is determined using the reference information stored in the determination information provision device on the external network, thereby making it possible to simplify the operation before the predetermined action. Moreover, the above-mentioned method can achieve the fatigue state determination using, for example, big data.

A fatigue state determination method according to a seventeenth aspect of the present invention is the fatigue state determination method according to the sixteenth aspect, wherein the reference correlation value is calculated by providing the brain-function activation information to a person other than the subject.

In the fatigue state determination method according to the seventeenth aspect, the fatigue state determination can be implemented by using big data or the like acquired from a person other than the subject.

A fatigue state determination method according to an eighteenth aspect of the present invention is the fatigue state determination method according to any one of the eleventh to seventeenth aspects, wherein the predetermined action is a predetermined physical activity, and the subject is a physical worker.

In the fatigue state determination method according to the eighteenth aspect, the fatigue state before and after an intellectual activity or a physical activity can be easily determined.

With the fatigue state determination device according to the first aspect, the fatigue state of the subject can be determined with the simple configuration.

With the fatigue state determination device according to the second aspect, the fatigue of the subject can be easily determined.

With the fatigue determination device according to the third aspect, the determination accuracy of the fatigue state of the subject can be enhanced.

With the fatigue state determination device according to the fourth aspect, the fatigue state of the subject can be easily determined based on the determination component corresponding to the brain function of the subject.

With the fatigue state determination device according to the fifth aspect, the reliability of the determination can be enhanced.

With the fatigue state determination device according to the sixth aspect, the fatigue state level can be easily determined.

With the fatigue state determination device according to the seventh aspect, the determination component related to the brain activity can be extracted with high accuracy.

With the fatigue state determination device according to the eighth aspect, the fatigue state can be determined using the infrared camera or the like.

With the fatigue state determination device according to the ninth aspect, the fatigue state can be determined using the solid-state imaging device or the like.

With the fatigue state determination device according to the tenth aspect, the fatigue state level of the subject can be determined using the determination information provision device on the network.

With the fatigue state determination method according to the eleventh aspect, the influence of the fatigue of the subject given by the predetermined action can be easily determined.

With the fatigue determination method according to the twelfth aspect, the determination accuracy of the fatigue state of the subject can be enhanced.

With the fatigue state determination method according to the thirteenth aspect, the influence of the fatigue of the subject given by the predetermined action can be easily determined.

With the fatigue state determination method according to the fourteenth aspect, the fatigue state level can be easily determined.

With the fatigue state determination method according to the fifteenth aspect, the influence of the fatigue of the subject given by the predetermined action can be determined with high accuracy.

With the fatigue state determination method according to the sixteenth aspect, the operation before the predetermined action can be simplified. Furthermore, by the above-mentioned method, the fatigue state determination using, for example, big data can be conducted.

With the fatigue state determination method according to the seventeenth aspect, the fatigue state determination can be conducted using big data or the like acquired from a person other than the subject.

With the fatigue state determination method according to the eighteenth aspect, the fatigue state before and after the intellectual activity or the physical activity can be easily determined.

DESCRIPTION OF EMBODIMENTS

Figure 1B:
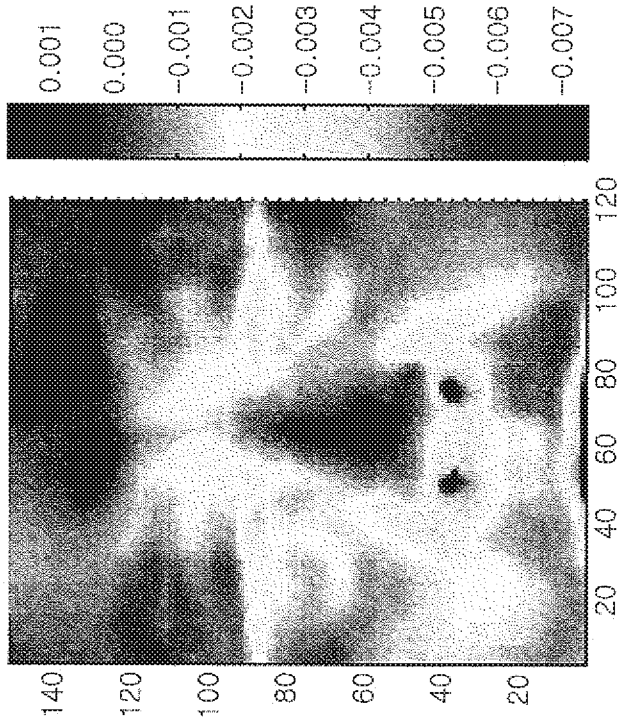
FIGS. 1A and 1B are diagrams showing an example of photographed image data and the analysis result of this data.

Prior to describing embodiments of the present invention, first, a description will be given on the findings conducted by the inventors, which have become an important basis in making the present invention.

(1) Main Points of Findings Conducted by Inventors

Human brain activities are known to reflect human intellectual activities (cognitive activity and the like) and emotional activities (pleasure/discomfort activities, and the like). Attempts to estimate the human brain activity have been conventionally made, but in this case, data detected by any of the electroencephalography, magnetic resonance imaging, and near infrared spectroscopy is often utilized.

Here, in a detection method, for example, brain wave electrodes need to be attached onto a test subject in the case of employing the electroencephalography. When the brain wave electrodes are attached onto the test subject, the resistance between the skin and the electrodes should be reduced. Due to this, additional operations, such as abrading the skin and applying a paste to the electrodes, are required. In addition, in the case of employing the magnetic resonance imaging method, the measurement conditions are limited. For example, the measurement of the brain waves cannot be performed in a place other than an MRI room, and metal is not permitted to be brought into a measurement room. Furthermore, in the case of employing the near infrared spectroscopy method, probes need to be attached onto a test subject. However, the test subject may feel pain when wearing the probes for a long time, or the brain waves cannot be accurately detected depending on the contact state between the hair of the test subject and the probes. As such, when a conventional detection method is employed to measure the human brain activity, a heavy burden is imposed on the test subject. For example, preprocessing is required when the test subject wears the brain wave electrodes, the probes, or the like, or the measurement conditions are limited.

Therefore, there is a need to develop a means for enabling easy estimation of the human brain activity while reducing the burden on the test subject.

The inventors have conceived that the human brain activity can be estimated based on the human's facial skin temperature, or the blood circulation state of the facial surface, which is considered to be proportional to the facial skin temperature. The human's facial skin temperature can be measured by using a measurement device, such as thermography, and the blood circulation state of the facial surface, that is, the facial blood circulation amount can be estimated from RGB data of a photographed image on the facial surface acquired using an imaging device. As such, the facial skin temperature or the photographed image on the facial surface can be acquired without attaching any sensor that requires preprocessing before attachment, such as brain wave electrodes or probes.

On the other hand, the human's facial skin temperature is known to change under the influence of various factors, such as the outside air temperature and/or the activity of autonomic nerves. Due to this, in case that the brain activity is estimated with intention based on the facial skin temperature or the facial blood circulation amount, which is considered to be proportional to the facial skin temperature, it is thought to be very difficult to determine whether the acquired data reflects only the brain activity.

As a result of intensive research, the inventors have found that time-series facial skin temperature data, which includes temperature data acquired by detecting facial skin temperatures and positional data (coordinate data) on a detected part, or time-series facial blood-circulation-amount data, which is calculated based on the RGB data obtained from the time-series photographed image data on the facial surface, is decomposed into a plurality of components by the singular value decomposition method, principal component analysis method, or independent component analysis method, and then the decomposed components are analyzed, which can identify the component indicative of the changes in the facial skin temperature or changes in the facial blood circulation amount that reflect the brain activity. Eventually, the inventors have estimated and analyzed the brain activity of the subject and hence reached the present invention capable of visualizing the physiological state of the subject based on the estimated brain activity.

(2) Acquiring Method of Various Data Regarding Facial Surface and Analyzing Method of Acquired Various Data

(2-1) Acquiring Method of Facial Skin Temperature Data and Analyzing Method of Facial Skin Temperature Data Next, a description will be given on the acquiring method of the facial skin temperature data, used by the inventors to obtain the above findings, as well as the analyzing method of the facial skin temperature data.

In the present test, facial skin temperature data was acquired from six test subjects. Specifically, each test subject was seated on a chair placed in an artificial weather room maintained at room temperature of 25° C., and facial skin temperature data was acquired from the entire facial surface of the subject by using an infrared thermography device. The infrared thermography device is a device which detects infrared radiant energy emitted from an object with an infrared camera, then converts the detected infrared radiant energy into a temperature of a surface of the object (here, a temperature in units of Celsius), and thereby can display and store the temperature distribution of the converted temperatures as the facial skin temperature data (for example, image data representing the temperature distribution). Note that in the present test, an R300 manufactured by NEC Avio Infrared Technologies Co., Ltd. was used as an infrared thermography device. The infrared camera was placed in front of the test subject and at a distance of 1.5 m from the test subject. Subsequently, acquiring the facial skin temperature data was continued for 30 minutes.

In the present test, a brain function activation task was given to the test subject, while the facial skin temperature data was being acquired. Thus, the facial skin temperature data during a brain non-activation time and the facial skin temperature data during a brain activation time were acquired. The brain function activation tasks include psychological operations done by a test subject based on a picture displayed on a display device or the like, such as calculation, recognition of numerical values, shape, and color, and memorization of marks, characters, and languages. In the present test, "mental arithmetic of multiplication" was adopted as the brain function activation task, which forces the test subject to do operations, such as calculating numerical characters displayed on a display device in longhand and inputting answers on a keyboard. Note that in the present test, the brain function activation task was continuously given to the test subjects for ten minutes after five minutes have elapsed since the start of acquiring the facial skin temperature data.

In the analysis of the facial skin temperature data, the singular value decomposition was performed on the acquired facial skin temperature data by using the SVD (Singular Value Decomposition) of MATLAB (registered trademark) as an analysis tool. In the singular value decomposition, the target was defined as all the facial skin temperature data acquired in time series (data for 30 minutes), the factor was defined as time data acquired every 30 seconds (60 time points for 30 minutes), and the measure was defined as the facial skin temperature data (240×320 pixels) in that time period (30 seconds). By the singular value decomposition, the facial skin temperature data X was decomposed into a plurality of components, and then a time distribution V and a space distribution U of each of the components and a singular value S indicative of the size of each component were calculated.

Note that the relationship between these can be given by the formula below:

$$X=(U*S)*V^{+} \quad \text{[Formula 1]}$$

where V' is a matrix configured by interchanging columns and rows of V.

Then, the time distribution V and the space distribution U of each component determined by the singular value decomposition were plotted in graphs to generate a component waveform diagram and a temperature distribution diagram of each component.

Further, the thus-formed component waveform diagram and temperature distribution diagram of each component were analyzed to identify a component which exhibited a change in the skin temperature that reflected the brain activity.

Regarding the component waveform diagram of each component, analysis was conducted on the presence or absence of the correlation between the amplitude of the component waveform and each of the brain non-activation time and the brain activation time. Specifically, it was evaluated whether or not there was a correlation between the amplitude shown in the component waveform diagram of each component and the brain non-activation period/activation period. In the present test, during the period of time when the facial skin temperature data was being acquired, the brain non-activation time was defined as a period of time with no brain function activation task given to the test subject, and specifically, a period of five minutes from the start of data acquisition and a period of 15 minutes from when 15 minutes had elapsed since the start of data acquisition to the end of data acquisition, whereas the brain activation time was defined as a period of time with the brain function activation task given to the test subject, and specifically, a period of ten minutes from the time when five minutes had elapsed since the start of data acquisition to the time when ten minutes had elapsed since then. Regarding the component waveform diagram of each component, analysis was conducted on the presence or absence of the correlation between the amplitude of the component waveform and each of the brain non-activation time and the brain activation time. It is noted that the presence or absence of the correlation was determined by using a statistical correlation analysis; the correlation was determined to be present if a significance level (at) was 0.05 or less.

Regarding the temperature distribution diagram of each component, analysis was conducted on the presence or absence of a temperature change at a predetermined part of the facial surface. Here, the brain has a mechanism called "Selective Brain Cooling System", which cools the brain independently of body temperature. The selective brain cooling system is known to discharge heat generated by the brain activity through the forehead and the paranasal sinus peripheral region (including the glabella and the surroundings of the nose). In the present test, it was evaluated whether or not there is a temperature change in the paranasal sinus peripheral region and the forehead on the temperature distribution diagram of each component. The presence or absence of a temperature change in the paranasal sinus peripheral region and the forehead in the temperature distribution diagram was determined by visual inspection of the presence or absence of the temperature change, or based on whether or not the temperature in the paranasal sinus peripheral region and the forehead differs by 1 standard deviation (SD) or more from the mean temperature of the entire measured data.

It is noted that the polarity (plus or minus) of the facial skin temperature data X is determined depending on the relationship among the values of the space distribution U, the singular value S, and the time distribution V. and hence the polarity appears to be inversed in the component waveform diagram and the temperature distribution diagram of each component in some cases. Thus, with regard to the evaluation of the component waveform diagram and the temperature distribution diagram, the polarity was not set as an evaluation target.

Here, as mentioned above, the infrared thermography device converts infrared radiant energy detected from a part of an object into temperatures and then utilizes the temperature distribution of those temperatures as the facial skin temperature data. When the facial skin temperature of a human is acquired as the target using the infrared thermography device, temperature changes (so-called noises) that are not related to various brain activities, such as facial movement and/or autonomic nerve activity, might also be acquired as the facial skin temperature data (see FIG. 1A). For this reason, in order to detect such a temperature change not related to the brain activity, relative facial skin temperature data was created so as to set an average value of all temperature data included in the facial skin temperature data captured every 30 seconds to "0". Then, the created facial skin temperature data was also subjected to the singular value decomposition using the SVD of MATLAB (registered trademark) as an analysis tool, thereby creating a component waveform diagram and a temperature distribution diagram of each component corresponding to a singular value S. Referring to this, analysis was conducted to identify components exhibiting the changes in the skin temperature that reflected the brain activities.

Hereinafter, for convenience of the description, the facial skin temperature data acquired in the infrared thermography device will be referred to as the "facial skin temperature data corresponding to the temperature conversion data". Meanwhile, the relative facial skin temperature data created by setting an average value of all temperature data included in the facial skin temperature data corresponding to the temperature conversion data every predetermined time (in the present test, every 30 seconds) to "0" will be referred to as the "facial skin temperature data corresponding to the relative temperature conversion data".

With regard to one of six test subjects, in addition to detecting the facial skin temperature by the infrared thermography device, electrodes were connected and attached on the scalp of the test subject to measure his or her brain waves, thereby evaluating the correlation between the amplitude of each component shown in the component waveform diagram and the amplitude of β waves (brain waves at frequencies of 14 to 30 Hz), which are known to have a waveform appearing in an awake or stressed human. In the electroencephalography, electrodes were placed at six parts (F3, F4, C3, C4, Cz, Pz) based on the International 10-20 method.

On the other hand, it can be considered that the head of the test subject moves up and down while the test subject is given a brain function activation task. In such a case, the position of the test subject's facial surface changes with respect to the infrared camera. A control test was conducted on one test subject to verify whether or not this change in the facial position influences changes in the skin temperature. In the control test for verifying the influence of the test subject's movement in acquiring the facial skin temperature data, the infrared thermography device is used as with the above-mentioned test to thereby acquire the facial skin temperature data regarding the test subject. In addition, the test subject was forced to do an operation of pressing a keyboard at random timings, while the brain function activation task was not given applied to the test subject (i.e., during the brain non-activation time). Also, with regard to the facial skin temperature data corresponding to the temperature conversion data obtained in this control experiment and the facial skin temperature data corresponding to the relative temperature conversion data, the singular value decomposition was conducted using the SVD of MATLAB (registered trademark) as the analysis tool, thereby generating a component waveform diagram and a temperature distribution diagram of each component corresponding to a singular value S. In this way, the analysis was conducted to identify components exhibiting the changes in the skin temperature that reflected the brain activities.

Figure 1A:
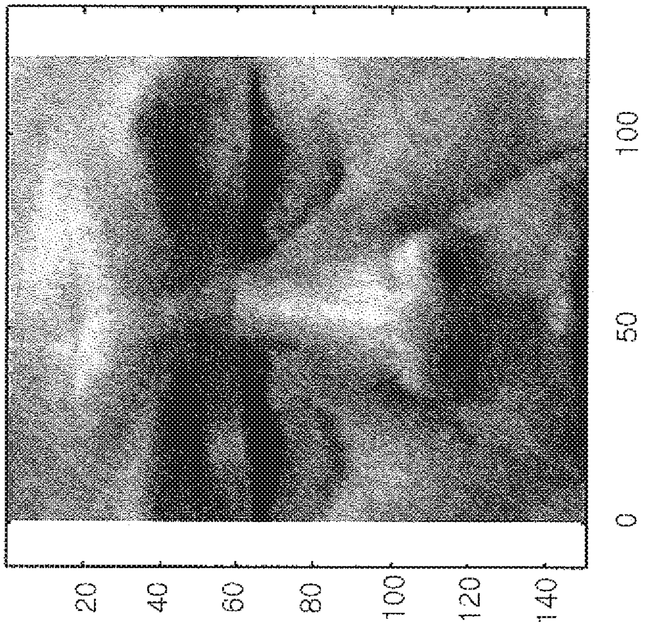

(2-2) Acquiring Method of Photographed Image Data on the Facial Surface and Analyzing Method of Photographed Image Data on the Facial Surface FIG. 1A is a diagram showing an example of photographed image data acquired from the paranasal sinus peripheral region on the facial surface of the test subject, photographed by an imaging device. FIG. 1B is a diagram showing an example of a blood circulation amount distribution diagram (image map).

Next, a description will be given on the acquiring method of photographed image data on the facial surface as well as the analyzing method of photographed image data on the facial surface, which were used by the inventors to obtain the above-mentioned findings.

In the present test, the photographed image data were acquired from the faces of six test subjects. Specifically, each test subject was seated on a chair placed in an artificial weather room maintained at room temperature of 25° C., and then the photographed image data on the paranasal sinus peripheral region at the entire facial surface of each test subject was acquired in time series by using an imaging device capable of acquiring images in time series.

Furthermore, based on the above-mentioned selective brain cooling mechanism, the changes in the facial blood circulation amount, which is considered to be proportional to the facial skin temperature related to the brain activity, are thought to appear around the forehead and/or paranasal sinuses. Through this, the inventors have conceived that recognizing the changes in the facial blood circulation amount around at least one of the forehead and/or the paranasal sinuses can estimate the brain activity with high accuracy. To this end, the present test acquired the photographed image data on the paranasal sinus peripheral region at the facial surface of the test subject in time series.

In the present test, color moving image data was acquired as time-series photographed image data by using an imaging device mounted on the side of a liquid crystal display of iPad Air (registered trademark), manufactured by Apple Inc., as the imaging device. The imaging device was placed in front of the test subject and at a distance of 1.0 m from the test subject. Then, the moving image data on the facial surface of the test subject was acquired by continuously capturing the photographed image data for 30 minutes along the time axis in a capturing cycle of 30 frames/sec using the imaging device.

In the present test, a brain function activation task was given to the test subject, while the moving image data on the facial surface was being acquired. In this way, the moving image data on the facial surface during the brain non-activation time and during the brain activation time were acquired. In the present test, like the above-mentioned test, “mental arithmetic of multiplication” was adopted as the brain function activation task, which forces the test subject to do operations, such as calculating numerical characters displayed on a display device in longhand and inputting answers on a keyboard. Note that in the present test, the brain function activation task was given to the test subject for ten minutes after five minutes have elapsed since the start of acquiring the moving image data on the facial surface.

In the analysis of the moving image data on the facial surface, blood-circulation-amount data was calculated based on the RGB data acquired from the moving image data on the photographed facial surface, and then the calculated time-series blood-circulation-amount data was subjected to a singular value decomposition by using the SVD of MATLAB (registered trademark) as an analysis tool. Here, an erythema index “a*” that correlates with skin redness and hemoglobin amount computed from the RGB data on the image was determined as the blood-circulation-amount data in accordance with the CIE-L*a*b* color coordinate system. In the singular value decomposition, the target was defined as the blood-circulation-amount data (here, erythema index) determined based on the RGB data acquired from all the moving image data (data acquired for 30 minutes) in time series, the factor was defined as time data acquired every 30 seconds (60 time points for 30 minutes), and the measure was defined as the erythema index computed from the RGB data in that time period (every 30 seconds) (erythema index obtained by taking frame data for one second every 30 seconds and computing from an average of RGB values obtained from the frame data; 240×320 pixels). By the singular value decomposition, the time-series blood-circulation-amount data based on the RGB data acquired from the moving image data on the facial surface was decomposed into a plurality of components, and then a time distribution V and a space distribution U of each component and a singular value S indicative of the size of each component were calculated. Note that these relationships can be given by the same formula as the above-mentioned formula (Formula 1).

Then, the time distribution V and the space distribution U of each component determined by the singular value decomposition were plotted in graphs to generate a component waveform diagram and a blood circulation amount distribution diagram of each component.

Further, the thus-generated component waveform diagram and blood circulation amount distribution diagram of each component were analyzed to identify a component which exhibited a change in the facial blood circulation amount that reflected the brain activity, i.e., an RGB change on the facial surface.

Regarding the component waveform diagram of each component, analysis was conducted on the presence or absence of the correlation between the amplitude of the component waveform and each of the brain non-activation time and the brain activation time. Specifically, it was evaluated whether or not there was a correlation between the amplitude of the component shown in the component waveform diagram of each component and the brain non-activation period/activation period. In the present test, for a period of time during which the photographed image data on the facial surface was being acquired, the brain non-activation time was defined as a period of time with no brain function activation task given to the test subject, and specifically, a period of five minutes from the start of data acquisition and a period of 15 minutes from when 15 minutes had elapsed since the start of data acquisition to the end of data acquisition, whereas the brain activation time was defined as a period of time with the brain function activation task given to the test subjects, and specifically, a period often minutes from the time when five minutes had elapsed since the start of data acquisition to the time when ten minutes had elapsed since then. Regarding the component waveform diagram of each component, evaluation was conducted on the presence or absence of the correlation between the amplitude of each component shown in the component waveform diagram and each of the brain non-activation time and the brain activation time. It is noted that the presence or absence of the correlation was determined by using a statistical correlation analysis; the correlation was determined to be present if a significance level ($\alpha$) was 0.01 or less.

Regarding the blood circulation amount distribution diagram of each component, analysis was conducted on the presence or absence of a change in the blood circulation amount at a predetermined part of the facial surface. The blood circulation amount distribution diagram was generated by arranging the space distributions U calculated every pixel, at the position of each pixel. In the blood circulation amount distribution diagram of each component created in this way, it was evaluated whether or not there was any change in the blood circulation amount at the paranasal sinus peripheral region and/or the forehead. Note that the presence or absence of a change in the blood circulation amount at the paranasal sinus peripheral region and/or the forehead in the blood circulation amount diagram was determined with reference to visual inspection of the presence or absence of the change in the blood circulation amount, or whether the values of the blood circulation amount at the paranasal sinus peripheral region and the forehead shown in FIG. 1B were not "0.000".

It is noted that the polarity (plus or minus) of the blood-circulation-amount data X is determined depending on the relationship among the values of the space distribution U, the singular value S, and the time distribution V, and hence the polarity appears to be inversed in the component waveform diagram and the blood circulation amount distribution diagram of each component in some cases. Thus, with regard to the evaluation of the component waveform diagram and the blood circulation amount distribution diagram, the polarity was not set as an evaluation target.

Further, to verify the correlation between the facial skin temperature and the facial blood circulation amount, while the photographed image data on the facial surface was acquired from the six test subjects in time series, the facial skin temperature data was also acquired in time series by the infrared thermography device. Then, the acquired facial skin temperature data was also subjected to the singular value decomposition by using the SVD of MATLAB (registered trademark) as the analysis tool. The component waveform diagram for each component corresponding to the singular value S was generated. Based on this diagram, analysis was conducted on the presence or absence of the correlation between the amplitude of the component waveform and each of the brain non-activation time and the brain activation time. In the present test, the same device as that used in the above-mentioned test was used as an infrared thermography device. The infrared camera was placed in front of the test subject and at a distance of 1.5 m from the test subject.

In a case where the photographed image data on a facial surface is acquired by using the imaging device, if sunlight or the like hits the face during photographing, the light is reflected by the face. The reflected light occasionally enters a lens of the imaging device. As a result, the photographed image data on the photographed facial surface would have the reflected light recorded therein. Here, in the RGB data acquired from the photographed image data, a change in brightness based on the facial blood circulation amount is smaller than a change in brightness based on the reflected light. Because of this, if a blood circulation amount calculated based on the RGB data acquired from the photographed image data with the reflected light recorded therein is analyzed, it is considered that an RGB change (which is so-called noise) on the facial surface, which is unrelated to the brain activity, could be mixed in the RGB data. For this reason, in order to prevent mixing of such an RGB change on the facial surface not related to the brain activity, relative blood-circulation-amount data was created from the relative RGB data in which an average value of all RGB data acquired every 30 seconds was set to "0". Then, the created blood-circulation-amount data was subjected to the singular value decomposition using the SVD of MATLAB (registered trademark) as the analysis tool, thereby generating a component waveform diagram and a blood circulation amount distribution diagram of each component corresponding to a singular value S. In this way, analysis was conducted to identify components exhibiting the RGB changes on the facial surface that reflected the brain activities.

Hereinafter, for convenience of the description, the relative blood-circulation-amount data based on the relative RGB data created so as to set an average value of all RGB data obtained every predetermined time (in the present test, every 30 seconds) to "0" will be referred to as the "relative-conversion blood-circulation-amount data". Meanwhile, the blood-circulation-amount data based on the RGB data before conversion to the relative RGB data will be simply referred to as the "blood-circulation-amount data".

While the time-series photographed image data on the facial surfaces of six test subjects were being acquired by the imaging device, their brain waves were measured by connecting electrodes on the scalp of each test subject, thereby evaluating the correlation between the amplitude of each component shown in the component waveform diagram and the amplitude of β waves (brain waves at frequencies of 13 to 30 Hz), known to have a waveform appearing while the brain is active, such as the state of being awake or the like. In the electroencephalography, electrodes were placed at 19 parts on the scalp (Fp1, Fp2, F3, F4, C3, C4, P3, P4, O1, O2, F7, F8, T3, T4, T5, T6, Fz, Cz, and Pz) based on the International 10-20 method.

Furthermore, it can be considered that the head of the test subject moves up and down while the test subject is given a brain function activation task. In such a case, the position of the test subject's facial surface changes with respect to the imaging device. A control test was conducted on one test subject to verify whether or not this change in the facial position influences RGB changes on the facial surface. In the control test, the time-series photographed image data on the test subject's facial surface was acquired using the imaging device in the same manner as the above-mentioned test. In addition, the test subject was forced to do an operation of pressing a keyboard at random timings, while the brain function activation task was not given (i.e., during the brain non-activation time). Then, the singular value decomposition was also conducted on the time-series blood-circulation-amount data based on the RGB data acquired from the time-series photographed image data on the facial surface, photographed in the control test, by using the SVD of MATLAB (registered trademark) as the analysis tool. Subsequently, the component waveform diagram for each component corresponding to the singular value S was generated. Based on this diagram, analysis was conducted on the presence or absence of the correlation between the amplitude of the component waveform and each of the brain non-activation time and the brain activation time. In addition, analysis was conducted on the presence or absence of the correlation between the amplitude of each component waveform and an actual movement of the facial surface. An actual movement of the facial surface was evaluated by acquiring two-dimensional coordinates of one part on the face from the photographed image data, and calculating each movement distance of the facial surface every 30 seconds during photographing with reference to photographed image data of the start of the control experiment. Furthermore, analysis was also conducted on the presence or absence of the correlation between the amplitude of each component waveform and the number of inputs into the keyboard during the photographing. The number of inputs into the keyboard during the photographing was evaluated by calculating a simple moving average every 30 seconds in the time-series photographed image data.

(3) Analysis Result (3-1) Analysis Results of Facial Skin Temperature Data

Figure 2A:
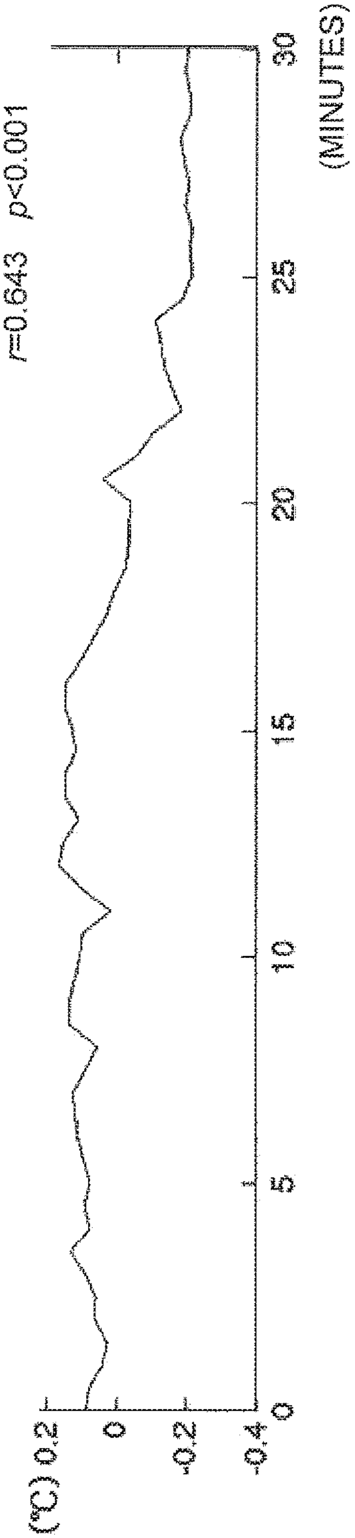
FIGS. 2A and 2B are diagrams showing part of the analysis result of facial skin temperature data.
Figure 2B:
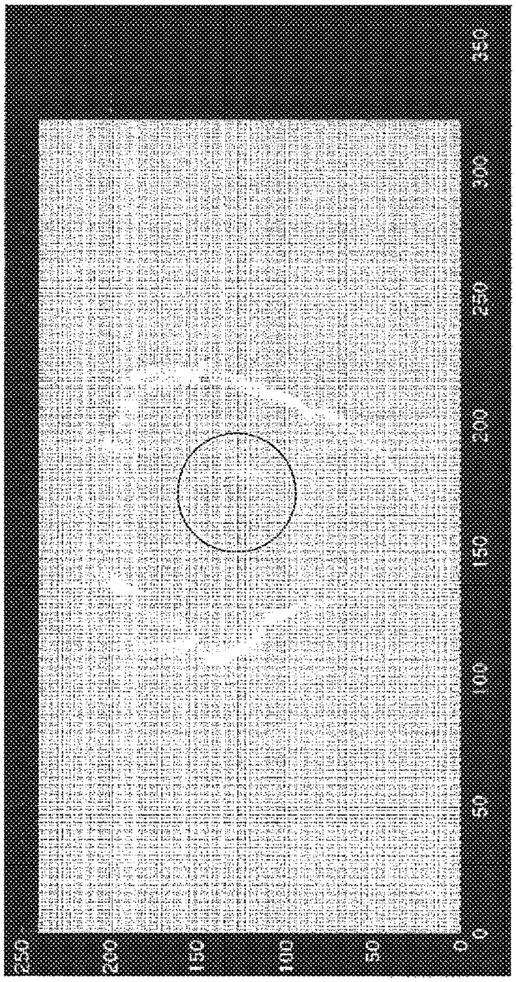
Figure 3A:
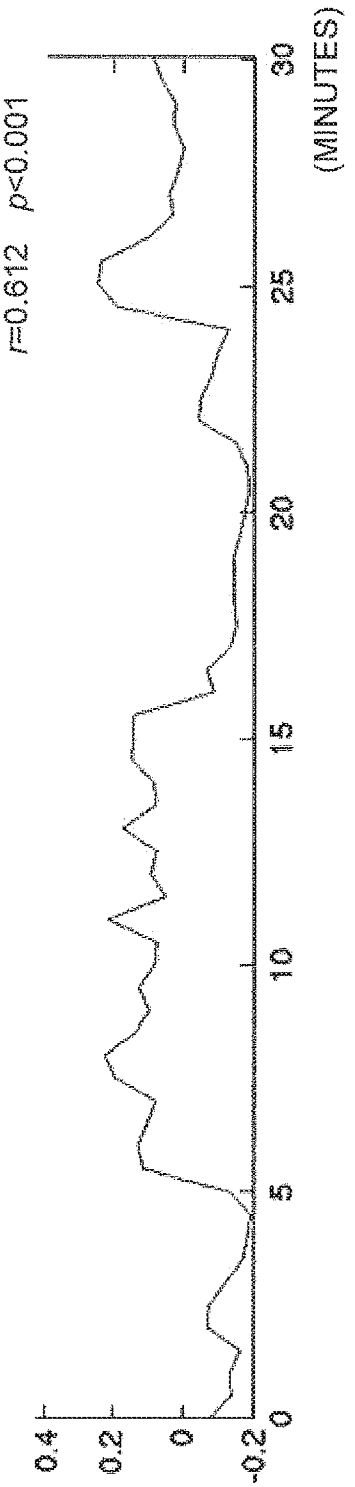
FIGS. 3A and 3B are diagrams showing part of the analysis result of the facial skin temperature data.
Figure 3B:
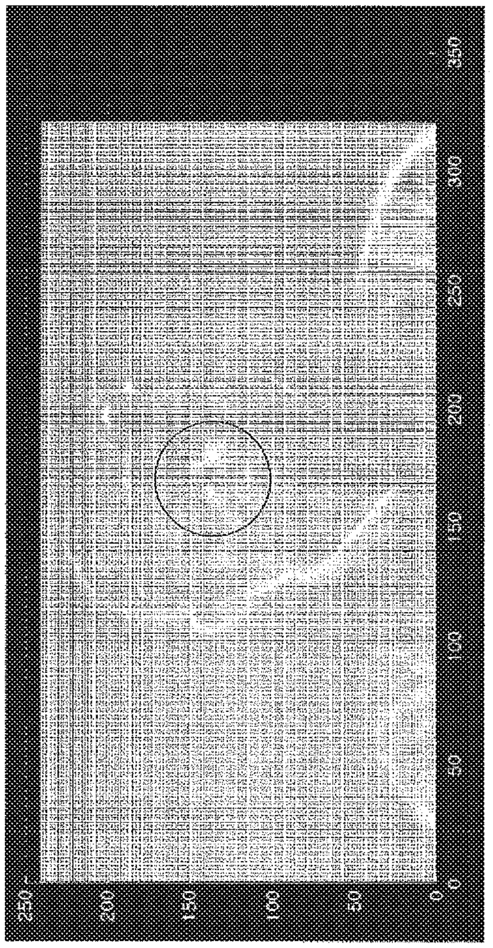
Figure 4:
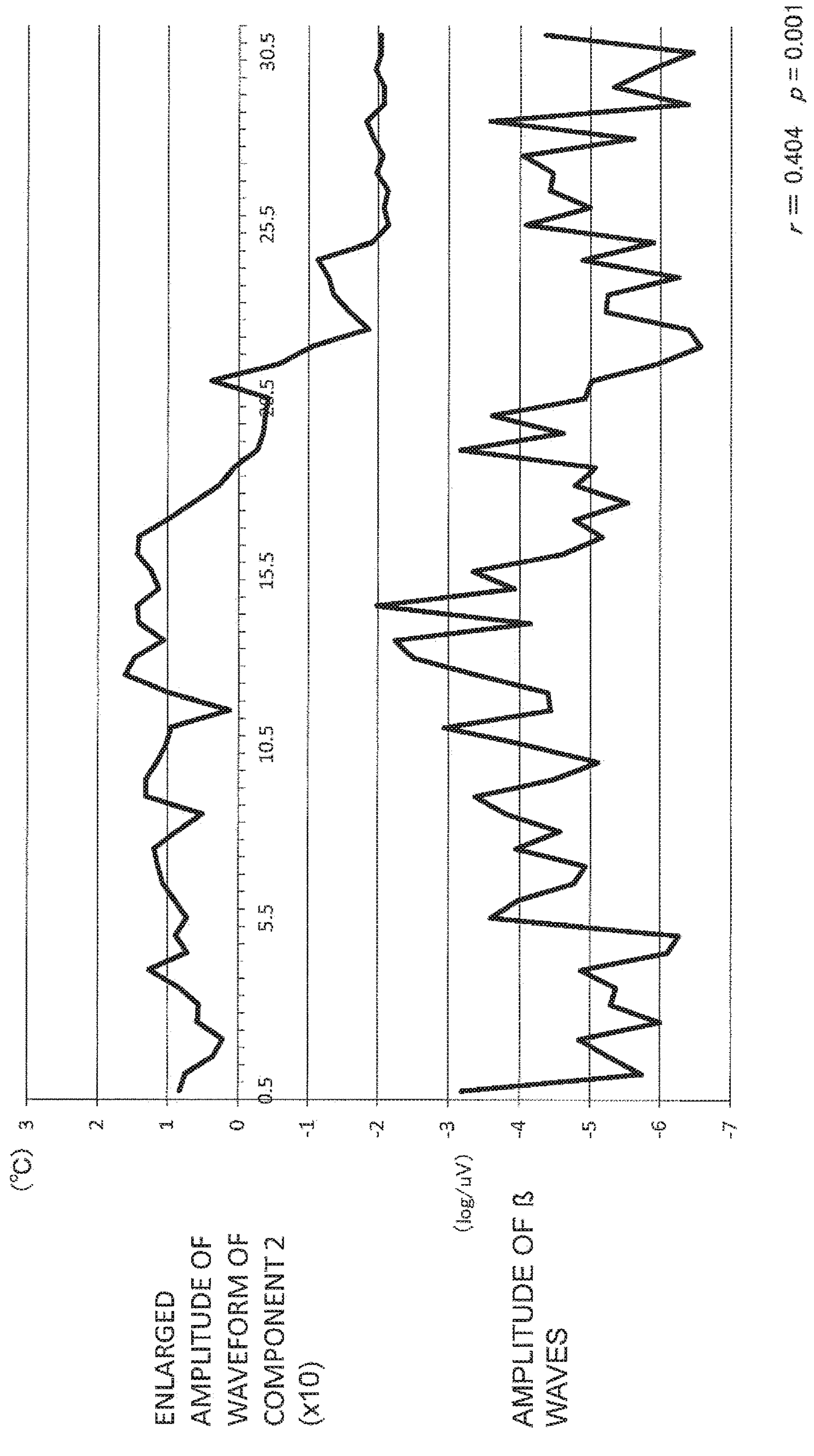
FIG. 4 is a diagram showing the amplitude of a component waveform of a component 2 and an amplitude of β waves among measured brain waves.
Figure 5:
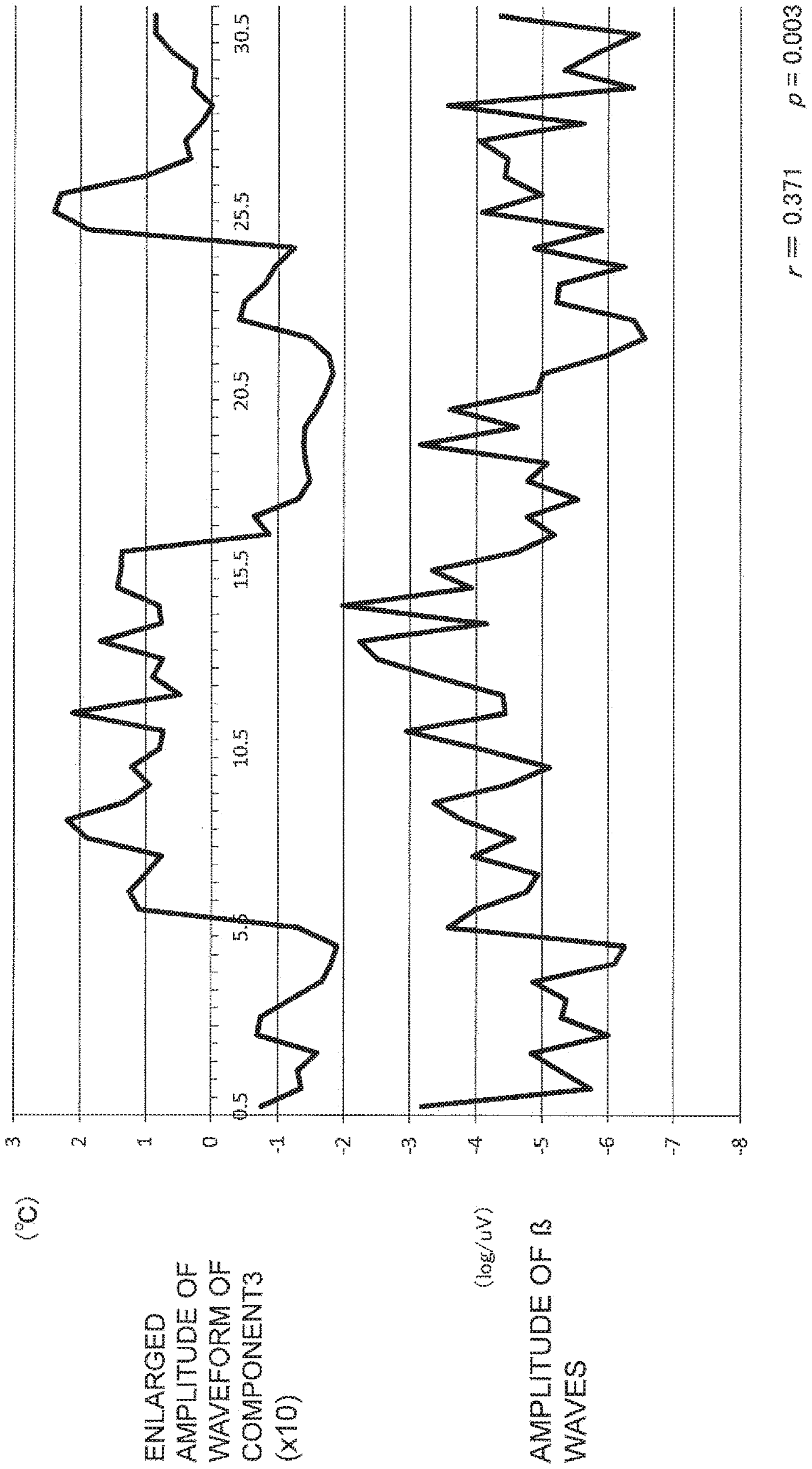
FIG. 5 is a diagram showing the amplitude of a component waveform of a component 3 and an amplitude of β waves among measured brain waves.
Figure 6A:
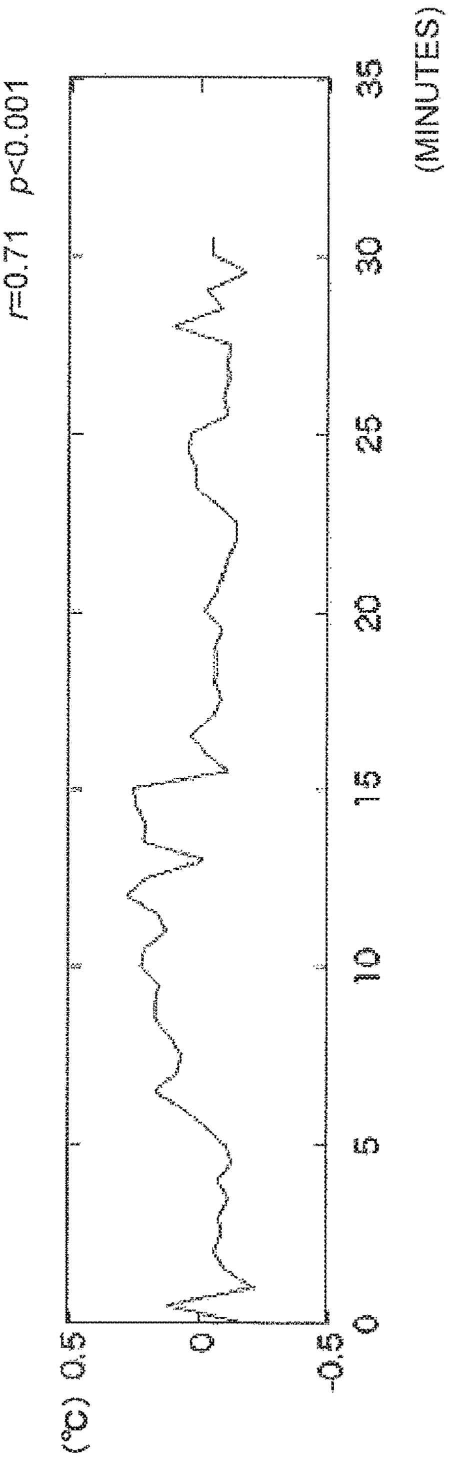
FIGS. 6A and 6B are diagrams showing part of the analysis result of the facial skin temperature data acquired in a control experiment.
Figure 6B:
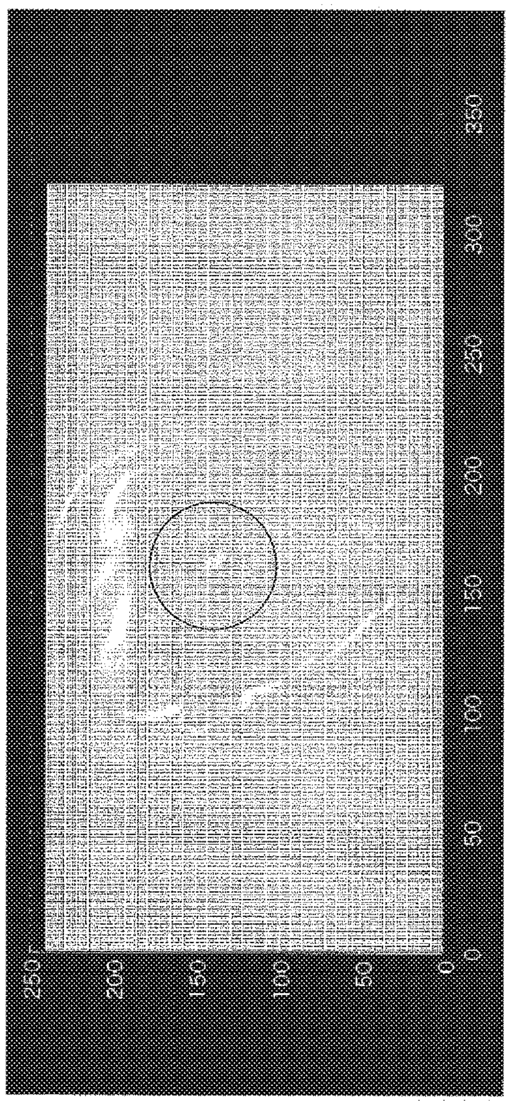

FIGS. 2A and 2B are diagrams showing parts of the analysis results of facial skin temperature data corresponding to temperature conversion data. FIG. 2A shows a component waveform diagram of a component 2 of a test subject 1. FIG. 2B shows a temperature distribution diagram of the component 2 of the test subject 1. FIG. 3A shows a component waveform diagram of a component 3 of the test subject 1. FIG. 3B shows a temperature distribution diagram of the component 3 of the test subject 1. FIGS. 4 and 5 are diagrams showing the relationships between the amplitudes of the component waveforms and brain waves. FIG. 4 is a diagram showing the amplitude of a component waveform of the component 2 exhibited by the test subject 1 and the amplitude of β waves among measured brain waves. FIG. 5 is a diagram showing the amplitude of a component waveform exhibited by the component 3 of the test subject 1 and the amplitude of β waves of the measured brain waves, FIGS. 6A and 6B are diagrams showing parts of the analysis results of the facial skin temperature data acquired in a control experiment. FIG. 6A shows a component waveform diagram of the component 3, FIG. 6B shows a temperature distribution diagram of the component 3.

Table 1 shows analysis results of facial skin temperature data corresponding to each test subject.

From the results obtained by the analysis of the above-mentioned facial skin temperature data, a significant correlation was confirmed between the human brain activity and the component 2 and/or component 3 among a plurality of components obtained by decomposing the time-series facial skin temperature data through the singular value decomposition.

TABLE 1

| | Correlation with data based on the absolute temperature conversion data | | Correlation with data based on relative temperature conversion data | |
|---|---|---|---|---|
| Test subject | Component waveform | Temperature distribution | Component waveform | Temperature distribution |
| Test subject 1 | Component 2 | Component 2 | Component 2 | Component 2 |
| | Component 3 | Component 3 | Component 3 | Component 3 |
| Test subject 2 | Component 3 | Component 3 | Component 3 | Component 3 |
| Test subject 3 | Component 1 | Component 2 | Component 2 | Component 2 |
| | Component 2 | Component 3 | Component 3 | Component 3 |
| | Component 3 | | | |
| Test subject 4 | Component 2 | Component 2 | Component 2 | Component 2 |
| | Component 3 | Component 3 | Component 3 | Component 3 |
| Test subject 5 | Component 2 | Component 2 | Component 2 | Component 2 |
| | Component 3 | Component 3 | Component 3 | Component 3 |
| Test subject 6 | Component 2 | Component 2 | Component 2 | Component 2 |
| | Component 5 | Component 5 | Component 5 | Component 5 |

As shown in FIGS. 4 and 5, from the results of the brain wave analysis, a significant correlation was confirmed between the amplitude of each of the component waveforms of the component 2 and the component 3 and the amplitude of the β waves of the brain waves.

In the control experiment, there was still a significant correlation between the component 3 and the human brain activity even in a state where the test subject was moving while the facial skin temperature data was being acquired (see FIG. 6). From this fact, it was confirmed that the component 3 of the plurality of components was not influenced by the movement of the test subject when the facial skin temperature data was acquired.

According to these results, the inventors have obtained the following findings.

The time-series facial skin temperature data acquired from the test subject was decomposed into a plurality of components by the singular value decomposition, and then each of the decomposed components was analyzed. As a result of this analysis, the component 3 among the plurality of components was confirmed to be a component related to the brain activity. That is, it has been found that the time-series facial skin temperature data is decomposed into a plurality of components by the singular value decomposition, subsequently a component having a correlation with the activation/non-activation of the brain is extracted from the plurality of decomposed components, and then the extracted component is analyzed using the selective brain cooling system, so that the component indicative of the change in the skin temperature which reflects the brain activity can be identified from the plurality of components. Accordingly, the inventors have obtained the finding that the brain activity can be estimated based on the human's facial skin temperature.

(3-2) Analysis Results of Photographed Image Data on the Facial Surface

Figure 7:
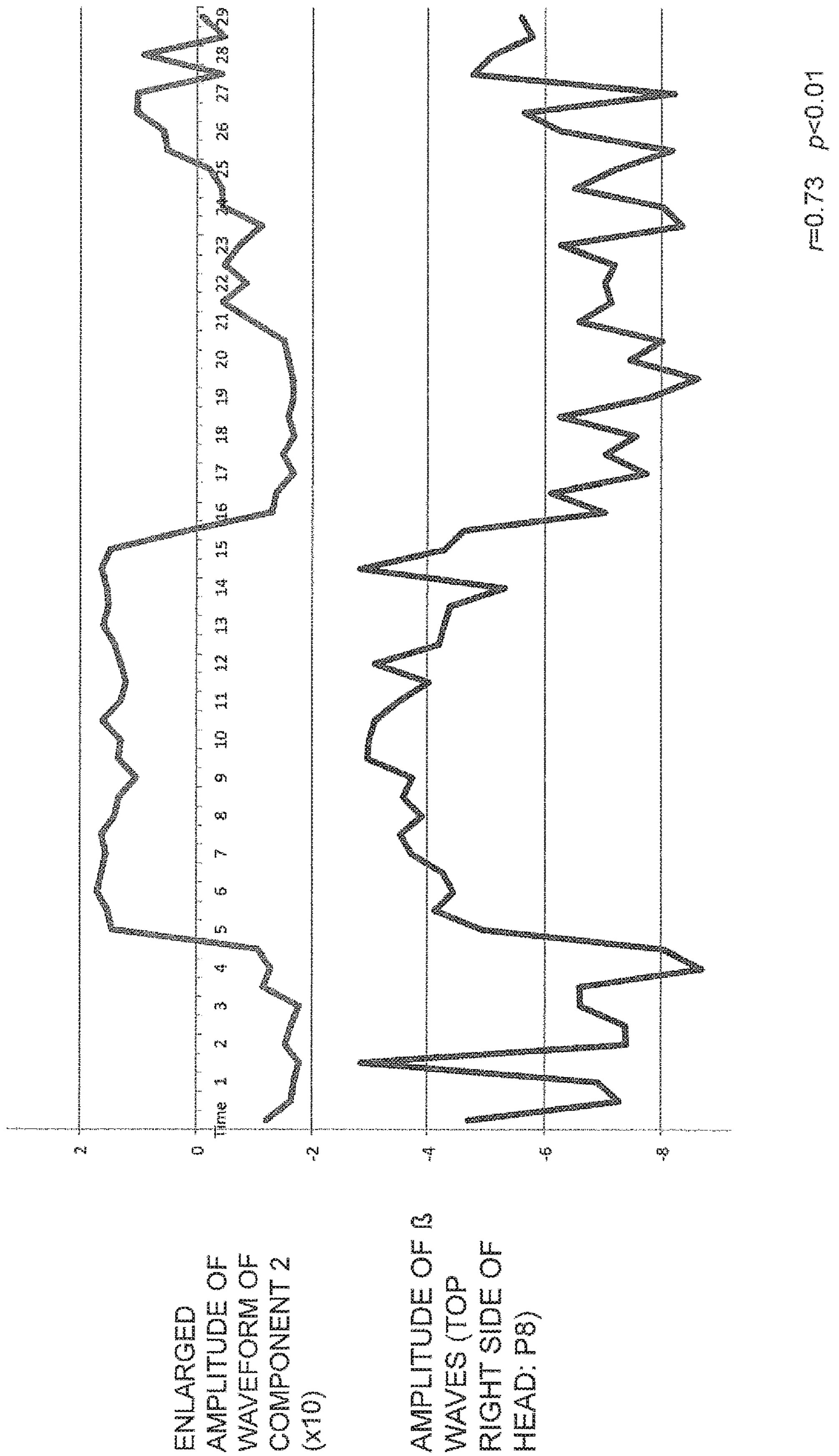
FIG. 7 is a diagram showing a component waveform based on photographed image data on a facial surface and the amplitude of β waves among measured brain waves.
Figure 8:
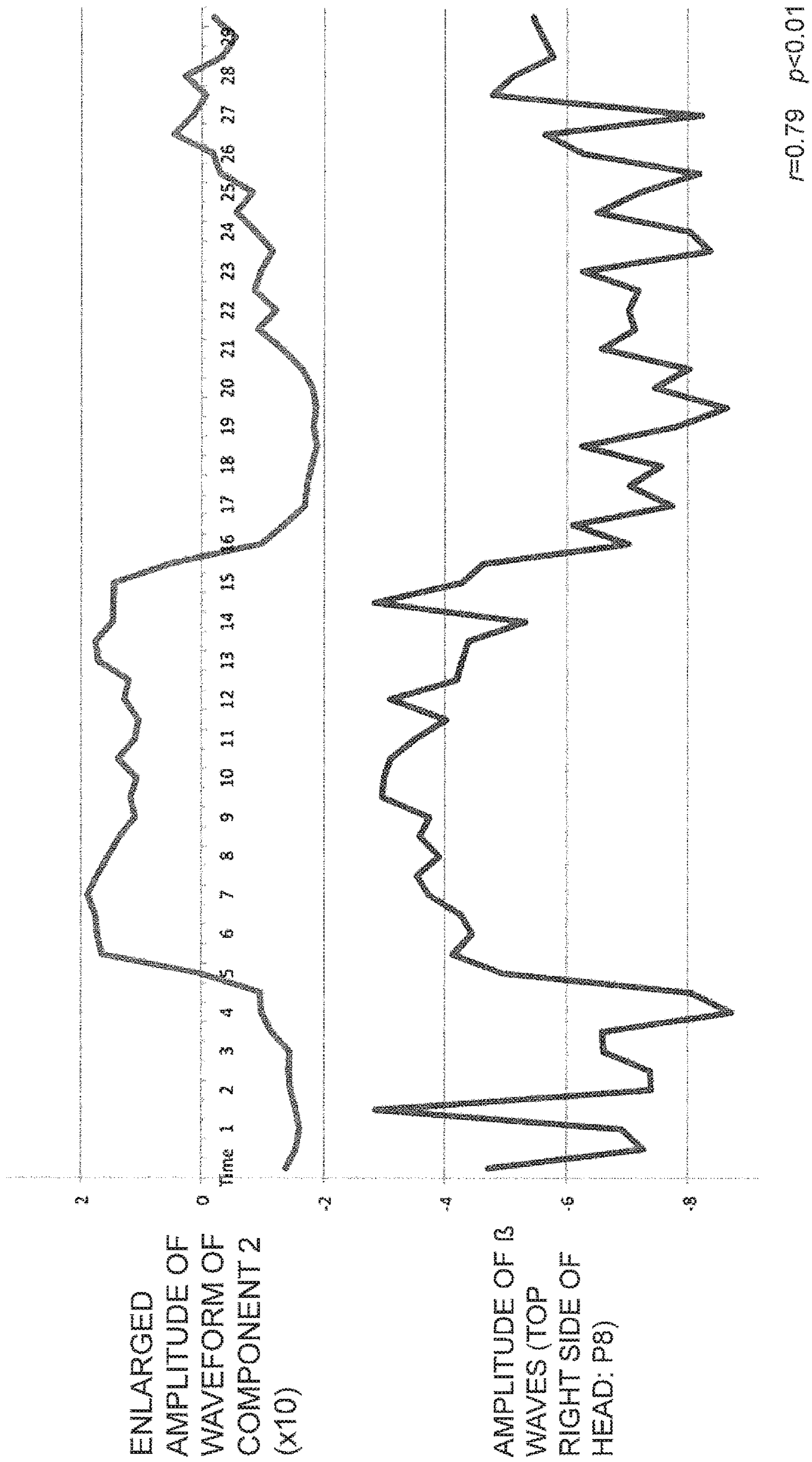
FIG. 8 is a diagram showing a component waveform based on facial skin temperature data and the amplitude of βwaves among measured brain waves.
Figure 9:
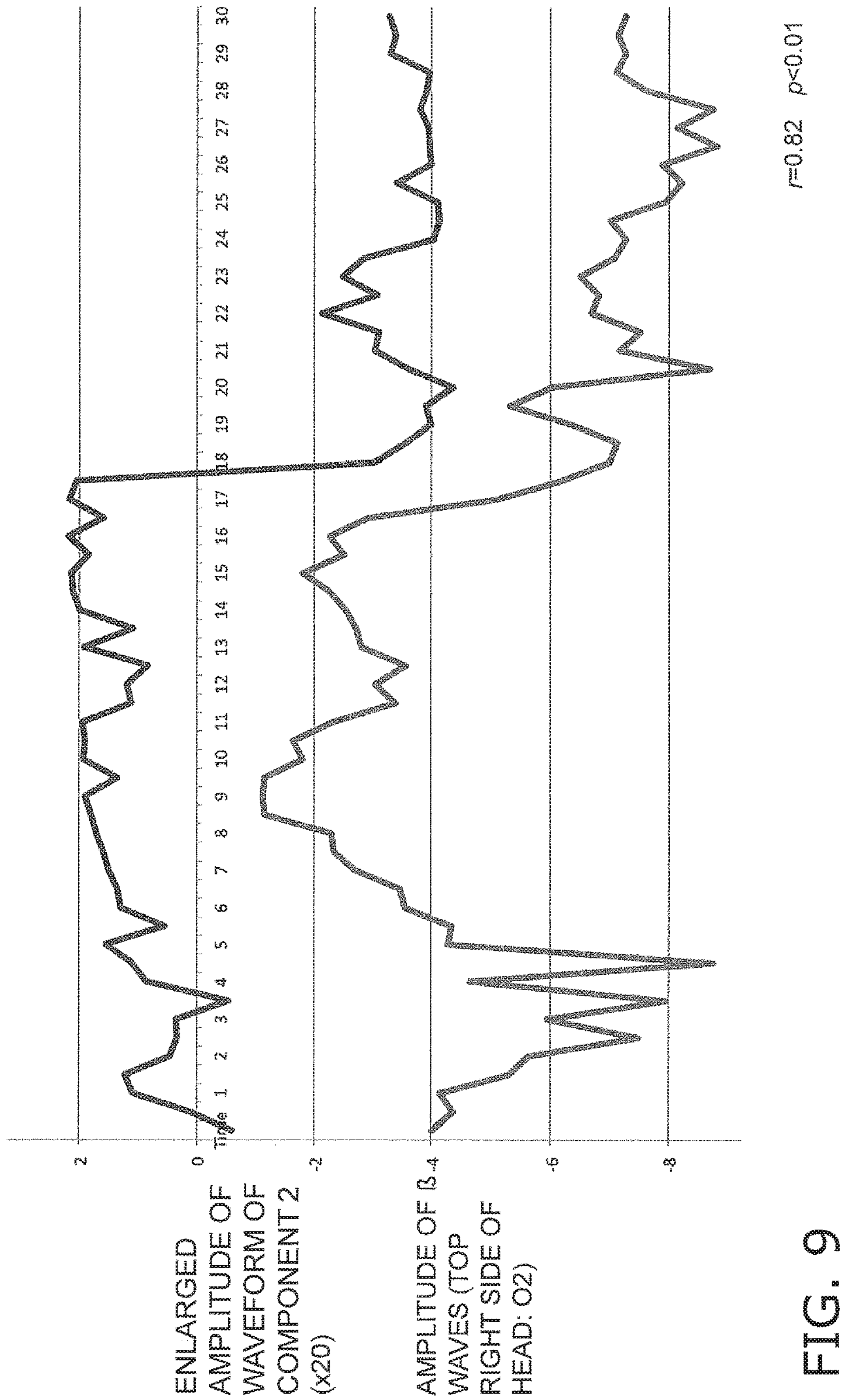
FIG. 9 is a diagram showing a component waveform based on photographed image data on a facial surface and the amplitude of βwaves among measured brain waves.
Figure 10:
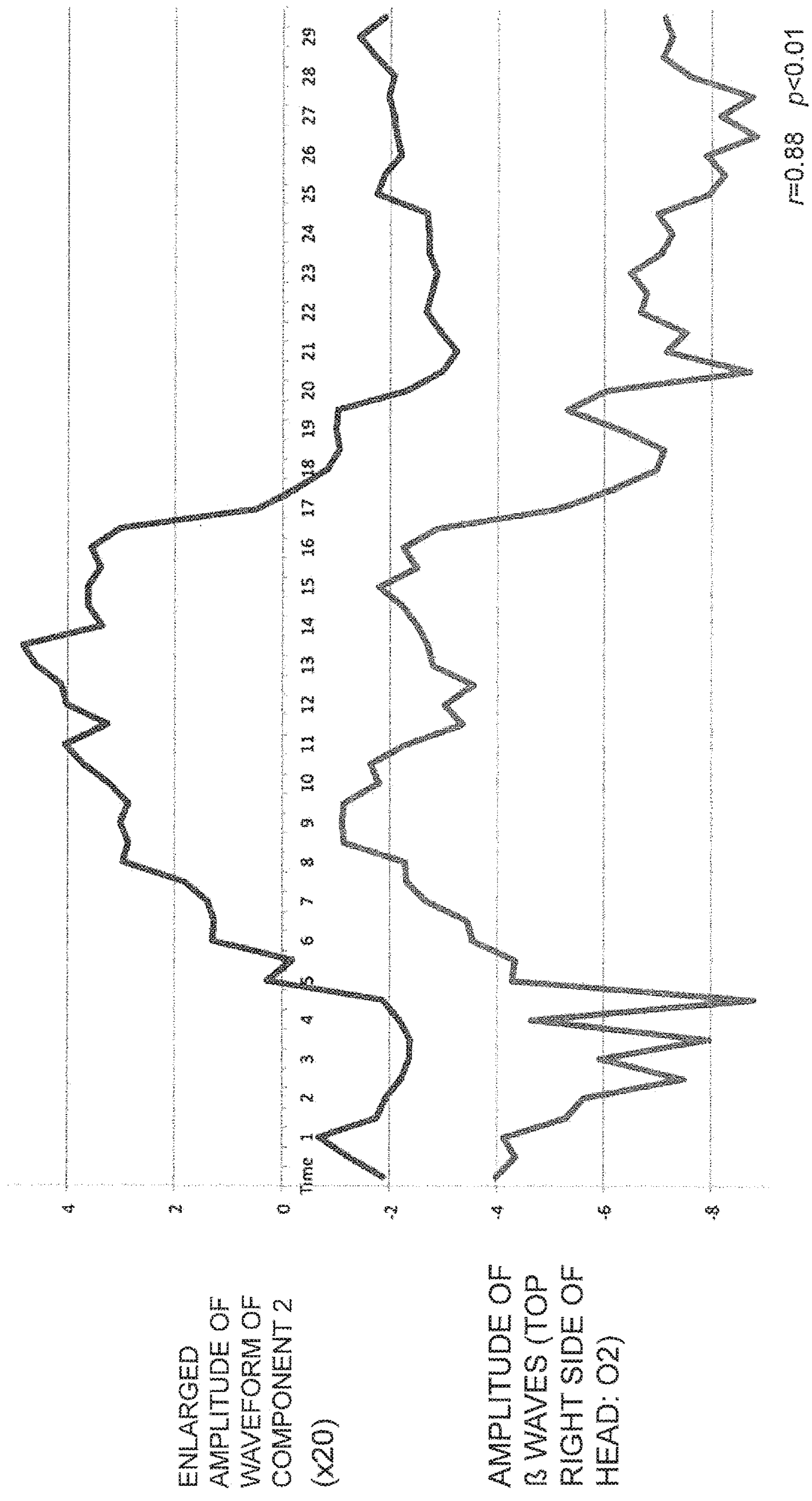
FIG. 10 is a diagram showing a component waveform based on facial skin temperature data and the amplitude of βwaves among measured brain waves.
Figure 11:
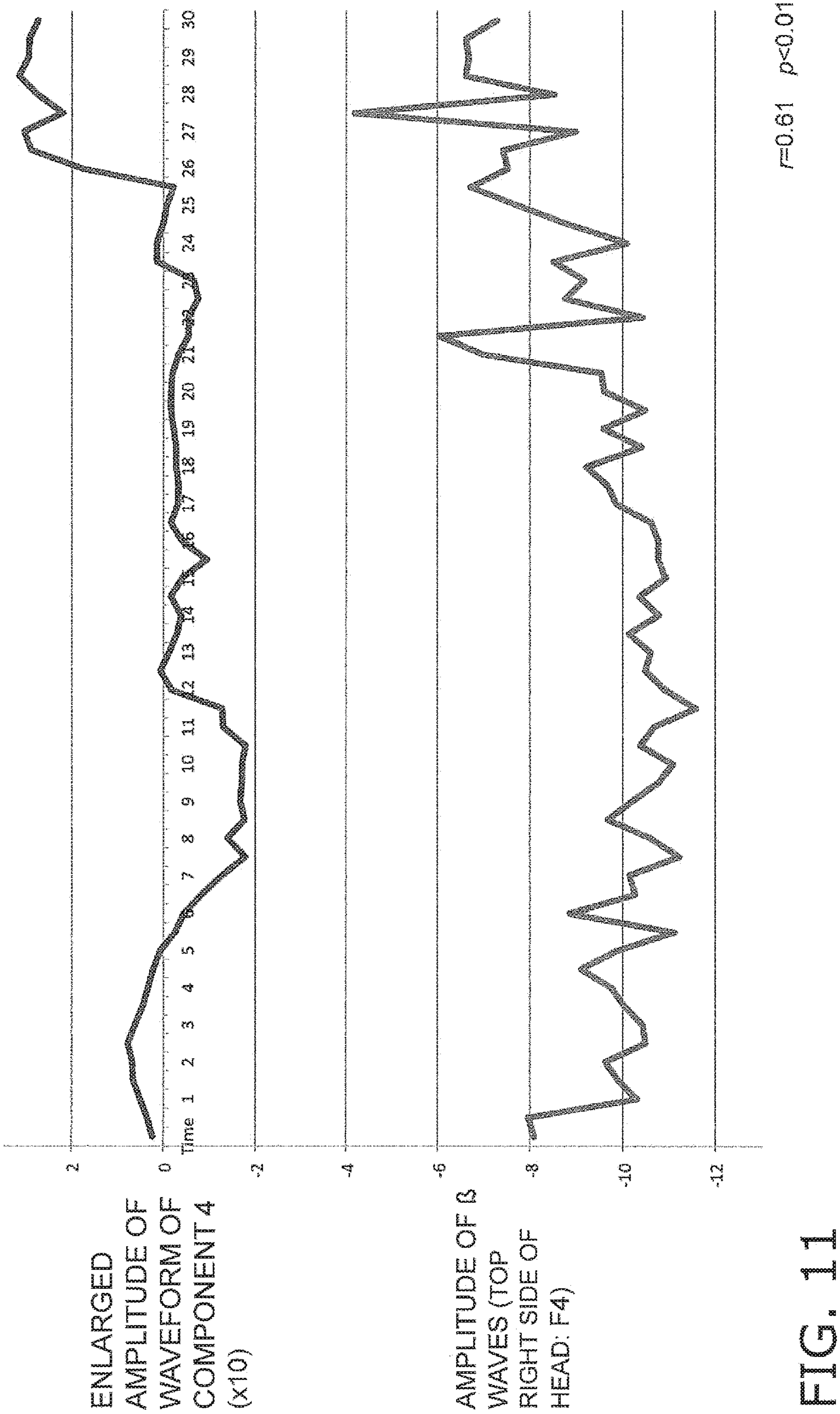
FIG. 11 is a diagram showing a component waveform based on photographed image data on a facial surface and the amplitude of βwaves among measured brain waves.
Figure 12:
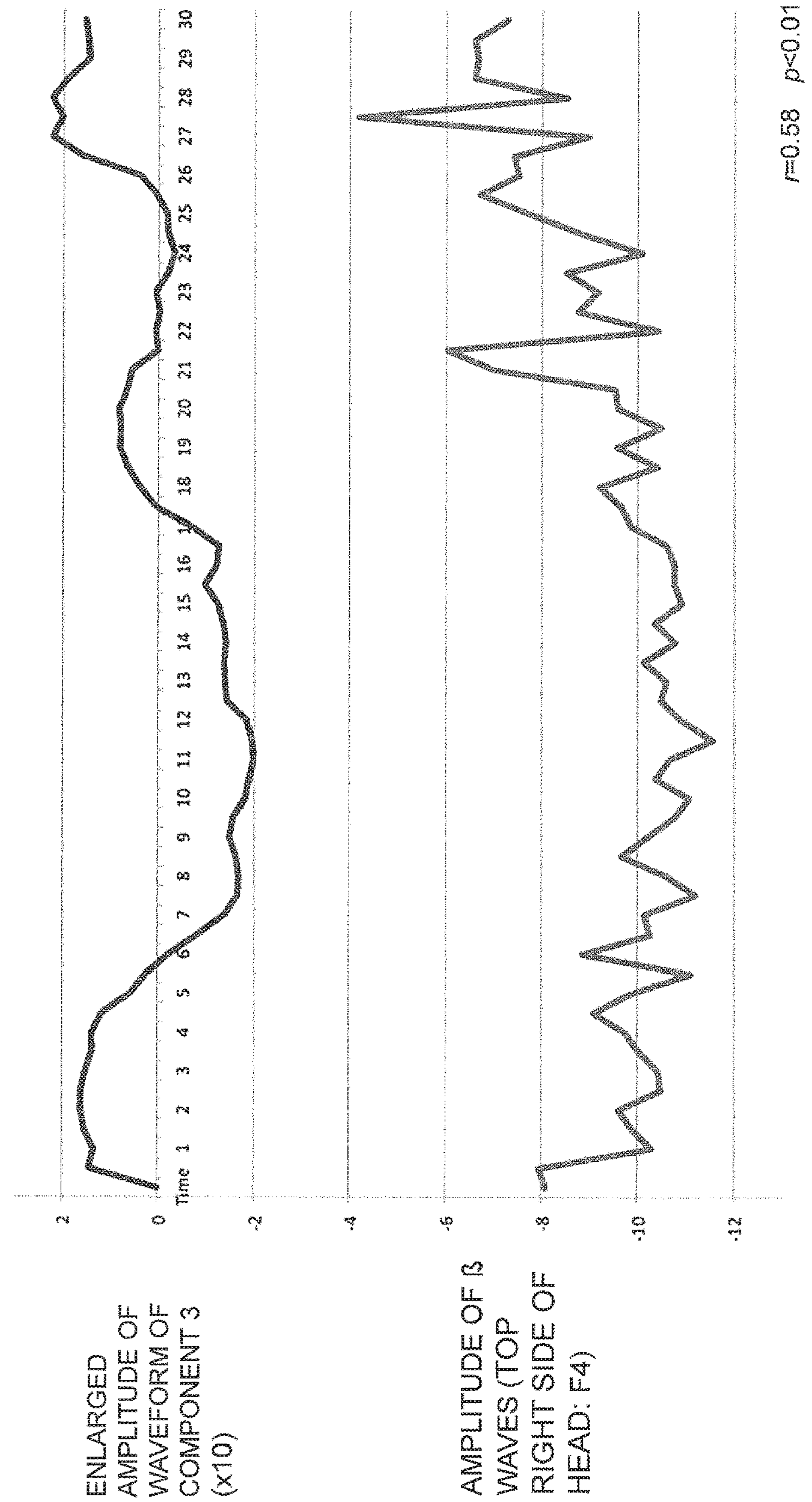
FIG. 12 is a diagram showing a component waveform based on facial skin temperature data and the amplitude of βwaves among measured brain waves.
Figure 13:
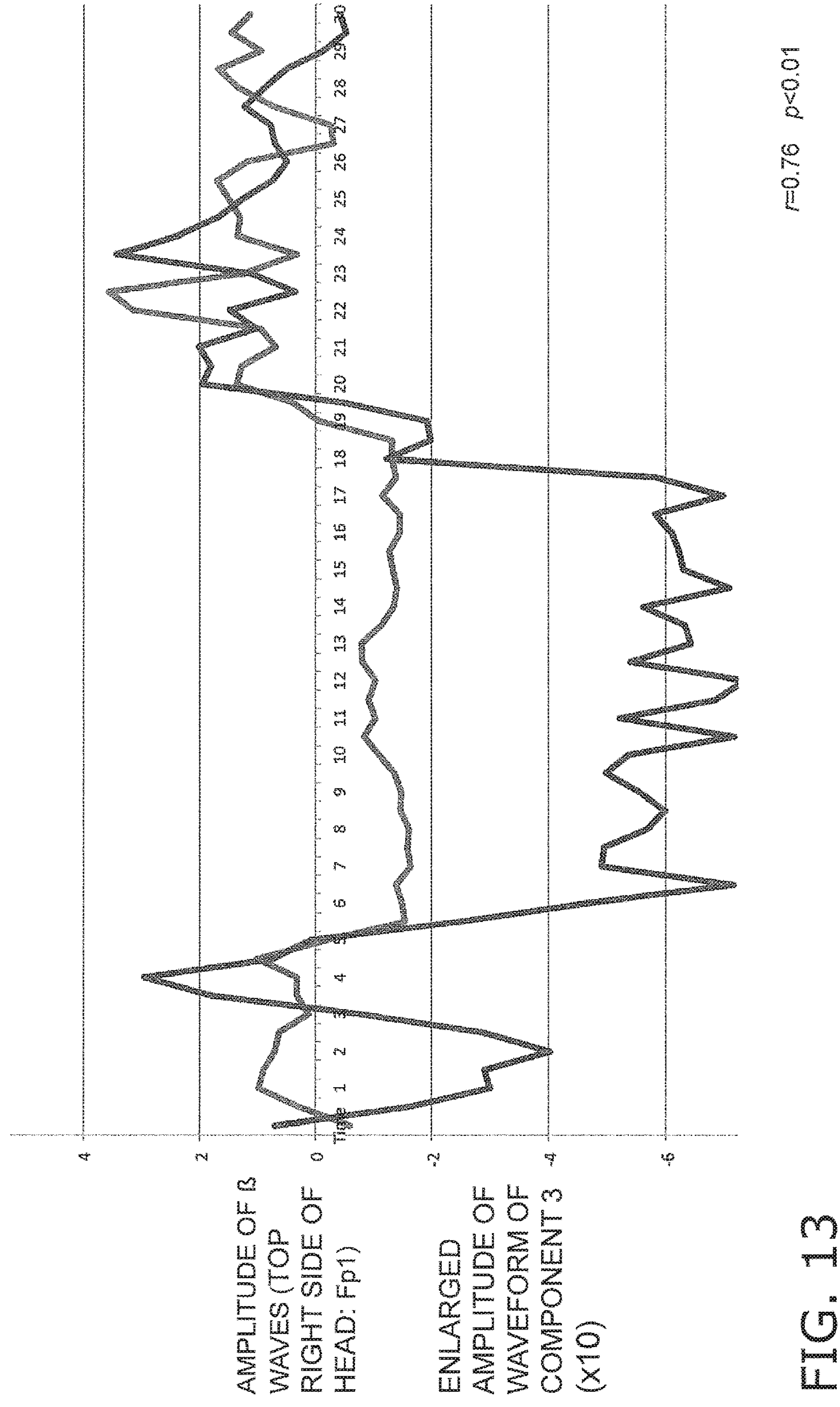
FIG. 13 is a diagram showing a component waveform based on photographed image data on a facial surface and the amplitude of βwaves among measured brain waves.
Figure 14:
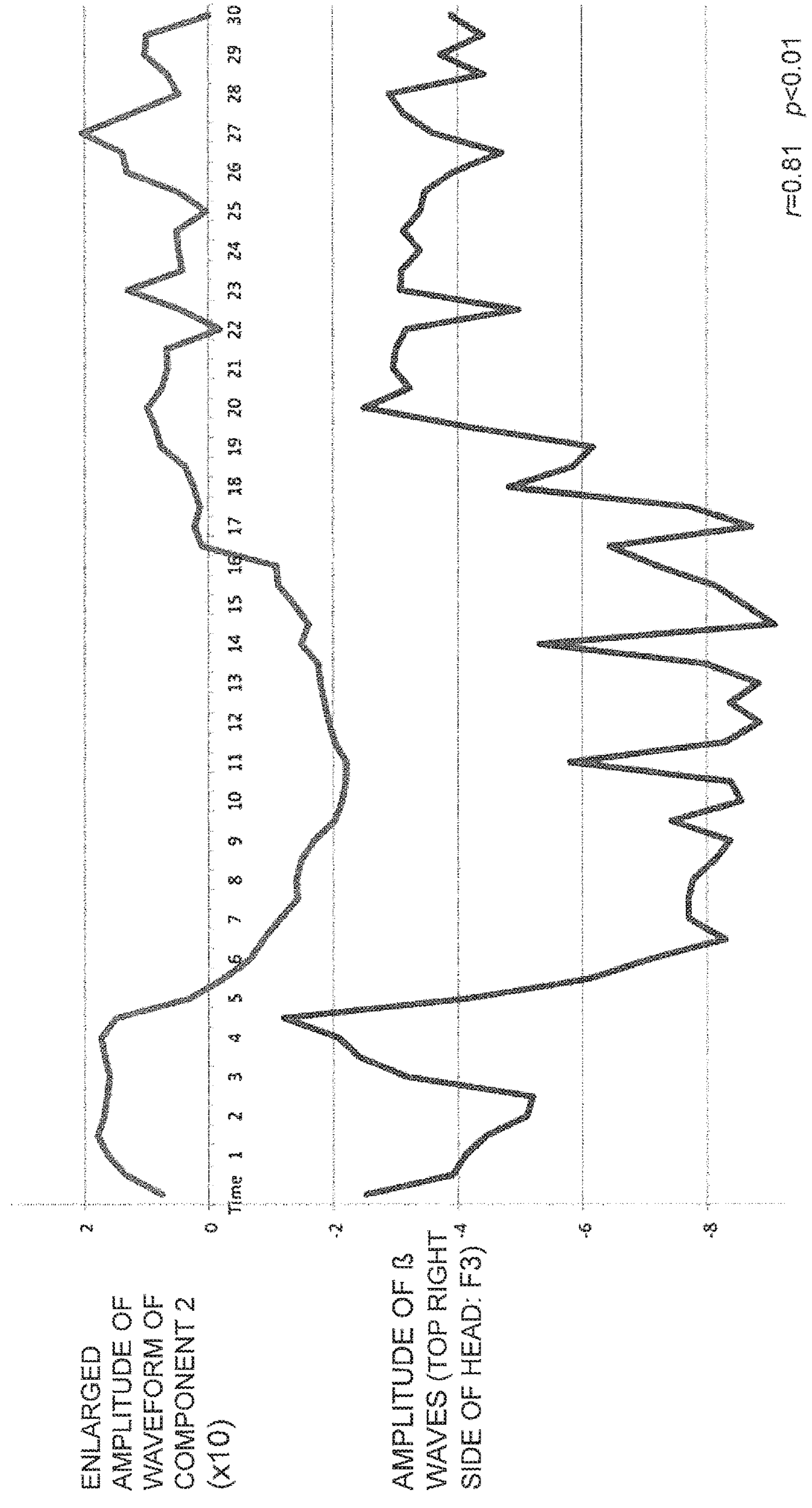
FIG. 14 is a diagram showing a component waveform based on facial skin temperature data and the amplitude of βwaves among measured brain waves.
Figure 15:
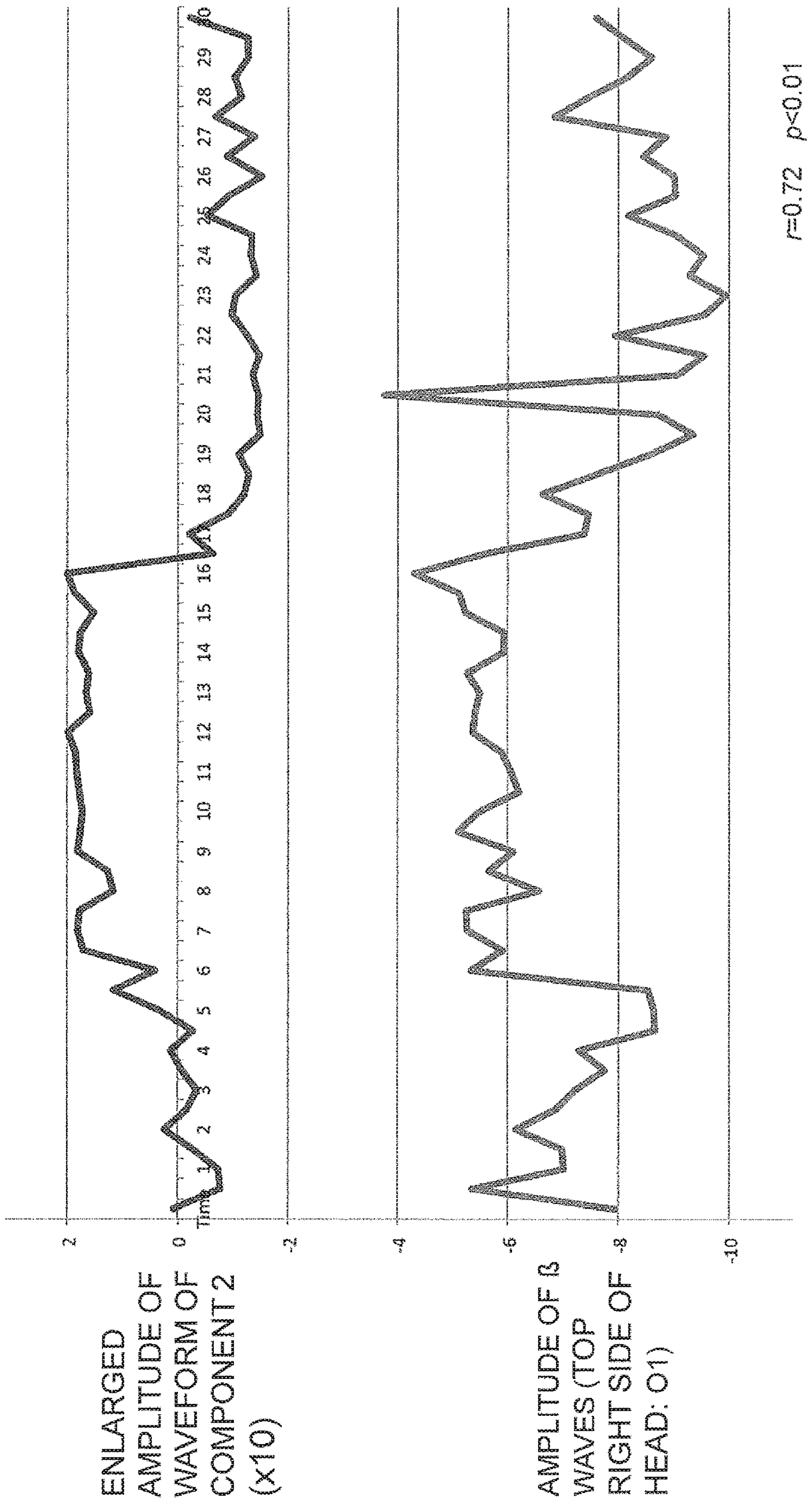
FIG. 15 is a diagram showing a component waveform based on photographed image data on a facial surface and the amplitude of βwaves among measured brain waves.
Figure 16:
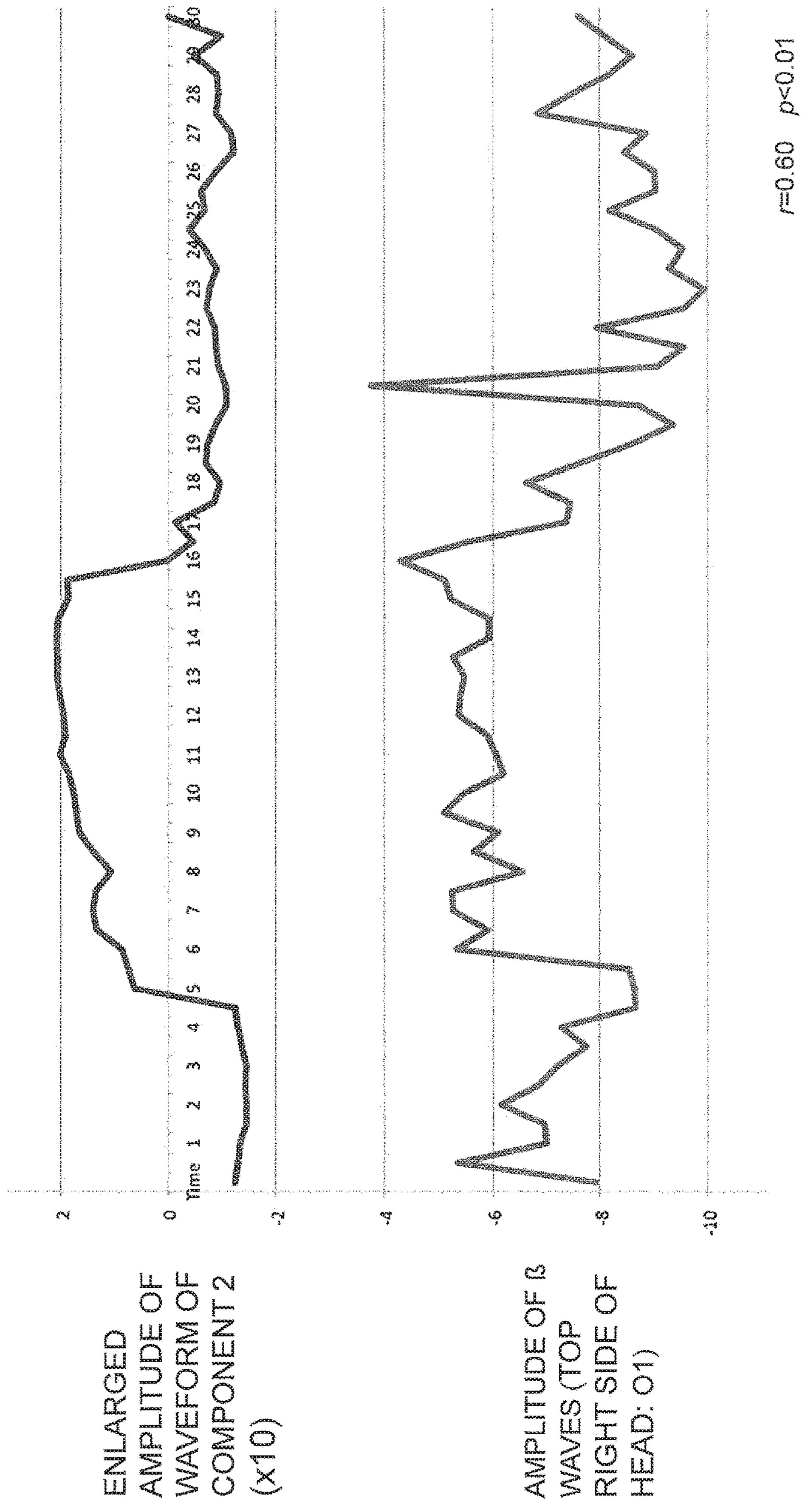
FIG. 16 is a diagram showing a component waveform based on facial skin temperature data and the amplitude of βwaves among measured brain waves.
Figure 17:
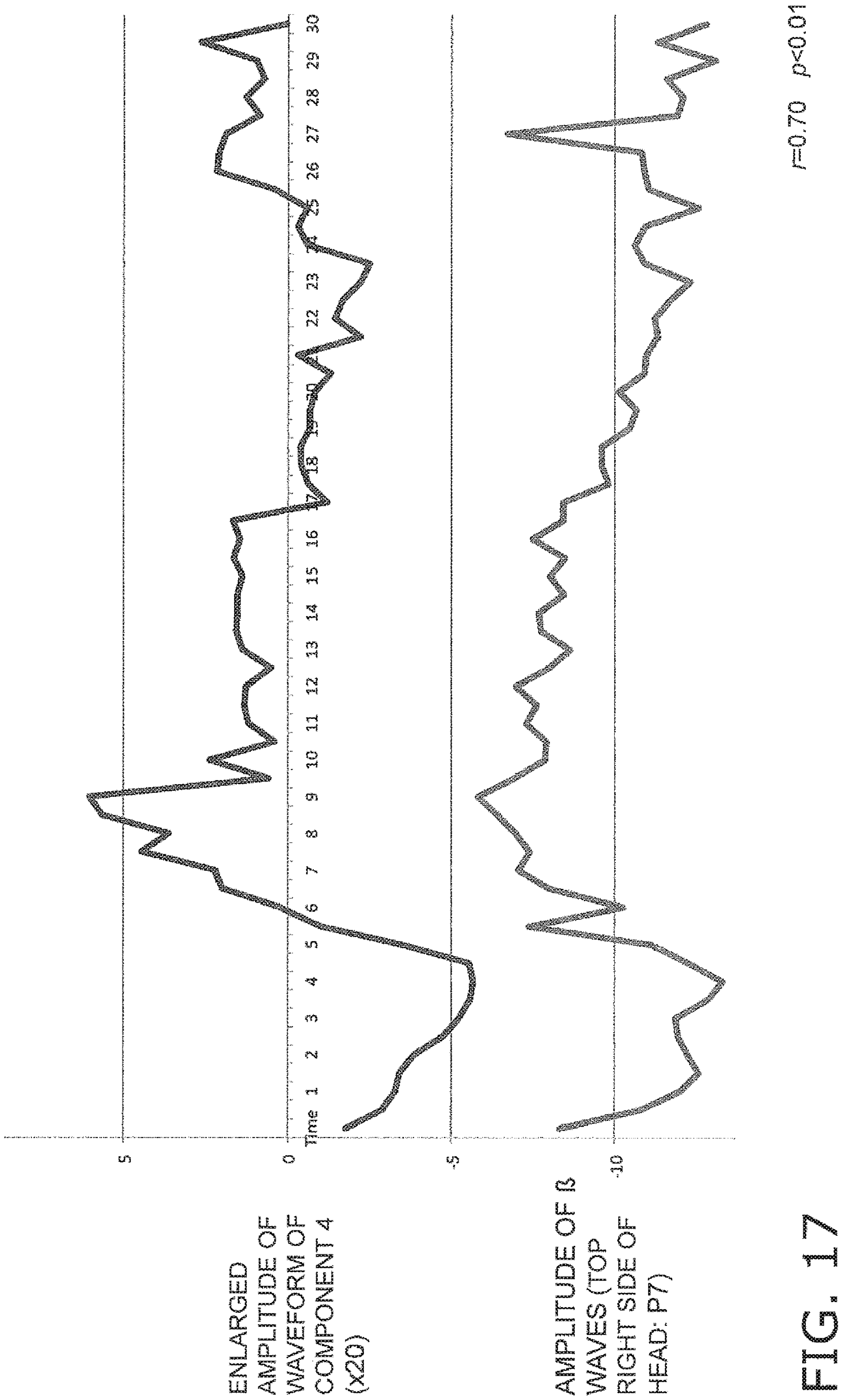
FIG. 17 is a diagram showing a component waveform based on photographed image data on a facial surface and the amplitude of βwaves among measured brain waves.
Figure 18:
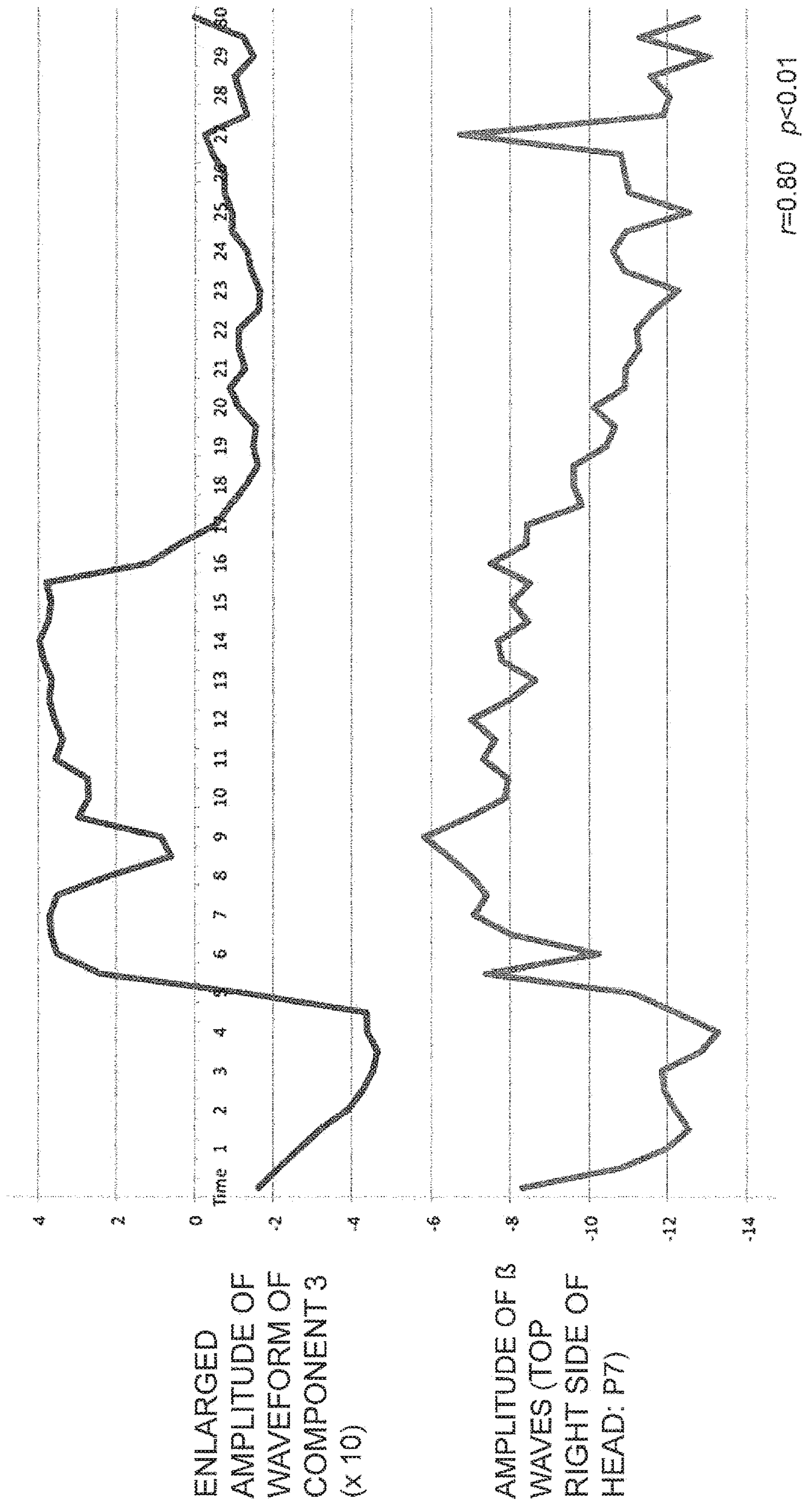
FIG. 18 is a diagram showing a component waveform based on facial skin temperature data and the amplitude of βwaves among measured brain waves.

FIGS. 7 to 18 are diagrams showing parts of comparison and analysis results of component waveform diagrams based on the photographed image data on the facial surface (blood-circulation-amount data) or the facial skin temperature data and waveform diagrams of the respective amplitudes of β waves among measured brain waves. FIG. 7 is a diagram showing the amplitude of a component waveform exhibited by the component 2 based on a photographed image data on the test subject 1 and the amplitude of β waves of the measured brain waves of the test subject 1. FIG. 8 is a diagram showing the amplitude of a component waveform exhibited by the component 2 based on the facial skin temperature data of the test subject 1 and the amplitude of β waves of the measured brain waves of the test subject 1. FIG. 9 is a diagram showing the amplitude of a component waveform exhibited by the component 2 based on a photographed image data on a test subject 2 and the amplitude of β waves of the measured brain waves of the test subject 2. FIG. 10 is a diagram showing the amplitude of a component waveform exhibited by the component 2 based on the facial skin temperature data of the test subject 2 and the amplitude of β waves of the measured brain waves of the test subject 2. FIG. 11 is a diagram showing the amplitude of a component waveform exhibited by the component 4 based on a photographed image data on a test subject 3 and the amplitude of β waves of the measured brain waves of the test subject 3. FIG. 12 is a diagram showing the amplitude of a component waveform exhibited by the component 3 based on the facial skin temperature data of the test subject 3 and the amplitude of β waves of the measured brain waves of the test subject 3. FIG. 13 is a diagram showing the amplitude of a component waveform exhibited by the component 3 based on a photographed image data on a test subject 4 and the amplitude of β waves among the measured brain waves of the test subject 4. FIG. 14 is a diagram showing the amplitude of a component waveform exhibited by the component 2 based on a facial skin temperature data on the test subject 4 and the amplitude of β waves of the measured brain waves of the test subject 4. FIG. 15 is a diagram showing the amplitude of a component waveform exhibited by the component 2 based on a photographed image data on a test subject 5 and the amplitude of β waves of the measured brain waves of the test subject 5. FIG. 16 is a diagram showing the amplitude of a component waveform exhibited by the component 2 based on the facial skin temperature data of the test subject 5 and the amplitude of β waves of the measured brain waves of the test subject 5. FIG. 17 is a diagram showing the amplitude of a component waveform exhibited by the component 4 based on a photographed image data on a test subject 6 and the amplitude of β waves of the measured brain waves of the test subject 6. FIG. 18 is a diagram showing the amplitude of a component waveform exhibited by the component 3 based on the facial skin temperature data of the test subject 6 and the amplitude of β waves of the measured brain waves of the test subject 6.

As shown in FIGS. 7 to 18, from the analysis results of each component waveform and the brain waves, the correlation was confirmed to be between the facial skin temperature and the facial blood circulation amount. Also in the analysis based on either of the facial skin temperature data and the facial blood-circulation-amount data, a significant correlation was confirmed between the amplitude of each component waveform and the amplitude of (i waves of the brain waves measured by the electrodes attached onto the head top or occipital region.

Table 2 below shows the analysis results of the photographed image data on the facial surface of each test subject.

TABLE 2

| | Correlation with the blood-circulation-amount data | | Correlation with relative conversion blood-circulation-amount data | |
|---|---|---|---|---|
| Test subject | Component waveform | Blood circulation amount distribution | Component wavelength | Blood circulation amount distribution |
| Test subject 1 | Component 2 | 0.72 | Component 1 | 0.59 |
| | | | Component 2 | 0.85 |
| Test subject 2 | Component 1 | 0.82 | Component 1 | 0.62 |
| | Component 2 | 0.82 | Component 2 | 0.60 |
| Test subject 3 | Component 2 | 0.33 | Component 2 | 0.45 |
| | Component 3 | 0.31 | Component 3 | 0.56 |
| | | | Component 4 | 0.56 |
| Test subject 4 | Component 1 | 0.57 | Component 1 | 0.66 |
| | Component 3 | 0.71 | Component 3 | 0.65 |

TABLE 2-continued

| | Correlation with the blood-circulation-amount data | | Correlation with relative conversion blood-circulation-amount data | |
|---|---|---|---|---|
| Test subject | Component waveform | Blood circulation amount distribution | Component wavelength | Blood circulation amount distribution |
| Test subject 5 | Component 1 | 0.56 | Component 1 | 0.51 |
| | Component 2 | 0.72 | Component 2 | 0.83 |
| Test subject 6 | Component 2 | 0.38 | Component 2 | 0.45 |
| | Component 4 | 0.68 | Component 3 | 0.51 |
| | | | Component 5 | 0.36 |

As shown in Table 2, from the results obtained by the analysis of the above-mentioned photographed image data, significant correlations were confirmed between the human brain activity and the components 1, 2, 3, 4, and 5 among a plurality of components obtained by decomposing the time-series blood-circulation-amount data based on the photographed image data on the facial surface by singular value decomposition. Here, the components identified as having the significant correlation with the human brain activity include, in addition to a component having the significant correlation therewith in terms of both the blood-circulation-amount data and the relative conversion blood-circulation-amount data, a component having the significant correlation therewith in terms of the relative conversion blood-circulation-amount data but not the blood-circulation-amount data.

Furthermore, Table 3 below shows the results of the control experiment.

TABLE 3

| | |
|---|---|
| Component having correlation with rest/activation of the brain | Component 1<br>Component 2 |
| Component having correlation with a moving distance of the facial surface | Component 1<br>Component 3<br>Component 4 |
| Component having correlation with the number of inputs into a keyboard | Component 8 |

As shown in Table 3, in the control experiment, when the test subject moved while acquiring a photographed image data on the facial surface, the component 2 was one of the components that had a significant correlation between the amplitude of its component waveform and each of the brain activation time and the brain non-activation time. However, the component 2 was not confirmed to have a significant correlation with each of the movement distance and the number of inputs into the keyboard. From this fact, it has been confirmed that among the components obtained by conducting the singular value decomposition on the blood-circulation-amount data based on the RGB data acquired from the photographed image data on the facial surface, the component having a significant correlation with the brain activity is hardly influenced by the movement of the test subject even if the test subject moves in acquiring the time-series photographed image data on the facial surface, as compared with the influence of the brain activity on the component (influence by the activation or non-activation of the brain).

From these results, the inventors have obtained the following findings.

The blood-circulation-amount data acquired from the facial RGB data based on the time-series photographed image data on the facial surface, acquired from the test subject, was decomposed into a plurality of components by the singular value decomposition, and then each of the decomposed components was analyzed. As a result of this analysis, the components 1, 2, 3, 4, and 5 among the plurality of components were confirmed to be related to the brain activity. That is, it has been found that the blood-circulation-amount data acquired from the facial RGB data based on the time-series photographed image data on the facial surface is decomposed into a plurality of components by the singular value decomposition, subsequently a component having a correlation with the activation/non-activation of the brain is extracted from the plurality of decomposed components, and then the extracted component is analyzed, so that the component indicative of the RGB change on the facial surface which reflects the brain activity can be identified from the plurality of components. Accordingly, the inventors have obtained the finding that the brain activity can be estimated based on the time-series photographed image data on the human's facial surface.

(4) Brain Activity Visualization Device

Next, a description will be given on brain activity visualization devices 10 and 110 according to an embodiment of the present invention that has completed by the inventors based on the findings described above. Note that the brain activity visualization device according to the present invention is not limited to the following embodiments, and various modifications and changes can be made to the embodiments without departing from the scope and spirit of the present invention.

Brain activity visualization devices 10 and 110 according to an embodiment of the present invention include a brain activity estimation means 30 for estimating the brain activity based on the facial skin temperature data and/or a brain activity estimation means 130 for estimating the brain activity based on the photographed image data on the facial surface. Hereinafter, first, the respective brain activity estimation means 30 and 130 will be described before explaining the brain activity visualization devices 10 and 110 according to the embodiment of the present invention.

Figure 19:
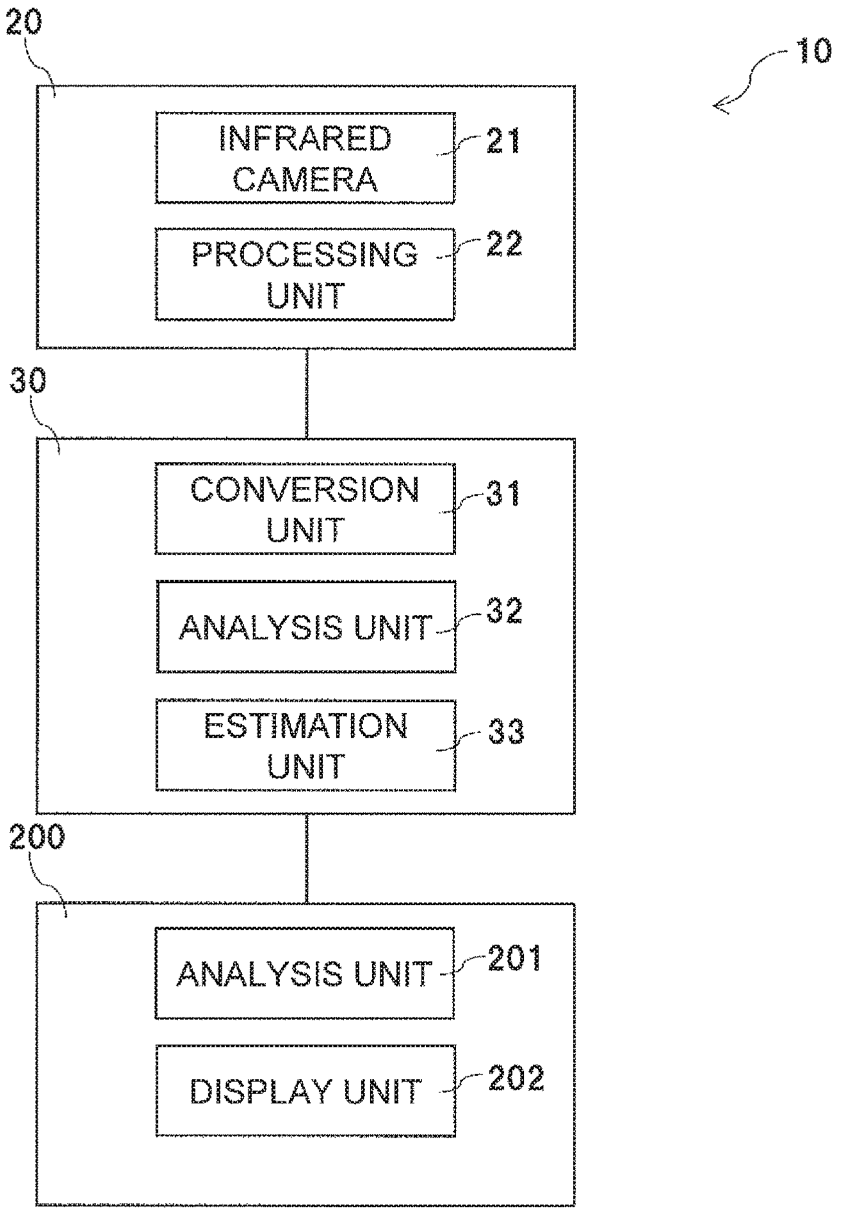
FIG. 19 is an exemplary diagram of a brain activity visualization device according to an embodiment of the present invention.
Figure 20:
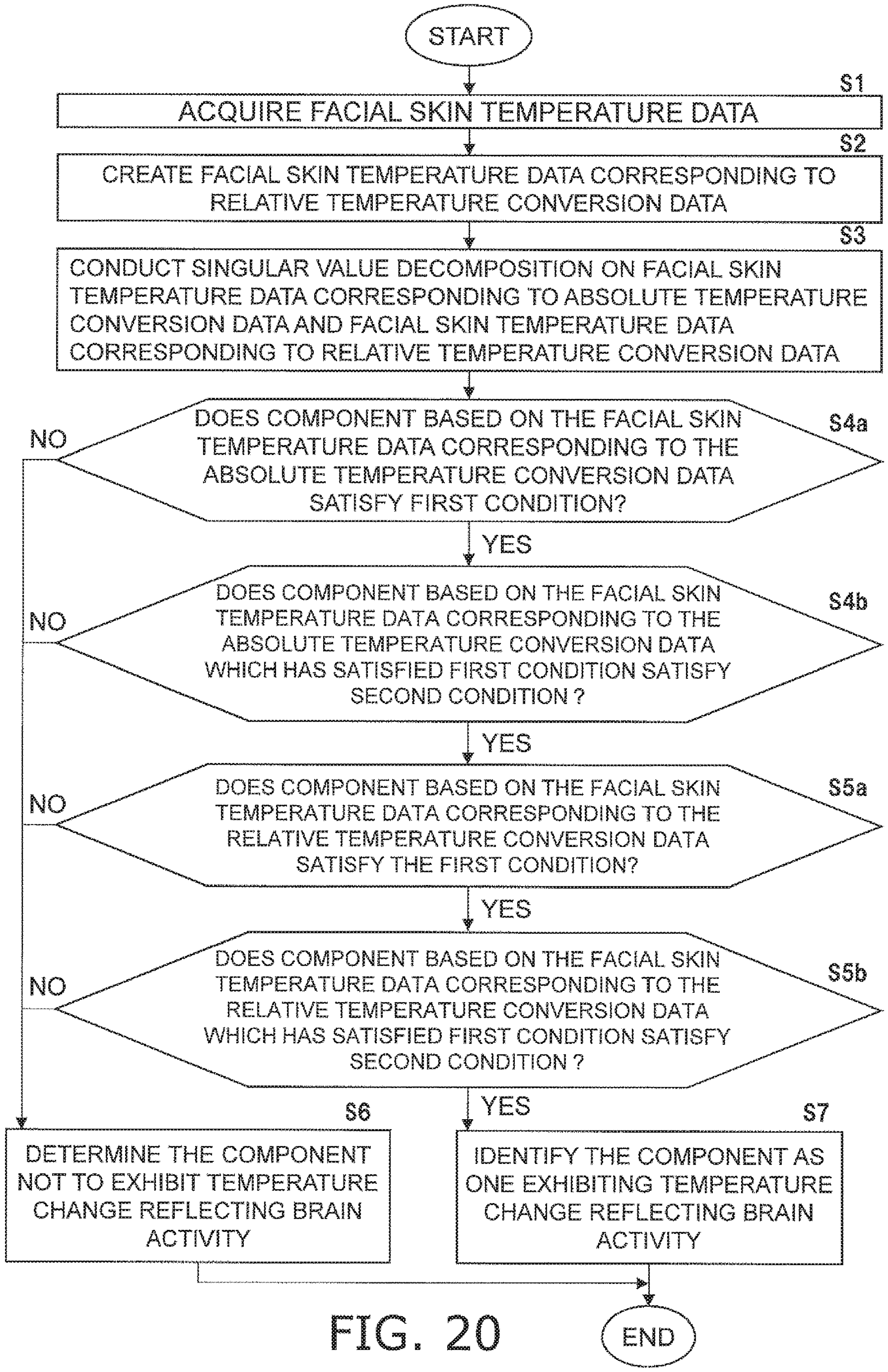
FIG. 20 is a flowchart showing a flow of processing performed in identifying a component indicative of a change in the skin temperature reflecting a brain function in the brain activity visualization device.

(4-1) Brain Activity Estimation Means 30 for Estimating the Brain Activity Based on the Facial Skin Temperature Data FIG. 19 is an exemplary diagram of a brain activity visualization device 10 according to an embodiment of the present invention. FIG. 20 is a flowchart showing the flow of processing performed in the case of identifying a component indicative of a change in the skin temperature that reflects the brain function in the brain activity visualization device 10.

The brain activity estimation means 30 included in the brain activity visualization device 10 estimates the brain activity of an individual (test subject) from the facial skin temperature of the individual. As shown in FIG. 19, the brain activity visualization device 10 includes facial skin temperature acquisition means 20, the brain activity estimation means 30, and state visualization means 200.

The facial skin temperature acquisition means 20 detects the skin temperature of at least a part of the facial surface of the individual, and acquires facial skin temperature data including the detected temperature data and position data regarding a detected part in time series (step S1). Here, the facial skin temperature acquisition means 20 is an infrared thermography device, and includes an infrared camera 21 and a processing unit 22, as shown in FIG. 19. The infrared camera 21 is for detecting infrared radiant energy emitted from the face of the individual. Here, it is assumed that the infrared camera 21 detects infrared radiant energy from the entire face of the individual. The processing unit 22 converts the infrared radiant energy detected by the infrared camera 21 into a corresponding temperature to create temperature data. Then, the processing unit 22 creates a temperature distribution diagram of the facial skin temperatures on the entire facial surface by assigning the parts at which the infrared radiant energy is detected to position data (coordinate data). Ultimately, the processing unit 22 processes the created temperature distribution diagram into facial skin temperature data corresponding to the temperature conversion data. The facial skin temperature data corresponding to the temperature conversion data is stored in a storage unit (not shown) included in the processing unit 22.

Here, the processing unit 22 creates the temperature distribution diagram of the facial skin temperatures across the entire facial surface, but is not limited thereto. Alternatively, the temperature distribution diagram of the temperature of the facial skin including at least the paranasal sinus peripheral region and/or forehead may be created, and this diagram may be handled as the facial skin temperature data corresponding to the temperature conversion data.

Here, while the facial skin temperature data corresponding to the temperature conversion data is being acquired by the facial skin temperature acquisition means 20, the brain function activation task is given to the individual for a certain period of time. That is, the facial skin temperature data corresponding to the temperature conversion data acquired by the facial skin temperature acquisition means 20 includes the data generated for a time period during which the brain function activation task is given to the individual. Note that the brain function activation task given to the individual is not particularly limited as long as it is estimated to bring the brain into the activated state. For example, the brain function activation task may be configured to have its contents determined as appropriate in accordance with the purpose of use of the brain activity visualization device 10.

The brain activity estimation means 30 estimates the human brain activity based on the facial skin temperature data corresponding to the temperature conversion data acquired by the facial skin temperature acquisition means 20. Specifically, as shown in FIG. 19, the brain activity estimation means 30 includes a conversion unit 31, an analysis unit 32, and an estimation unit 33.

The conversion unit 31 converts the temperature data included in the facial skin temperature data corresponding to the temperature conversion data, into relative temperature data, and generates facial skin temperature data based on the converted relative temperature data, that is, facial skin temperature data corresponding to the relative temperature conversion data (step S2). Specifically, the conversion unit 31 sets an average value of the temperature data included in the facial skin temperature data corresponding to the temperature conversion data every predetermined time (for example, 30 seconds) as a reference value, and then converts the temperature data into the relative temperature data. The conversion unit 31 generates the facial skin temperature data corresponding to the relative temperature data by using the converted relative temperature data and the position data.

The analysis unit 32 decomposes each of the facial skin temperature data corresponding to the time-series temperature conversion data and the facial skin temperature data corresponding to the relative temperature conversion data, into a plurality of components by the singular value decomposition, principal component analysis, or independent component analysis (step S3). Here, the analysis unit 32 conducts the singular value decomposition on the acquired facial skin temperature data corresponding to the temperature conversion data as well as the converted facial skin temperature data corresponding to the relative temperature conversion data, by using the SVD of MATLAB (registered trademark) as the analysis tool. In the singular value decomposition, for the facial skin temperature data corresponding to the temperature conversion data acquired in time series as well as the facial skin temperature data corresponding to the relative temperature conversion data, the factor was defined as time data acquired every predetermined time period (for example, 30 seconds), and the measure was defined as the facial skin temperature data corresponding to the temperature conversion data in that time period and the facial skin temperature data corresponding to the relative temperature conversion data. By the singular value decomposition, each of the facial skin temperature data corresponding to the temperature conversion data and the facial skin temperature data corresponding to the relative temperature conversion data was decomposed into a plurality of components, and then a time distribution and a space distribution of each component and a singular value indicative of the size of each component were calculated.

Further, the analysis unit 32 determines whether or not each component satisfies a first condition and a second condition in order to identify the component indicative of the change in the skin temperature that reflects the brain activity, from the plurality of components decomposed by the singular value decomposition (step S4*a*, step S4*b*, step S5*a*, and step S5*b*). Here, first, the analysis unit 32 determines whether the first condition is satisfied by each of the components based on the facial skin temperature data corresponding to the temperature conversion data (step S4*a*). Then, it is determined whether the second condition is satisfied by the component based on the facial skin temperature data corresponding to the temperature conversion data which has been determined to satisfy the first condition in step S4*a* (step S4*b*). Subsequently, it is determined whether or not the first condition is satisfied by only a component(s) that is identical to a component(s) determined to satisfy both the first and second conditions in steps S4*a* and S4*b*, among respective components based on the facial skin temperature data corresponding to the relative temperature conversion data (step S5*a*). Then, it is determined whether the second condition is satisfied by the component based on the facial skin temperature data corresponding to the relative temperature conversion data and which has been determined to satisfy the first condition in step S5*a* (step S5*b*). Note that the order of the determination conducted by the analysis unit 32 is not limited thereto. Alternatively, for example, it is determined whether or not each component based on the facial skin temperature data corresponding to the temperature conversion data as well as each component based on the facial skin temperature data corresponding to the relative temperature conversion data satisfy the first condition and the second condition respectively, and finally the components whose determination results are identical to each other may be extracted.

The first condition is that the amplitude of the component waveform of a component obtained by the singular value decomposition has a correlation with changes of the brain in the non-activation time and the activation time. The analysis unit 32 extracts the component satisfying the first condition as a determination component from the plurality of components. Here, while the facial skin temperature data corresponding to the temperature conversion data is being acquired, the brain function activation task is given to the individual for a certain time period. The analysis unit 32 defines a time period during which the brain function activation task is not given to the individual as the brain non-activation time, and also defines a time period during which the brain function activation task is given to the individual as the brain activation time. Then, the analysis unit 32 compares the component waveform of each component with each of the brain non-activation time and the brain activation time. The analysis unit 32 evaluates whether or not there is a correlation between the component waveform of each component and each of the brain non-activation time and the brain activation time, using the comparison analysis results based on the component waveform data. Then, the analysis unit 32 extracts the component which has been evaluated to have a correlation, from the plurality of components as a determination component satisfying the first condition. Meanwhile, the analysis unit 32 evaluates that a component(s) among the plurality of components does not have any correlation. Then, the analysis unit 32 determines the evaluated component not to exhibit the temperature change reflecting the human brain activity while not satisfying the first condition (step S6).

Here, the brain function activation task is given to the individual for a certain period of time in acquiring the facial skin temperature data corresponding to the temperature conversion data. Based on this result, the analysis unit 32 extracts a determination component. However, the contents of the first condition, i.e., the extraction means of the determination component in the analysis unit 32 are not limited thereto. For example, when a component that exhibits the component waveform having a correlation with the brain non-activation time and the brain activation time is specified from among the plurality of components by conducting experiments or the like in advance, the analysis unit 32 extracts the specified component from the plurality of components as the determination component. In addition, when a human's movement known to be related to the activation/non-activation of the brain, such as eye movement or blink, is detected on the present brain activity visualization device, the analysis unit 32 may compare, analyze, and evaluate the detection result and the component waveform of each component, thereby extracting the determination component from the plurality of components. Note that the criterion for the analysis unit 32 to determine whether the first condition is satisfied or not is decided as appropriate by simulation, experiments, desk calculation, or the like in accordance with the purpose of use of the brain activity visualization device 10 or the like.

The second condition is that regarding the extracted determination component, there is a temperature change in a predetermined part on the human's facial surface. The analysis unit 32 determines a component satisfying the second condition among the determination components as a component having a high possibility of being related to the human brain activity, and extracts this component as a candidate component. That is, the analysis unit 32 determines whether or not the determination component is related to the human brain activity based on the presence or absence of a temperature change in a predetermined part of the human's facial surface. Specifically, the analysis unit 32 determines whether or not a temperature change occurs in the paranasal sinus peripheral region and/or the forehead based on the temperature distribution data regarding the extracted determination component. Then, if the temperature change occurs there, the analysis unit 32 determines that the determination component is a component that satisfies the second condition and which has a high possibility of being related to human brain activity, and extracts this component as a candidate component. On the other hand, when the temperature change does not occur in the paranasal sinus peripheral region and/or the forehead, the analysis unit 32 determines that the determination component does not satisfy the second condition and does not exhibit a change in the skin temperature that reflects the brain activity (step S6). Note that the criterion for the analysis unit 32 to determine whether the second condition is satisfied or not is determined as appropriate by simulation, experiments, desk calculation, or the like in accordance with the purpose of use of the brain activity visualization device 10 or the like.

Then, the analysis unit 32 identifies the component determined to satisfy the second condition in step S5*b* as a component indicative of the change in the skin temperature reflecting the brain activity (step S7). That is, the component identified as the component reflecting the brain activity and indicating the change in the skin temperature in step S7 achieves the fact that the candidate component extracted by decomposing and analyzing the facial skin temperature data corresponding to the temperature conversion data by singular value decomposition is identical to the candidate component extracted by decomposing and analyzing the facial skin temperature data corresponding to the relative temperature conversion data by the singular value decomposition. It should be noted that the candidate components which are extracted in both analysis steps and are not identical with each other are determined not to indicate the change in the skin temperature reflecting the brain activity in step S6.

The estimation unit 33 estimates the human brain activity based on the component identified by the analysis unit 32 as the component indicative of the change in the skin temperature reflecting the human brain activity. Specifically, the estimation unit 33 estimates an amount of brain activity when the facial skin temperature data is acquired based on the component waveform data regarding the component identified by the analysis unit 32.

(4-1-1) Modified Example 1A

The brain activity estimation means 30 includes a conversion unit 31, and generates the facial skin temperature data corresponding to the relative temperature conversion data by the conversion unit 31. The analysis unit 32 decomposes not only the facial skin temperature data corresponding to the temperature conversion data acquired by the facial skin temperature acquisition means 20, but also the facial skin temperature data corresponding to the relative temperature data based on the temperature data converted to the relative temperature data, into a plurality of components by the singular value decomposition. Then, the analysis unit 32 analyzes these decomposed respective components.

Instead of this, the brain activity estimation means 30 may not include the conversion unit 31. In this case, the elimination of the conversion unit 31 makes it possible to omit the processing of generating the facial skin temperature data corresponding to the relative temperature conversion data or analyzing the data based on the facial skin temperature data corresponding to the relative temperature conversion data.

To identify the component related to the human brain activity with high accuracy, however, it is desirable that the brain activity estimation means 30 includes the conversion unit 31, like the above-mentioned embodiment. Furthermore, the analysis unit 32 decomposes the facial skin temperature data corresponding to the temperature conversion data acquired by the facial skin temperature acquisition means 20 and also decomposes the facial skin temperature data corresponding to the relative temperature data based on the temperature data converted to the relative temperature data, into a plurality of components by the singular value decomposition. In addition, the analysis unit 32 analyzes these decomposed components.

(4-1-2) Modified Example 1B

The facial skin temperature acquisition means 20 is an infrared thermography device capable of acquiring the temperature data in a non-contact state with an object.

However, the facial skin temperature acquisition means is not limited to the infrared thermography device as long as this means can detect the skin temperature of at least a part of the individual's facial surface and can acquire the facial skin temperature data including the detected temperature data and the position data on the detected part in time series.

For example, the facial skin temperature acquisition means may be a device including a temperature sensor. Specifically, a temperature sensor may be attached to a predetermined part of an individual's facial surface, and time-series facial skin temperature data may be acquired based on temperature data detected by the temperature sensor and position data of the part where the temperature sensor is attached. In this way, the temperature sensor does not require preprocessing before attachment, unlike brain wave electrodes or the like, even when the facial skin temperature data is acquired with the temperature sensor being in contact with a target individual. Thus, the temperature sensor can easily acquire the data, as compared with conventional detection methods, such as an electroencephalography method, a magnetic resonance imaging method, and a near infrared spectroscopy method. Consequently, the human brain activity can be easily estimated.

Figure 21:
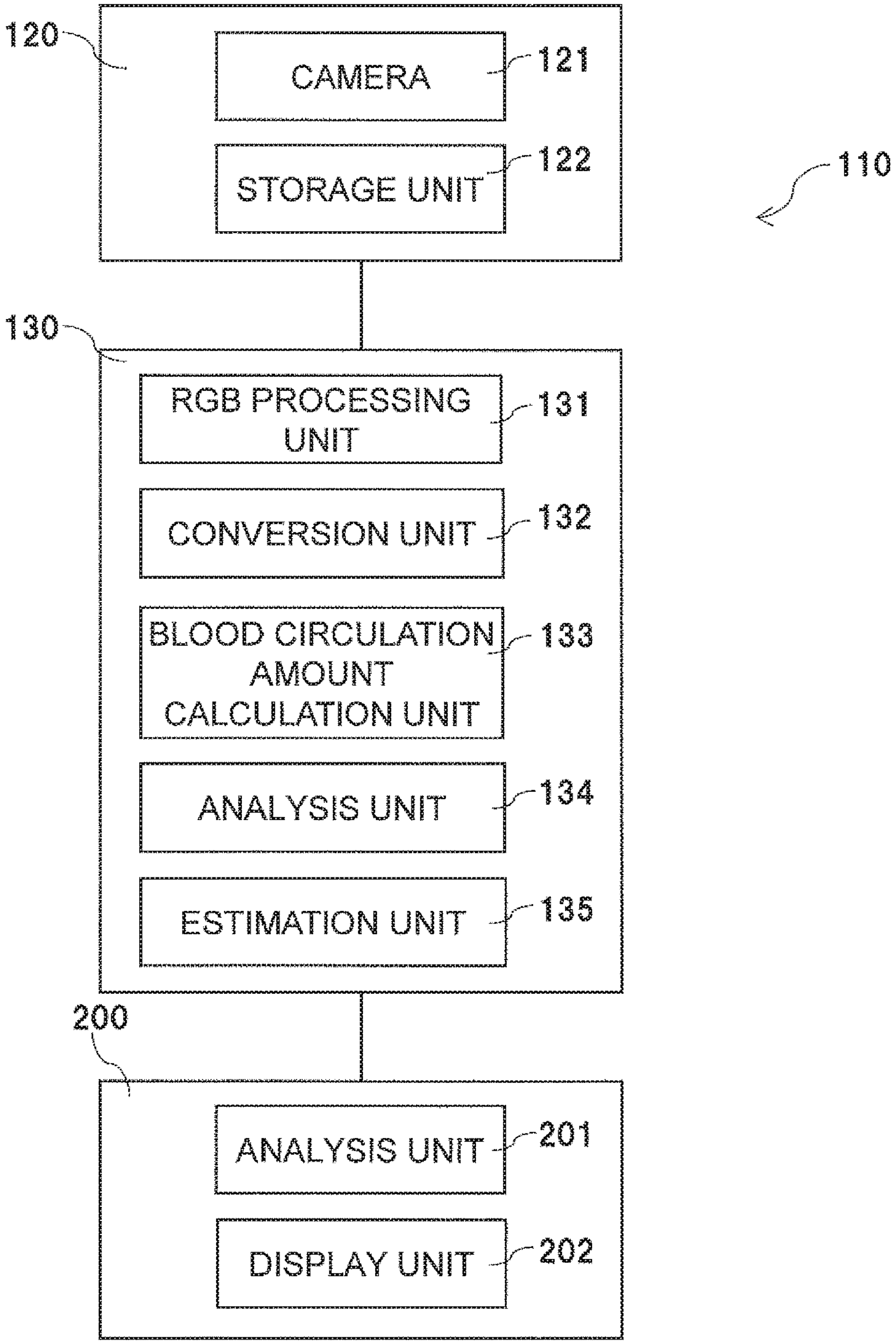
FIG. 21 is an exemplary diagram of a brain activity visualization device according to an embodiment of the present invention.
Figure 22:
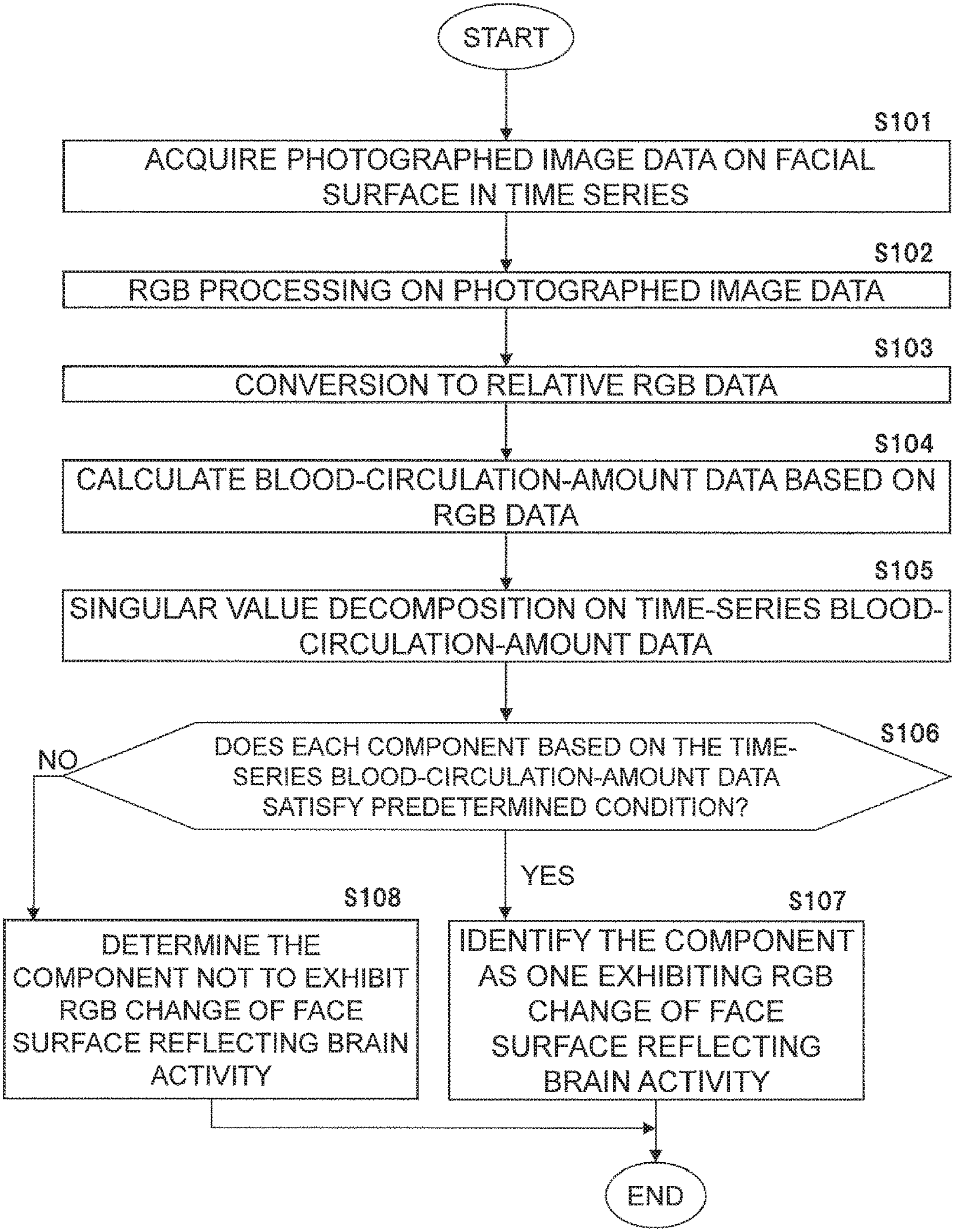
FIG. 22 is a flowchart showing an example of the flow of processing performed in identifying a component indicative of an RGB change on a facial surface reflecting a brain function in the brain activity visualization device.

(4-2) Brain Activity Estimation Means 130 for Estimating the Brain Activity Based on the Photographed Image Data on the Facial Surface FIG. 21 is an exemplary diagram of the brain activity visualization device 110 according to an embodiment of the present invention. FIG. 22 is a flowchart showing an example of the flow of processing performed when a component indicative of an RGB change on a facial surface reflecting a brain function is identified in the brain activity visualization device 110.

The brain activity estimation means 130 included in the brain activity visualization device 110 is a device for estimating the brain activity of an individual (test subject) from the photographed image data on the individual's facial surface. As shown in FIG. 21, the brain activity visualization device 110 includes image data acquisition means 120, the brain activity estimation means 130, and state visualization means 200.

The image data acquisition means 120 acquires the photographed image data on at least a part of the individual's facial surface in time series (step S101). The image data acquisition means 120 is not particularly limited as long as it has at least an imaging device. The image data acquisition means 120 can be, for example, a portable terminal incorporated therein an imaging device, such as a smartphone or a tablet (for example, iPad: registered trademark). Here, as shown in FIG. 21, the image data acquisition means 120 includes a camera 121 as the imaging device and a storage unit 122. The camera 121 is to acquire photographed image data on an individual's facial surface in time series. Here, the camera 121 photographs a moving image of the entire facial surface of an individual, and acquires photographed moving image data. The storage unit 122 stores therein the time-series photographed image data photographed by the imaging device. Here, the storage unit 122 stores therein the moving image data acquired by the camera 121.

Although here, the moving image of the entire facial surface is photographed by the camera 121, the moving image is not limited to this range. Alternatively, a moving image including an image of at least the forehead and/or the paranasal sinus peripheral region of the facial surface only needs to be photographed.

Here, while the time-series photographed image data on the facial surface is being acquired by the image data acquisition means 120, the brain function activation task is given to the individual for a certain period of time. That is, the photographed image data acquired by the image data acquisition means 120 inevitably includes data provided for a period of time during which the brain function activation task is given to the individual. Note that the brain function activation task given to the individual is not particularly limited as long as it is estimated to bring the brain into the activated state. For example, the brain function activation task may be configured to have its contents determined as appropriate in accordance with the purpose of use of the brain activity visualization device 110.

The brain activity estimation means 130 estimates the human brain activity based on the time-series photographed image data regarding the facial surface acquired by the image data acquisition means 120. Specifically, as shown in FIG. 21, the brain activity estimation means 130 includes an RGB processing unit 131, a conversion unit 132, a blood circulation amount calculating unit 133, an analysis unit 134, and an estimation unit 135. FIG. 21 shows an embodiment in which the brain activity estimation means 130 is configured as one device that includes the RGB processing unit 131, the conversion unit 132, the blood circulation amount calculating unit 133, the analysis unit 134, and the estimation unit 135. However, the present invention is not limited thereto. Alternatively, a part(s) or each of the RGB processing unit 131, the conversion unit 132, the blood circulation amount calculating unit 133, the analysis unit 134, and the estimation unit 135 may be configured as an independent device. Here, the image data acquisition means 120, the RGB processing unit 131, the conversion unit 132, and the blood circulation amount calculating unit 133 constitute the facial blood circulation amount acquisition means.

The RGB processing unit 131 conducts the RGB processing for decomposing the photographed image data acquired by the image data acquisition means 120, into three color components composed of an R component, a G component, and a B component (step S102). Here, although the RGB processing may be conducted on the photographed image data on the entire facial surface, in order to reduce the amount of computation processing and noise, data on the forehead and/or the paranasal sinus peripheral region is extracted from the photographed image data, and then the RGB processing is conducted only on the extracted data.

The conversion unit 132 converts the RGB data, acquired from the photographed image data by the RGB processing, into relative RGB data (step S103). Specifically, the conversion unit 132 sets an average value of the RGB data obtained from the photographed image data acquired every predetermined time (for example, 30 seconds) as a reference value, and then converts the RGB data to the relative RGB data.

The blood circulation amount calculating unit 133 calculates the time-series facial blood-circulation-amount data based on the RGB data acquired from the photographed image data by the RGB processing (step S104).

The analysis unit 134 decomposes the time-series relative-conversion blood-circulation-amount data into a plurality of components by the singular value decomposition, principal component analysis, or independent component analysis (step S105). Here, the analysis unit 134 conducts the singular value decomposition on the relative-conversion blood-circulation-amount data using the SVD of MATLAB (registered trademark) as the analysis tool. Specifically, in the singular value decomposition, the target is defined as the time-series relative-conversion blood-circulation-amount data, the factor is defined as time data acquired every predetermined time period (for example, 30 seconds), and the measure is defined as the relative-conversion blood-circulation-amount data for each pixel that is computed from the relative RGB data acquired every predetermined time period. By the singular value decomposition, the time-series relative-conversion blood-circulation-amount data is decomposed into a plurality of components, and then a time distribution, a space distribution, and a singular value indicative of the size of each component are calculated.

The analysis unit 134 determines whether or not each component satisfies a predetermined condition in order to identify the component indicative of the RGB change on the facial surface reflecting the brain activity, from among the plurality of components obtained by the singular value decomposition (step S106). Here, the predetermined condition includes, for example, a condition in which the amplitude of the component waveform of the component obtained by the singular value decomposition has a correlation with changes of the brain in the non-activation time and the activation time (hereinafter referred to as the first condition), a condition in which the component obtained by the singular value decomposition has a change in the blood circulation amount at a predetermined part on the human's facial surface (hereinafter referred to as the second condition), and the like. The predetermined condition based on which the determination is made by the analysis unit 134 may include one or a plurality of preset conditions, and here, it is assumed that the first condition is set as the predetermined condition.

The analysis unit 134 extracts components satisfying the predetermined condition as a determination component from the plurality of components. Subsequently, the analysis unit 134 identifies a component(s) satisfying all the conditions included in the predetermined condition among the extracted determination components, as a component(s) indicative of the RGB change on the facial surface reflecting the brain activity (step S107). Meanwhile, the analysis unit 134 determines that a component(s) determined not to satisfy at least one of the conditions included in the predetermined condition among the extracted determination components, is not a component(s) indicating the RGB change on the facial surface reflecting the brain activity (step S108).

Here, as mentioned above, only one condition (the first condition) is set as the predetermined condition. While the time-series photographed image data on the facial surface is being acquired, there is a certain period of time during which the brain function activation task is given to the individual. The analysis unit 134 defines a time period during which the brain function activation task is not given to the individual as the brain non-activation time, and also defines a time period during which the brain function activation task is given to the individual as the brain activation time. Then, the analysis unit 134 compares and analyzes the component waveform of each component with each of the brain non-activation time and the brain activation time. The analysis unit 134 evaluates whether or not there is a correlation between the component waveform of each component and each of the brain non-activation time and the brain activation time, using the comparison analysis result based on the component waveform data. Then, the analysis unit 134 extracts the component(s) evaluated to have a correlation, from the plurality of components as a determination component that satisfies a predetermined condition, and identifies this component as a component exhibiting the RGB change on the facial surface that reflects the brain activity. Meanwhile, the analysis unit 134 determines that the component evaluated to have no correlation among the plurality of components is not a component that exhibits the RGB change on the facial surface reflecting the human brain activity while not satisfying the predetermined condition.

Here, the brain function activation task is given to the individual for a certain period of time in acquiring the time-series photographed image data on the facial surface, and based on this result, the analysis unit 134 extracts the determination component. However, the contents of the first condition. i.e., the extraction means of the determination component in the analysis unit 134 is not limited thereto. For example, when a component that exhibits the component waveform having a correlation with the brain non-activation time and the brain activation time is specified from among the plurality of components by conducting experiments or the like in advance, the analysis unit 134 extracts the specified component from the plurality of components as the determination component. In addition, when a human's movement known to be related to the activation/non-activation of the brain, such as eye movement or blink, is detected on the brain activity visualization device 110, the analysis unit 134 may compare, analyze, and evaluate the detection result and the component waveform of each component, thereby extracting the determination component from the plurality of components. Note that the criterion for the analysis unit 134 to determine whether the first condition is satisfied or not is determined as appropriate by simulation, experiments, desk calculation, or the like in accordance with the purpose of use of the brain activity visualization device 110 or the like.

When the second condition is set as the predetermined condition, the analysis unit 134 extracts the determination component based on the presence or absence of the change in the facial blood circulation amount at a predetermined part on the human's facial surface. Specifically, the analysis unit 134 determines whether or not a change in the blood circulation amount occurs in the paranasal sinus peripheral region and/or the forehead based on the blood circulation amount distribution diagrams corresponding to the plurality of components obtained by the singular value decomposition. Then, if the change in the blood circulation amount occurs for one component, the analysis unit 134 determines that this component satisfies the second condition. On the other hand, when the change in the blood circulation amount does not occur in the paranasal sinus peripheral region and/or the forehead for one component, the analysis unit 134 determines that this component does not satisfy the second condition. Note that the criterion for the analysis unit 134 to determine whether the second condition is satisfied or not is determined as appropriate by simulation, experiments, desk calculation, or the like in accordance with the purpose of use or the like of the brain activity visualization device 110.

Further, when the time-series blood-circulation-amount data based on the RGB data before conversion to the relative RGB data is calculated by the blood circulation amount calculating unit 133, the analysis unit 134 may also determine whether or not the above-mentioned first condition and/or second condition are/is satisfied by the plurality of components obtained by decomposing the blood-circulation-amount data through the singular value decomposition. Then, the analysis unit 134 may extract the determination component from the plurality of components.

The estimation unit 135 estimates the human brain activity based on the component identified by the analysis unit 134 as the component indicative of the RGB change on the facial surface reflecting the human brain activity. Specifically, the estimation unit 135 estimates the amount of brain activity at the time of acquiring the photographed image data on the facial surface based on the component waveform data regarding the component identified by the analysis unit 134.

(4-2-1) Modified Example 2A

As mentioned above, for example, a portable terminal or the like incorporating therein an imaging device, such as a smartphone or a tablet (for example, iPad: registered trademark) can be used as the camera 12. That is, a device for the above-mentioned photographed image data can adopt any device capable of capturing images in the visible light range.

The blood circulation amount calculating unit 133 may calculate the facial blood-circulation-amount data mainly using the R component among the respective pixels included in the RGB data. As long as the blood-circulation-amount data can be calculated based on the RGB data, the blood-circulation-amount data is not necessarily limited to the erythema index.

(4-2-2) Modified Example 2B

The blood circulation amount calculating unit 133 calculates the relative-conversion blood-circulation-amount data based on the relative RGB data obtained by conversion with the conversion unit 132. However, instead of or in addition to this, the blood-circulation-amount data may be calculated based on the RGB data before being converted to the relative RGB data. Here, the components correlated with the brain activity are more likely to appear (with a high verification capability) in the blood-circulation-amount data calculated based on the RGB data before being converted to the relative RGB data. Because of this, for example, the blood-circulation-amount data calculated based on the RGB data before being converted to the relative RGB data may be analyzed prior to the relative-conversion blood-circulation-amount data calculated based on the relative RGB data. Further, for example, first, the blood-circulation-amount data is analyzed to extract a component having a significant correlation with the brain activity. Regarding the relative-conversion blood-circulation-amount data, only a component thereof corresponding to the extracted component of the blood-circulation-amount data is analyzed, so that the computation processing amount can be decreased in total.

(4-2-3) Modified Example 2C

Although it is assumed that the camera 121 is a normal camera of the visible light range, an infrared camera can be used. In this case, an object is irradiated with infrared light, and its reflected wave is photographed by the infrared camera. Thus, the photographed image data including changes of the subject's facial surface or the like can be acquired. The inventors have confirmed that there is a correlation between the blood-circulation-amount data calculated from the photographed image data acquired by reflection of infrared rays and the blood-circulation-amount data calculated mainly using the R component among the respective pixels contained in the RGB data, acquired by photographing with light in the visible light range. Therefore, even the use of such photographed image data acquired from the reflection of the infrared rays enables the estimation of the human brain activity.

(4-2-4) Modified Example 2D

In the description above, the brain activity visualization device 110 includes the image data acquisition means 120 and the brain activity estimation means 130. However, a brain activity visualization device according to the present embodiment is not limited to such a configuration. That is, the brain activity visualization device according to the present embodiment may have any other configuration as long as it includes the blood circulation amount calculating unit 133, the analysis unit 134, and the estimation unit 135. Specifically, the brain activity visualization device according to the present embodiment can have not only a configuration in which the brain activity visualization device itself photographs or captures image data, but also a configuration in which the brain activity visualization device receives photographed image data from an external device and then analyzes the received data.

(4-3) State Visualization Means 200

The state visualization means 200 visualizes the physiological state of the subject by displaying based on the brain activity of the subject estimated by the brain activity estimation means 30 and/or the brain activity estimation means 130. For example, the state visualization means 200 may include an analysis means 201 that analyzes the physiological state of the subject through the analysis of changes in the amount of brain activity of the subject. Specifically, the analysis means 201 determines the physiological state of the subject by analyzing a change in the amount of brain activity with respect to a stimulus given to the subject (visual stimulus, auditory stimulus, tactile stimulus, odor stimulus, taste stimulus, and the like). The type and level of the physiological state may be determined based on an increased amount of the brain activity and/or duration of the brain activity amount. Then, based on the determined physiological state, the analysis means 201 may be set as appropriate in accordance with applications of the brain activity visualization devices 10 and 110. The physiological state of the subject analyzed by the analysis means 201 is output from a display means 202 of the state visualization means 200 to an administrator, so that the administrator can know the physiological state of the subject. The display means 202 can be any display device, such as a display device for displaying an image or a message, which can visualize information on the physiological state of an analyzed subject to the administrator.

In addition, when various data are acquired in time series by the facial skin temperature acquisition means 20 and/or the image data acquisition means 120 after the components reflecting the brain activity are identified in the analysis units 32 and 134, the brain activity visualization device 10 and 110 decompose various acquired data into a plurality of components by the singular value decomposition, and then analyze the identified components only, thereby making it possible to know the physiological state of the subject in real time.

Furthermore, there has been a conventional technique for acquiring heart rate information, biological information, and the like of the test subject from the facial skin temperature of the test subject and a photographed image thereof. Owing to this, various data acquired from the facial skin temperature acquisition means 20 and/or the image data acquisition means 120 are decomposed into components by the singular value decomposition or the like. Then, the above conventional technique is applied to the component obtained by the singular value decomposition, thereby making it possible to accurately acquire the heart rate information and biological information. Therefore, the analysis unit 32 and/or analysis unit 134 may have the function of acquiring the heart rate information and biological information by analyzing the plurality of components decomposed by the singular value decomposition, whereas the estimation units 33 and 135 of the present embodiment may have the function of estimating the activity of the sympathetic nerve/parasympathetic nerve based on the acquired heart rate information or biological information.

(5) Features 5-1

In the present embodiment, the human brain activity can be estimated based on the time-series facial skin temperature data and/or facial blood-circulation-amount data acquired by the facial skin temperature acquisition means 20 and/or the image data acquisition means 120, respectively. Thus, the human brain activity can be estimated even when a sensor, such as a brain wave electrode, requiring any processing before attachment is not attached. Therefore, the human brain activity can be easily estimated, and thereby the physiological state of the subject can be visualized based on the estimated brain activity.

(5-2)

Here, when the time-series facial skin temperature data and/or image data are acquired, the human brain is activated or not activated by actually giving the brain function activation task to the human or not. In such a case, a component having a correlation between its component waveform and each of the brain activation time and the brain non-activation time is said to be highly likely to exhibit changes in the skin temperature and/or blood circulation amount reflecting the brain activity.

In the present embodiment, the brain function activation task is given to the individual for a certain period of time while the time-series facial skin temperature data and/or image data is acquired by the facial skin temperature acquisition means 20 and/or image data acquisition means 120, respectively. That is, in the present embodiment, the human brain is activated or not activated by actually giving the brain function activation task to the individual or not. Then, various data acquired in time series in this way is decomposed into a plurality of components by the singular value decomposition. Then, the correlation between the component waveform of each component and each of the brain activation time and brain non-activation time is evaluated, and consequently, the component evaluated to have the correlation is extracted from the plurality of components as the determination component. Thus, for example, the possibility that the component less related to the human brain activity is extracted as the extraction component from the plurality of components can be reduced, as compared with when a predetermined component specified by experiments or the like in advance is extracted as the extraction component from the plurality of components.

5-3

Here, the brain has a mechanism called selective brain cooling system, which cools the brain independently of the body temperature. The selective brain cooling mechanism is known to discharge heat generated by the brain activity through the forehead and the paranasal sinus peripheral region. As such, the changes in the facial skin temperature and in the facial blood circulation amount correlated with the facial skin temperature appear in the forehead and/or paranasal sinus peripheral region.

In the present embodiment, various data acquired from the forehead and/or the paranasal sinus peripheral region are analyzed to extract the determination component. Thus, the component related to the human brain activity can be extracted with high accuracy.

(6) Application Examples of Brain Activity Visualization Device (Fatigue State Determination Device)

A description will be given on the fatigue state determination device according to the present invention, to which the brain activity visualization device is applied.

(6-1) Configuration of Fatigue State Determination Device

Figure 23:
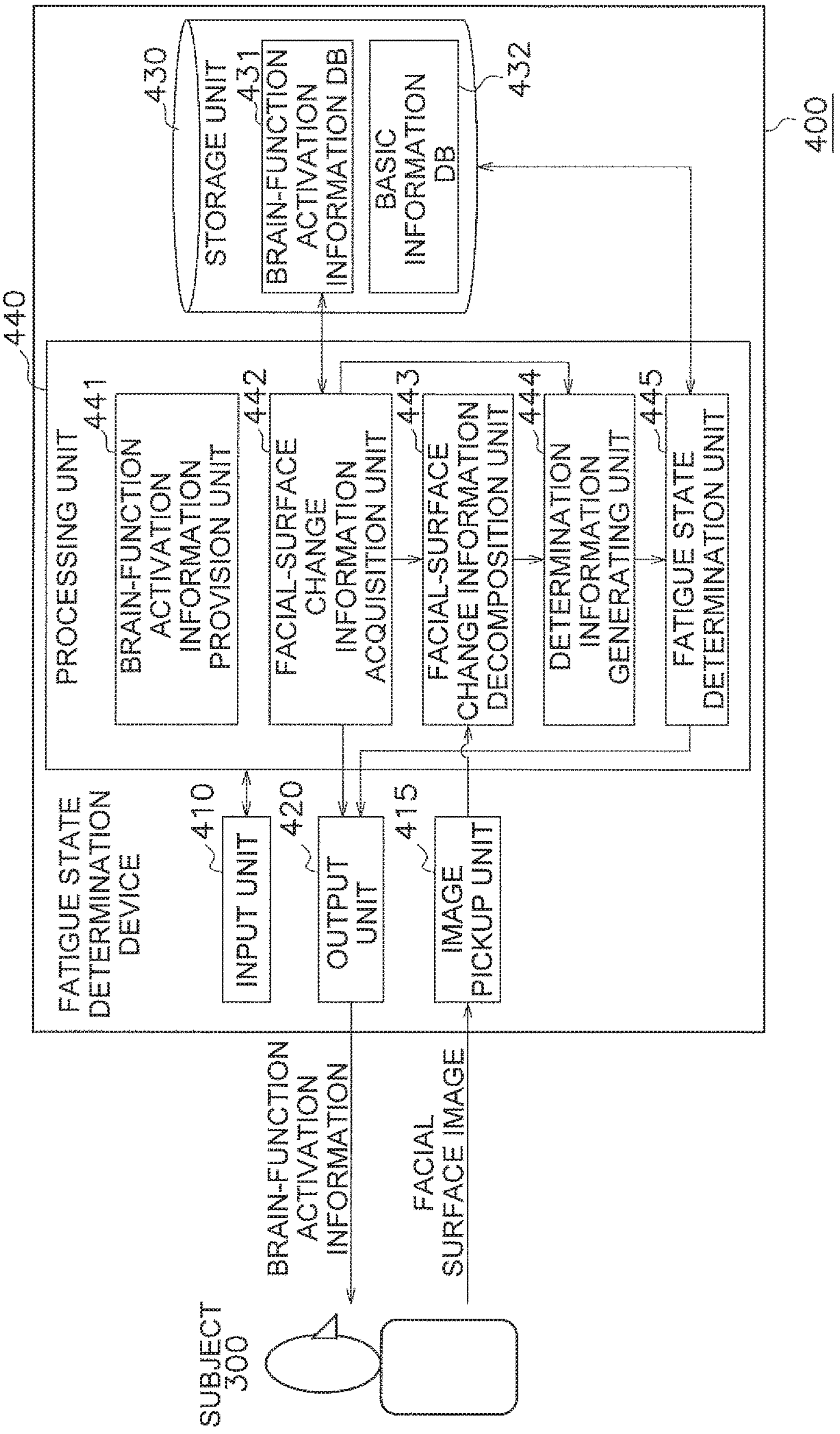
FIG. 23 is a schematic diagram showing a configuration of a fatigue state determination device according to the embodiment of the present invention.

FIG. 23 is a schematic diagram showing an example of the fatigue state determination device according to the embodiment of the present invention.

A fatigue state determination device 400 includes an input unit 410, an image pickup unit 415, an output unit 420, a storage unit 430, and a processing unit 440.

The input unit 410 is to input various types of information into the fatigue state determination device 400. For example, the input unit 410 may include a keyboard, a mouse, and/or a touch screen, and the like. Various commands are input to the fatigue state determination device 400 via the input unit 410, and processing in response to the input command is executed in the processing unit 440.

The image pickup unit 415 captures a "facial surface image" including a facial surface of a subject 300. For example, the image pickup unit 415 is configured by a solid-state imaging device, such as a Charge Coupled Device (CCD) or a Complementary Metal-Oxide-Semiconductor (CMOS), for acquiring RGB images, an infrared camera for acquiring thermograms, or the like. When the infrared camera is used as the image pickup unit 415, the fatigue state determination can be conducted without being influenced by the ambient brightness. In particular, accidents or the like due to fatigue tend to occur at night. Also, in this case, by mounting the infrared camera on the fatigue state determination device 400 according to a first embodiment, the fatigue state of the subject can be monitored at night. Desirably, the infrared camera or the like is one capable of detecting the temperatures from 29.0° C. to 37.0° C. under a normal room temperature condition with high sensitivity. The image pickup unit 415 is capable of continuously capturing images at predetermined intervals. In the case of capturing a facial surface image, capturing an image from the front and with constant illumination is desirable. When the front image cannot be obtained due to variations in the subject's posture, the three-dimensional shape of the face is estimated for posture variation images by using a perturbation space method, and referring to the estimated shape, the front image is rendered, thereby producing a facial surface image. As for an illumination variation image, a facial surface image under the constant illumination condition is produced using an illumination basis model of a face configured based on a diffusing reflection model. Then, the facial surface image continuously captured by the image pickup unit 415 is sent to the processing unit 440.

The output unit 420 is to output various types of information from the fatigue state determination device 400. For example, the output unit 420 includes a display, a speaker, and the like. Here, the brain-function activation information to be described later is provided to the subject 300 via the output unit 420.

The storage unit 430 stores information input to the fatigue state determination device 400, information calculated by the fatigue state determination device 400, and the like. For example, the storage unit 430 includes a memory, a hard disk device, and the like. The storage unit 430 stores a program for achieving each function of the processing unit 440 to be described later. Here, the storage unit 430 includes a brain-function activation information database 431 and a reference information database 432.

The brain-function activation information database 431 stores therein brain-function activation information for activating the human brain function. Here, working memory related information or the like, related to a working memory of the human brain, is used as the "brain-function activation information". The "working memory related information" is information on tasks requiring memory ability and judgment ability, and includes mental arithmetic tasks, calculation tasks, memorization tasks, such as an N back task, a task of making an optimal selection from a plurality of pieces of information, such as a pictogram question, and attention switching tasks and the like, which involve switching tasks in the middle. Here, the subject 300 tackles mental arithmetic tasks displayed on the display device or the like, and consequently the brain of the subject 300 is activated to use the working memory.

Figure 24:
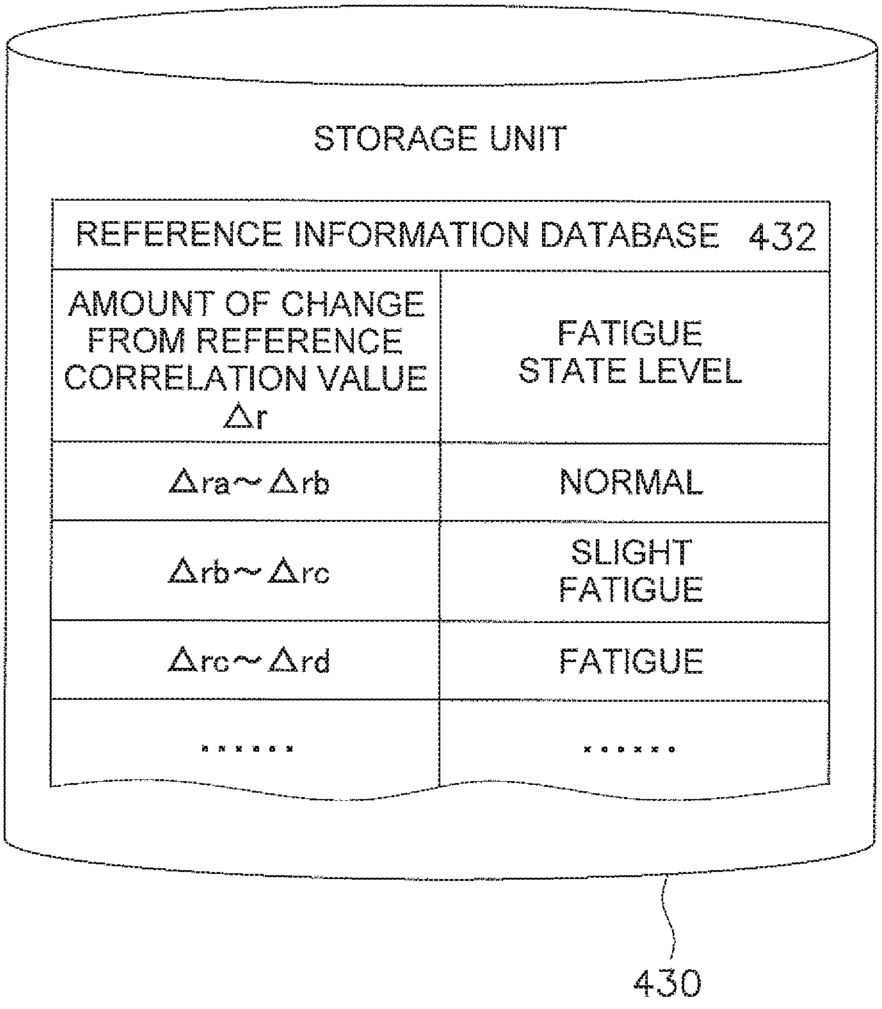
FIG. 24 is a schematic diagram showing a configuration of a reference information database in the fatigue state determination device.

As shown in FIG. 24, the reference information database 432 previously stores, as "reference information" in relation to the "fatigue state level", an amount of change $\Delta r$ ($=r1-r2$) within a predetermined range, from a "reference correlation value r1" of the reference determination component to a correlation value r2 of the determination component, where r2 is the correlation value of the determination component extracted by a determination information generating unit 444, to be described later, with respect to the brain-function activation information, whereas r1 is the reference correlation value of the reference determination component with respect to the brain-function activation information. The "reference determination component" is set by data on the determination component extracted before a predetermined action, data on the determination component previously extracted, data on the determination component provided from the outside, and the like. In an example shown in FIG. 24, the reference information database 432 stores the reference information therein corresponding to the range of the amount of change $\Delta r$, specifically, $\Delta r=\Delta ra$ to $\Delta rb$ as "normal"; $\Delta rb$ to $\Delta rc$ as "slight fatigue"; and $\Delta rc$ to $\Delta rd$ as "fatigue". Here, $\Delta ra$, $\Delta rb$, $\Delta rc$, and $\Delta rd$ are arranged in ascending order. Note that data on the reference determination component are also stored in the reference information database 432.

The processing unit 440 executes information processing in the fatigue state determination device 400. Specifically, the processing unit 440 includes a CPU, a cash memory, and the like. The processing unit 440 executes programs stored in the storage unit 430 to function as a brain-function activation information provision unit 441, a facial-surface change information acquisition unit 442, a facial-surface change information decomposition unit 443, a determination information generating unit 444, and a fatigue state determination unit 445.

The brain-function activation information provision unit 441 refers to a member that provides the brain-function activation information. For example, the brain-function activation information provision unit 441 reads the brain-function activation information from the brain-function activation information database 431 in response to the operation of the input unit 410 and then outputs the read brain-function activation information to the output unit 420.

The facial-surface change information acquisition unit 442 acquires "facial surface data" and "facial-surface change information" indicative of time-series changes in the facial surface data from the facial surface image captured by the image pickup unit 415. Specifically, the facial-surface change information acquisition unit 442 acquires the facial surface data via the image pickup unit 415 in synchronization with the timing at which the brain-function activation information provision unit 441 provides the brain-function activation information. The facial-surface change information acquisition unit 442 acquires the facial-surface change information indicative of the time-series changes in the facial surface data on the subject 300, from the facial surface data continuously acquired. For example, facial surface data of 240×320 pixels are acquired from 60 points at predetermined intervals to thereby produce the facial-surface change information composed of a collection of 4,608,000 pieces of data. The acquired facial-surface change information is sent to the facial-surface change information decomposition unit 443. Note that when the image pickup unit 415 is an infrared camera, the facial-surface change information acquisition unit 442 acquires facial skin temperature data indicative of the facial skin temperature of the subject 300 as the facial surface data. When the image pickup unit 415 is a solid-state imaging device, such as a CCD and a CMOS, the facial-surface change information acquisition unit 442 acquires facial blood-circulation-amount data based on the RGB data regarding the facial surface of the subject 300 as the facial surface data. It should be noted that the facial-surface change information acquisition unit 442 may acquire the data only about the paranasal sinus peripheral region and/or the forehead of the subject 300 as the facial surface data.

The facial-surface change information decomposition unit 443 decomposes the facial-surface change information, which is the collection of a number of data, into a plurality of components 1, 2, 3, . . . by the singular value decomposition, the principal component analysis, or the independent component analysis. The information on the respective decomposed components is sent to the determination information generating unit 444. Here, when the facial-surface change information is subjected to the singular value decomposition or the like, the components 1, 2, 3 . . . are set in descending order of the singular value. In addition, the component with the higher singular value is more likely to be influenced by a factor that varies largely. Because of this, the component 1 is often influenced by noise or the like of the external environment rather than by the provision of the brain-function activation information.

The determination information generating unit 444 generates determination information from the facial-surface change information. Specifically, the determination information generating unit 444 extracts a component related to the brain-function activation information from the plurality of components 1, 2, 3, . . . as a "determination component", and generates determination information from the determination component. In detail, the determination information generating unit 444 calculates a correlation value r of the extracted determination component with respect to the brain-function activation information. Specifically, the determination information generating unit 444 calculates a correlation value r between each of a plurality of components 1, 2, 3, . . . determined by the facial-surface change information decomposition unit 443 and the brain-function activation information. Then, when the calculated correlation value r is equal to or more than a predetermined value, the determination information generating unit 444 sets a component corresponding to the correlation value r as one related to the brain-function activation information. The determination information generating unit 444 extracts the determination component based on a value of the significance level. That is, the determination information generating unit 444 extracts a component having a low significance level as the determination component. The extracted determination component and the calculated correlation value r are sent to the storage unit 430 or the fatigue state determination unit 445.

The fatigue state determination unit 445 determines a fatigue state of the subject 300 based on the determination information including the determination component. Specifically, a fatigue state determination unit 450 calculates a difference Δr between a reference correlation value r1 of the reference determination component extracted before a predetermined action with respect to the brain-function activation information and a correlation value r2 of the determination component extracted after the predetermined action with respect to the brain-function activation information. Then, the fatigue state determination unit 450 decides a fatigue state level corresponding to the difference Δr between the reference correlation value r1 and the present correlation value r2 based on the reference information stored in the reference information database 432. The decided fatigue state level is output to the display device or the like via the output unit 420.

Note that in the present embodiment, the term "predetermined action" as used herein means one or both of a physical activity and an intellectual activity. Examples of the physical activity include various physical labor, such as line works in factories and civil engineering work, and various exercises, such as fitness, running, ball games, mountain climbing, and muscle training. Examples of the intellectual activity include learning, discussion, decision making, situation judgement, management and supervision, and the like.

(6-2) Operation of Fatigue State Determination Device

Figure 25A:
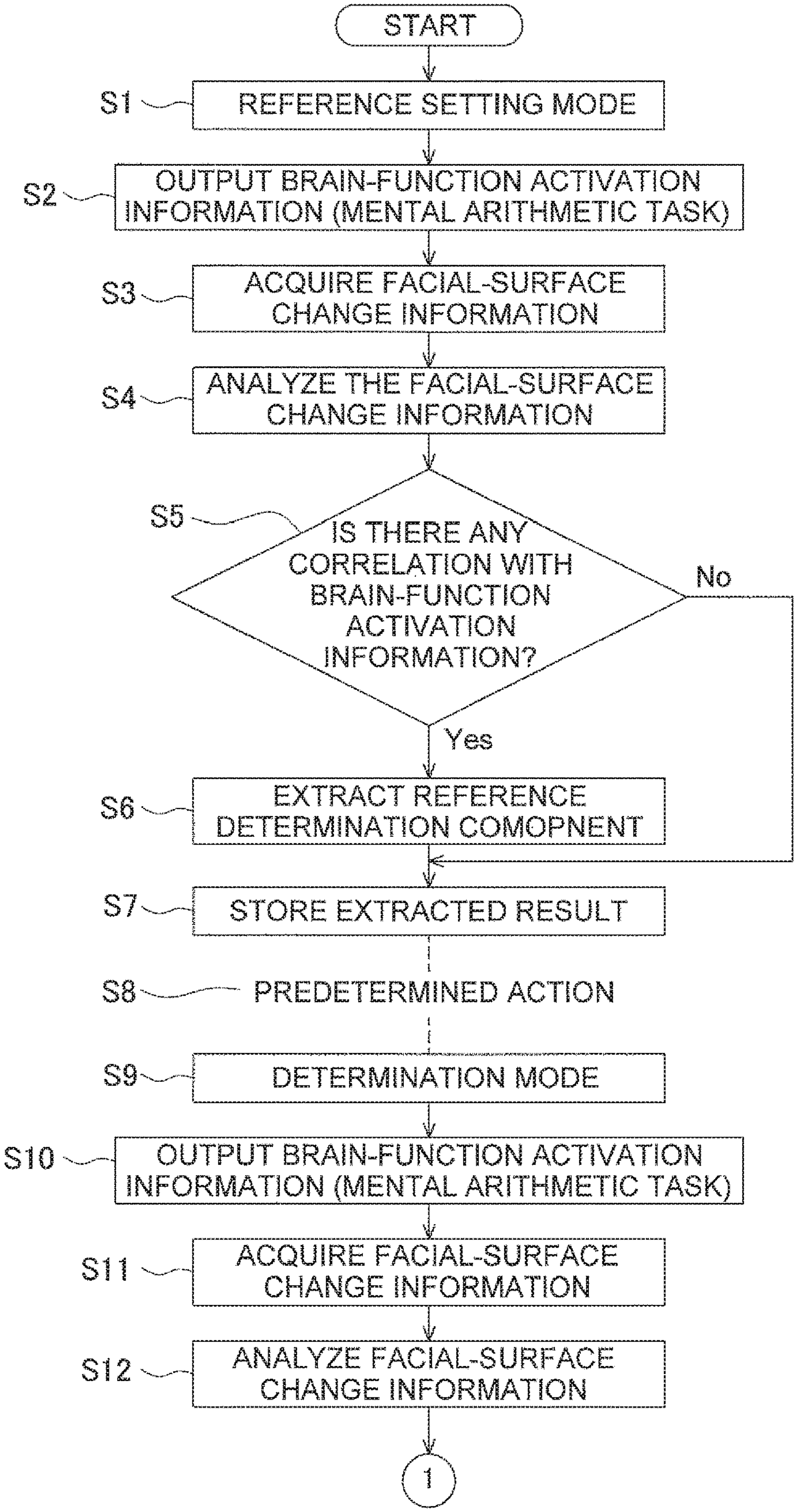
FIG. 25A is a flowchart showing an operation of the fatigue state determination device.
Figure 25B:
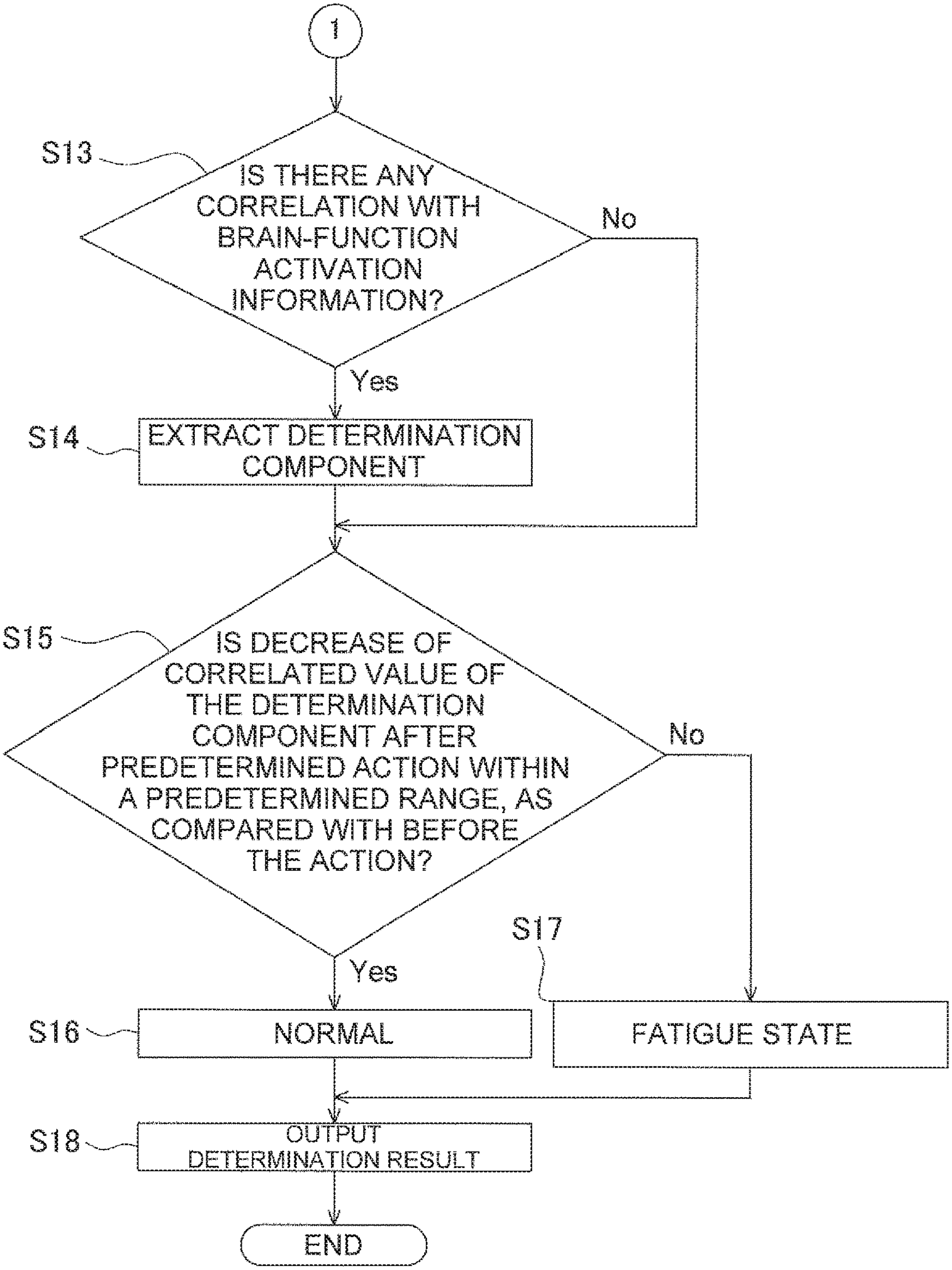
FIG. 25B is a flowchart showing an operation of the fatigue state determination device.

FIG. 25 is a flowchart showing an operation of a fatigue state determination device 400.

First, a "reference setting mode" is selected before the predetermined action, and a reference determination component is extracted (S1). Specifically, an output instruction of the brain-function activation information is input to the fatigue state determination device 400 via the input unit 410.

Subsequently, the brain-function activation information is read from the brain-function activation information database 431 and output to the output unit 420 (S2). Here, mental arithmetic tasks are output as the brain-function activation information.

Then, a facial surface image of the subject 300 in front of the output unit 420 is captured by the image pickup unit 415 at prescribed intervals, specifically, at predetermined timing or at the same time as the output of the brain-function activation information (S3). The captured facial surface image is sent to the facial-surface change information acquisition unit 442.

Subsequently, the facial-surface change information acquisition unit 442 acquires, from the captured facial surface image, facial-surface change information indicative of the time-series changes in the facial surface data on the subject 300. Then, the facial-surface change information decomposition unit 443 decomposes the facial-surface change information into a plurality of components 1, 2, 3, . . . by the singular value decomposition, the principal component analysis, or the independent component analysis (S4).

Then, the determination information generating unit 444 calculates a correlation value between each of the plurality of components 1, 2, 3, . . . decomposed by the facial-surface change information decomposition unit 443 and the brain-function activation information. Subsequently, the determination information generating unit 444 determines whether the correlation value is equal to or more than a predetermined value (S5). If the correlation value is determined to be equal to or more than the predetermined value, it is determined that the brain-function activation information and this component are correlated with each other (S5—Yes). Then, the determination information generating unit 444 extracts a component having a low significance level among the components having the correlation, as the "reference determination component" (S6). The determination information generating unit 444 sets the correlation value between the reference determination component and the brain-function activation information as the reference correlation value r1. This information on the reference determination component is stored in the storage unit 430 (S7). On the other hand, if the correlation value between the brain-function activation information and each of the components 1, 2, 3, . . . is less than the predetermined value, it is determined that both the brain-function activation information and the component has no correlation with each other, and then this information is stored in the storage unit 430 (S5—No, S7).

Then, the subject 300 performs a predetermined action (S8). Subsequently, the fatigue state determination device 400, in which a "determination mode" is selected, executes fatigue state determination caused by the predetermined action (S9). First, the same processing as those in the above-mentioned steps S2 to S6 is executed, and then a correlation value r2 between the determination component extracted from the facial-surface change information and the brain-function activation information is calculated (S10 to S14).

Then, the fatigue state determination unit 445 calculates an amount of change Δr, which is a difference between a reference correlation value r1 and a correlation value r2, where r1 is the reference correlation value of the reference determination component extracted before the predetermined action with respect to the brain-function activation information, and r2 is the correlation value of the determination component extracted after the predetermined action with respect to the brain-function activation information (S15). Subsequently, the fatigue state determination unit 450 determines whether the amount of change Δr of the correlation value r2 with respect to the reference correlation value r1, generated between before and after the predetermined action, is within a predetermined range or not. Whether the amount of change Δr of the correlation value r2 with respect to the reference correlation value r1 is within the predetermined range or not is determined based on the reference information stored in the reference information database 432. If the amount of change Δr of the correlation value r2 with respect to the reference correlation value r1 is within the predetermined range, the fatigue state determination unit 445 determines that the subject 300 is "normal" (S15—Yes, S16). On the other hand, if the amount of change Δr of the correlation value r2 with respect to the reference correlation value r1 is not within the predetermined range, the fatigue state determination unit 445 determines that the subject 300 is "in a fatigue state" (S15—No, S17). For example, if the amount of change Δr is within the above-mentioned range of Δra to Δrb, the subject is determined to be normal. On the other hand, if the amount of change Δr exceeds Δrb, the subject is determined to be in the fatigue state. These determination results are output as the determination result to the display device or the like via the output unit 420 (S18).

(6-3) Features of Fatigue State Determination Device

6-3-1

As described above, the fatigue state determination device 400 according to the present embodiment includes a brain-function activation information provision unit 441, a facial-surface change information acquisition unit 442, a facial-surface change information decomposition unit 443, a determination information generating unit 444, and a fatigue state determination unit 445. The brain-function activation information provision unit 441 provides "brain-function activation information" for activating the human brain function to the subject 300. The facial-surface change information acquisition unit 442 acquires the "facial-surface change information" indicative of the time-series changes in the facial surface data regarding the subject 300. The facial-surface change information decomposition unit 443 decomposes the facial-surface change information into a plurality of components 1, 2, 3, . . . by the singular value decomposition, the principal component analysis, or the independent component analysis. The determination information generating unit 444 extracts a component related to the brain-function activation information from the plurality of components 1, 2, 3, . . . as a "determination component". The fatigue state determination unit 445 determines the fatigue state of the subject 300 based on the determination component.

Therefore, the fatigue state determination device 400 according to the present embodiment extracts the determination component related to the brain-function activation information, from a plurality of components 1, 2, 3, . . . obtained by conducting the singular value decomposition, the principal component analysis, the independent component analysis, or the like on the facial-surface change information. This makes it possible to easily estimate the presence or absence of the brain activity of the subject 300 without using any electrode or the like that requires preprocessing before attachment. Thus, the fatigue state of the subject 300 can be easily determined based on the determination component corresponding to the brain function of the subject 300.

Note that the fatigue state determination device 400 according to the present embodiment may be incorporated in a smart device. Thus, the fatigue state determination can be easily executed at an arbitrary location.

6-3-2

In the fatigue state determination device 400 according to the present embodiment, the facial-surface change information acquisition unit 442 acquires the data on the paranasal sinus peripheral region and/or the forehead of the subject 300 as the facial surface data, thereby making it possible to extract the determination component related to the brain activity with high accuracy. Here, the brain has a mechanism called "Selective Brain Cooling System" which cools the brain independently of body temperature. The selective brain cooling system is known to discharge heat generated by the brain activity through the forehead and the paranasal sinus peripheral region. Thus, by analyzing data on these parts, the component related to the brain activity can be extracted with high accuracy. Consequently, the fatigue state determination device 400 according to the present embodiment can execute the fatigue state determination with high accuracy.

6-3-3

Figure 26:
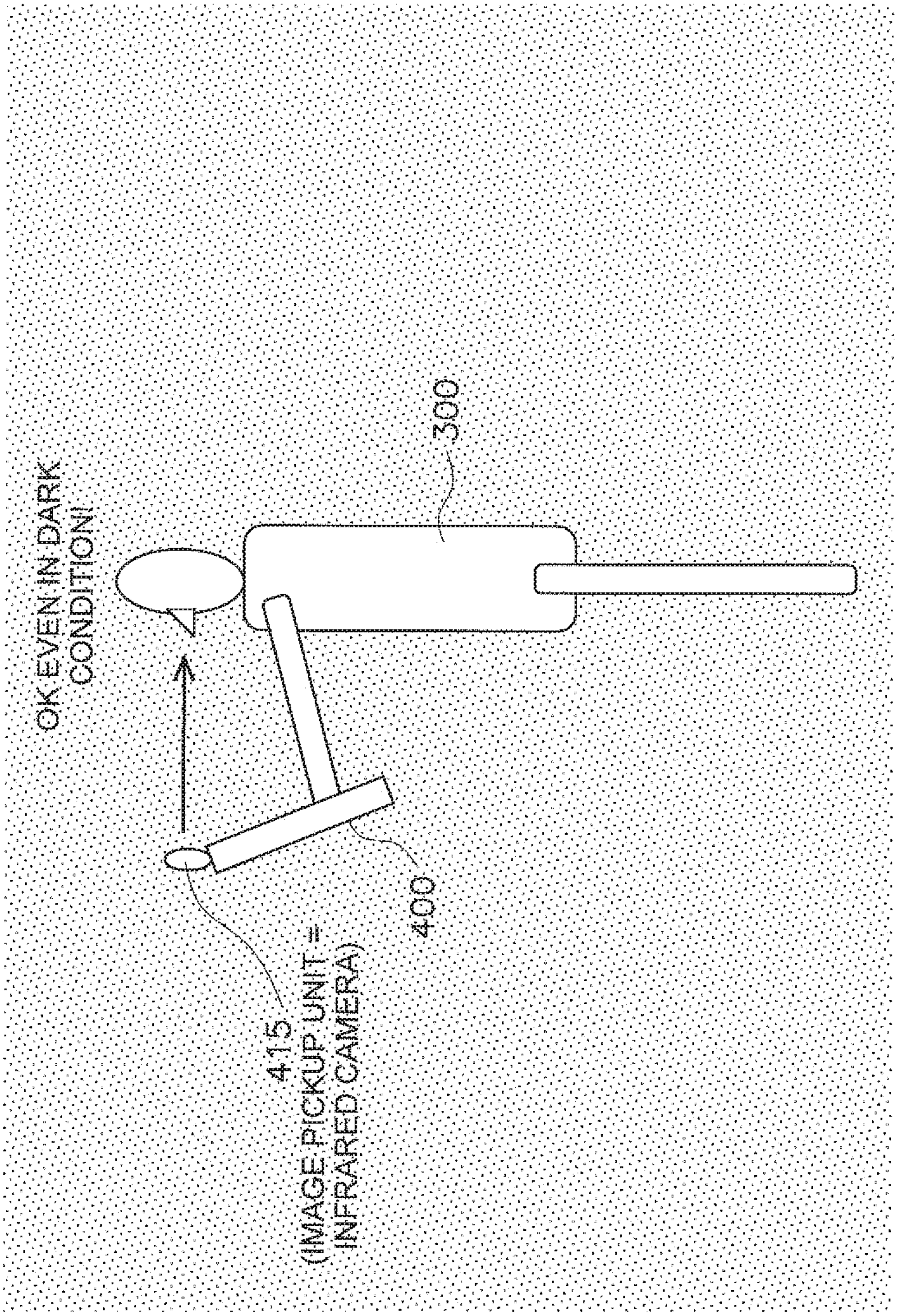
FIG. 26 is a schematic diagram showing an example of using an infrared camera in the fatigue state determination device.

In the fatigue state determination device 400 according to the present embodiment, the facial-surface change information acquisition unit 442 acquires the facial skin temperature data indicative of the facial skin temperature of the subject 300 as the facial surface data. In other words, the fatigue state determination device 400 can determine the fatigue state of the subject using an infrared camera or the like. For example, as shown in FIG. 26, the infrared camera is used in the image pickup unit 415, thereby enabling the fatigue state determination without being influenced by the ambient brightness.

6-3-4

In the fatigue state determination device 400 according to the present embodiment, the facial-surface change information acquisition unit 442 acquires the facial blood-circulation-amount data based on the RGB data regarding the facial surface of the subject 300, as the facial surface data. That is, the fatigue state determination device 400 can determine the fatigue state using the solid-state imaging device (CCD, CMOS). Thus, the fatigue state determination can be executed with a simple configuration.

6-3-5

In the fatigue state determination device 400 according to the present embodiment, the determination information generating unit 444 extracts the determination component based on a value of the significance level. The fatigue state determination device 400 extracts the determination component related with the brain-function activation information based on the value of the significance level, thereby making it possible to enhance the reliability of the fatigue state determination.

6-3-6

In the fatigue state determination device 400 according to the present embodiment, the brain-function activation information provision unit 441 provides working memory related information as the brain-function activation information. For example, by providing a mental arithmetic task or the like as the brain-function activation information, the component related to the brain activity can be extracted. Consequently, the fatigue of the subject 300 can be easily determined.

Figure 27:
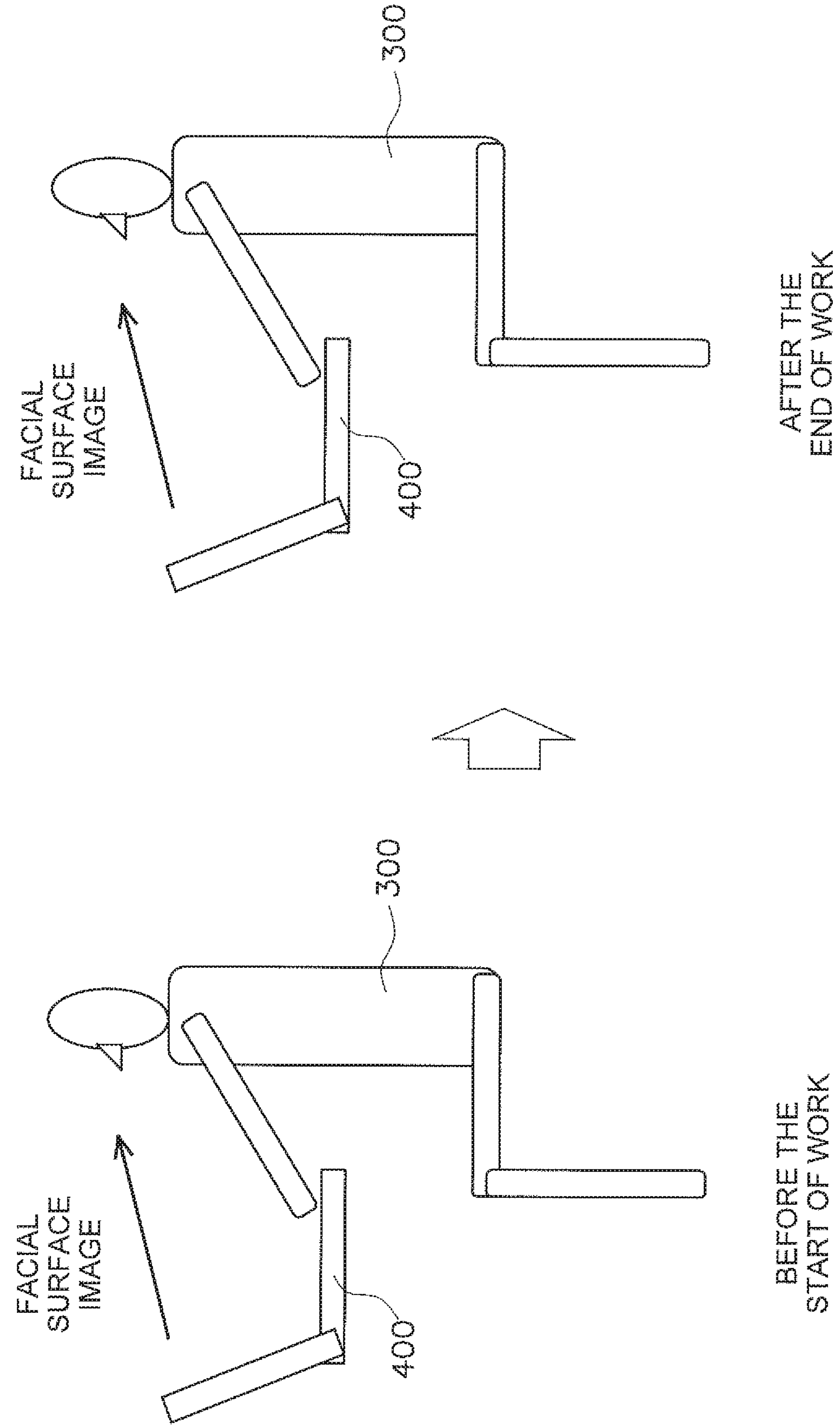
FIG. 27 is a schematic diagram showing an example of usage of the fatigue state determination device.

Note that the work content itself may be used as the brain-function activation information, specifically, as working memory related information. For example, as shown in FIG. 27, in desk work using a PC or the like, the facial surface data is acquired at a predetermined timing from the start of work to the end of work. Then, the fatigue state corresponding to the execution of the work can be determined by calculating the correlation value r between the operation displayed on the screen of the PC and the determination component acquired based on the facial surface data at any time.

6-3-7

The fatigue state determination device 400 according to the present embodiment includes the reference information database 432 that stores therein, as "reference information" in relation to the fatigue state level, an amount of change Δr within a predetermined range, from the reference correlation value r1 of the reference determination component calculated with respect to the brain-function activation information, to the correlation value r2 of the determination component calculated with respect to the brain-function activation information. Subsequently, the fatigue state determination unit 445 calculates the correlation value r2 of the determination component with respect to the brain-function activation information, and determines the fatigue state level of the subject 300 based on the calculated correlation value r2 and the reference information.

With this configuration, the fatigue state determination device 400 can easily determine the fatigue state level using the reference determination component obtained before the predetermined action. In short, the fatigue state determination device 400 not only determines just the presence or absence of the fatigue, but also can easily determine and output the fatigue state level.

6-3-8

A fatigue state determination method according to the present embodiment does not necessarily require the fatigue state determination device 400. That is, a fatigue state determination method according to the present embodiment may include: a brain-function activation information provision step of providing "brain-function activation information" for activating human brain activity to a subject 300 after a predetermined action, regardless of the presence or absence of the fatigue state determination device 400; a facial-surface change information acquisition step of acquiring "facial-surface change information" indicative of time-series changes in facial surface data of the subject 300 after a predetermined action; a facial-surface change information decomposition step of decomposing the facial-surface change information into a plurality of components by the singular value decomposition, the principal component analysis, or the independent component analysis; a determination component extraction step of extracting a component related to the brain-function activation information as a "determination component" from the plurality of components; and a fatigue state determination step of determining a fatigue state of the subject 300 based on the determination component.

With this fatigue state determination method, the plurality of components is obtained by conducting the singular value decomposition, the principal component analysis, or the independent component analysis on the facial-surface change information after the predetermined action, and then the determination component related to the brain-function activation information is extracted from the plurality of components, thereby determining the fatigue state. Thus, the influence of the predetermined action on the fatigue of the subject 300 can be easily determined.

6-3-9

Note that in the above description, the determination component related to the brain-function activation information corresponding to the target purpose is extracted from the facial-surface change information by conducting the singular value decomposition or the like. However, the fatigue state determination device 400 according to the present embodiment is not limited to such a configuration. For example, in the fatigue state determination device 400, determining state of the subject can be conducted by using arbitrary determination information other than the determination component generated based on the facial-surface change information. Also arbitrary method other than the singular value decomposition or the like, may be applied to the facial-surface change information in order to generate such determination information.

(6-4) Modified Example of Fatigue State Determination Device

Figure 28:
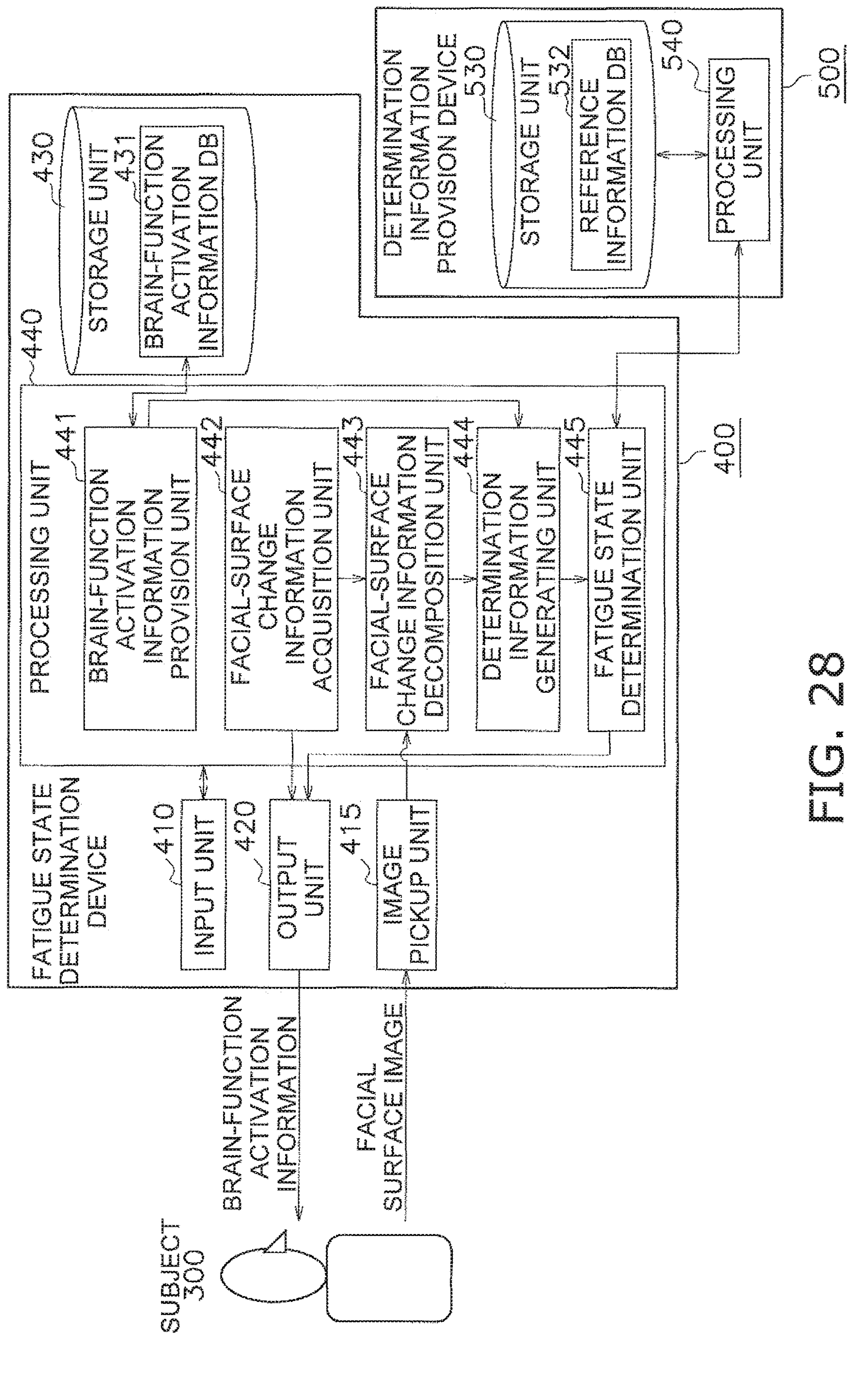
FIG. 28 is a schematic diagram showing a modified example of the fatigue state determination device.

As shown in FIG. 28, the fatigue state determination device 400 according to the present embodiment may use a determination information provision device 500 or the like provided on a network.

Here, the determination information provision device 500 includes a storage unit 530 and a processing unit 540.

The storage unit 530 includes a reference information database 532. The reference information database 532 has substantially the same configuration as the above-mentioned reference information database 432. That is, the reference information database 532 stores therein, as reference information in relation to the fatigue state level, an amount of change Δr within a predetermined range from the reference correlation value r1 of the reference determination component calculated with respect to the brain-function activation information to the correlation value r2 of the determination component calculated with respect to the brain-function activation information.

The processing unit 540 sends the reference information stored in the reference information database 532 in response to a request from the fatigue state determination device 400. Note that the processing unit 540 may have a function of generating the reference information based on predetermined information as big data, independently of the determination component extracted by the fatigue state determination device 400. Furthermore, when the reference correlation value r1 is calculated by the fatigue state determination device 400, the processing unit 540 executes processing for updating the reference correlation value r1 stored in the reference information database 432 as needed.

In the present modified example, the fatigue state determination unit 445 requests the above-mentioned determination information provision device 500 to provide the reference information. In detail, in the fatigue state determination device 400 according to the present modified example, the reference information database 532 is stored in the determination information provision device 500 on the network, and the fatigue state determination unit 445 accesses the determination information provision device 500 when determining the fatigue state level. Then, the fatigue state determination unit 445 determines the fatigue state level of the subject 300 based on the calculated correlation value r2 and the reference information.

Figure 29:
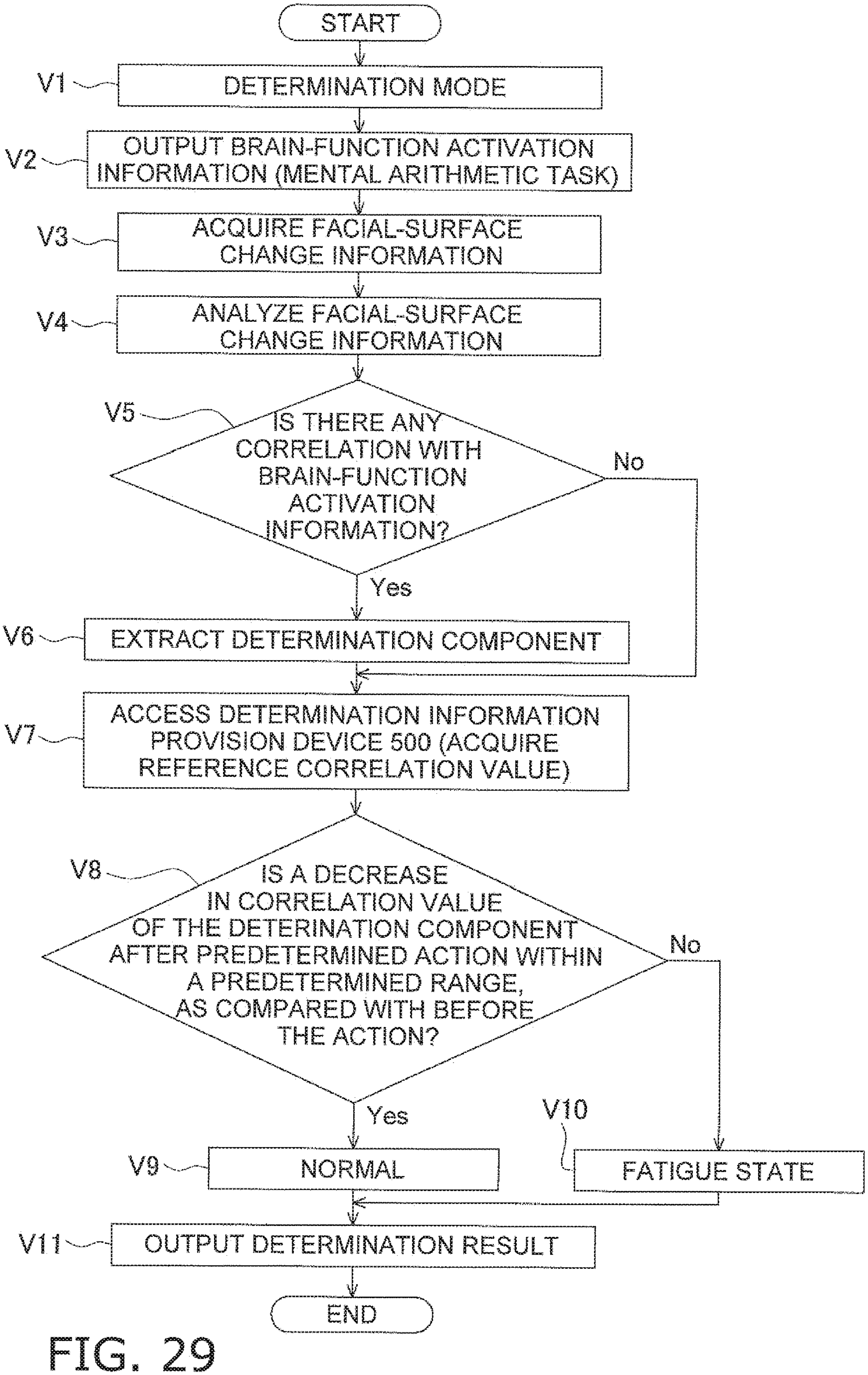
FIG. 29 is a flowchart showing an operation of the modified example of the fatigue state determination device.

Therefore, according to the fatigue state determination device 400 of the present modified example, the fatigue state determination unit 445 can determine the fatigue state level of the subject 300 using an external network. Furthermore, the fatigue state determination unit 445 determines the fatigue state using the reference determination component stored in the determination information provision device 500 on the external network, thereby making it possible to simplify the operation before the predetermined action. That is, the above-mentioned "reference setting mode" is omitted, and a configuration of executing only the "determination mode" can be employed as shown in FIG. 29. Here, the same processing as those in steps S9 to S18 are conducted in steps V1 to V6 and V8 to V11. In step V7, the fatigue state determination device 400 requests the determination information provision device 500 to send the reference information. Note that a part of each step described above may be conducted without using the fatigue state determination device 400.

Moreover, according to the method of the present modified example, the fatigue state determination can be conducted using the big data. That is, the reference correlation value r1 and the predetermined amount of change Δr are determined from the big data. Specifically, the reference correlation value r1 is calculated based on a reference determination component obtained by providing the brain-function activation information to a person other than the subject 300, and then the calculated reference correlation value r1 is used. In this way, the reference information can be optimized as needed.

(6-5) Verification of Fatigue State Determination Method

A verification experiment of the fatigue state determination method according to the present embodiment was performed on the following conditions.

In the experiment, a mental arithmetic task was provided to a physical worker before and after the action accompanied by a predetermined physical activity on the physical worker, and then a facial surface image of the physical worker at each time was captured. The mental arithmetic task was subtracting 7 from 100. The imaging time was about 250 seconds before the action and about 180 seconds after the action. Consequently, regarding each of 11 subjects, the results of the correlation value Rpre with respect to the brain-function activation information before the action and the correlation value Rpost with respect to the brain-function activation information after the action were obtained as shown in Table 4 below. Here, since one data was lost, the effective number was 10.

TABLE 4

| Subject No. | Correlation value r | |
|---|---|---|
| | Before action r1 | After action r2 |
| 1 | 0.71 | 0.58 |
| 2 | 0.92 | 0.66 |
| 3 | 0.87 | 0.95 |
| 4 | 0.88 | 0.55 |
| 5 | N/A | N/A |
| 6 | 0.89 | 0.77 |
| 7 | 0.81 | 0.52 |
| 8 | 0.75 | 0.7 |
| 9 | 0.76 | 0.63 |
| 10 | 0.98 | 0.74 |
| 11 | 0.81 | 0.78 |
| Average | 0.838 | 0.688 |
| Standard deviation | 0.084433 | 0.128996 |

In these results, in comparison of the average correlation value before and after the action, an average correlation value r1 before the action was 0.84, whereas an average correlation value r2 after the action was 0.69. That is, the correlation value r2 after the action is decreased, compared to the correlation value r1 before the action. From this fact, the correlation value r of the determination component with respect to the brain-function activation information is considered to decrease after the action, as compared with before the action. In other words, it is confirmed that by comparing the correlation values determined before and after the action, the fatigue state determination can be conducted. It is confirmed that the fatigue state determination method of the present embodiment can easily determine the fatigue state before and after the predetermined physical activity in the physical worker.

<Note>

It should be noted that the present invention is not limited to the above-mentioned embodiments as they are. The present invention can be embodied by modifying its component without departing from the scope and spirit of the present invention at the stage of implementation. Furthermore, the present invention can produce various inventions by appropriate combinations of a plurality of components disclosed in the above-mentioned embodiments. For example, some of all the components described in the embodiments may be omitted, and further one or more components may be combined with and incorporated in a different embodiment(s) as appropriate.

INDUSTRIAL APPLICABILITY

According to the present invention, the brain activity can be easily estimated. Therefore, the present invention is useful in applications to brain activity visualization devices that visualize the physiological state of a subject based on the brain activity.

What is claimed is:

1. A fatigue state determination device, comprising:

a processor including a brain-function activation information provision unit that provides brain-function activation information in order to activate a human brain function of a subject;

a fatigue state determination unit that determines a fatigue state of the subject based on facial-surface change information indicative of a time-series change of facial surface data on the subject while the brain-function activation information is being provided; and a determination information generating unit that generates determination information from the facial-surface change information; and a reference information storage memory that stores, as reference information in relation to a fatigue state level, an amount of change within a predetermined range from a reference correlation value to a correlation value of determination information calculated with respect to the brain-function activation information, the reference correlation value being extracted while the subject is at rest and prior to the brain-function activation information being provided, the fatigue state determination unit calculating the correlation value of the determination information with respect to the brain-function activation information, the correlation value being extracted after the brain-function activation information is provided, and determining the fatigue state level of the subject based on the amount of change and the reference information, the amount of change being a difference between the reference correlation value and the calculated correlation value.

2. The fatigue state determination device according to claim 1, wherein the brain-function activation information provision unit provides working memory related information as the brain-function activation information.

3. The fatigue state determination device according to claim 1, wherein the processor further includes a facial-surface change information decomposition unit that decomposes the facial-surface change information into a plurality of components using singular value decomposition, principal component analysis, or independent component analysis, the determination information generating unit extracting a component related to the brain-function activation information from the plurality of components as a determination component, and generating the determination information from the determination component.

4. The fatigue state determination device according to claim 3, wherein the determination information generating unit extracts the determination component based on a value of a significance level.

5. The fatigue state determination device according to claim 1, wherein the processor further includes a facial-surface change information acquisition unit that acquires data on one or more of a paranasal sinus peripheral region and a forehead of the subject as the facial surface data.

6. The fatigue state determination device according to claim 1, further comprising:

the processor further includes a facial-surface change information acquisition unit that acquires facial skin temperature data indicative of a facial skin temperature of the subject as the facial surface data.

7. The fatigue state determination device according to claim 1, wherein the facial-surface change information acquisition unit further includes a facial-surface change information acquisition unit that acquires facial blood-circulationamount data based oil RGB data regarding a facial surface of the subject as the facial surface data.

8. The fatigue state determination device according to claim 1, wherein a determination information provision device on a network includes the reference information storage memory.

9. A fatigue state determination method, comprising:

a brain-function activation information provision step of providing brain-function activation information in order to activate a human brain function of a subject after a predetermined action of the subject;

a facial-surface change information acquisition step of acquiring facial-surface change information indicative of a time-series change in facial surface data of the subject after the predetermined action;

a fatigue state determination step of determining a fatigue state of the subject based on the facial-surface change information; and a determination information generating step of generating determination information from the facial-surface change information, an amount of change within a predetermined range from a reference correlation value to a correlation value of the determination information calculated with respect to the brain-function activation information being stored as reference information in relation to a fatigue state level, in a reference information storage unit, the reference correlation value being extracted while the subject is at rest and prior to the brain-function activation information being provided and in the fatigue state determination step, the correlation value of the determination information with respect to the brain-function activation information is calculated, the correlation value being extracted after the brain-function activation information is provided, and a fatigue state level of the subject is determined based on the amount of change and the reference information, the amount of change being a difference between the reference correlation value and the calculated correlation value.

10. The fatigue state determination method according to claim 9, further comprising:

a facial-surface change information decomposition step of decomposing the facial-surface change information into a plurality of components using singular value decomposition, principal component analysis, or independent component analysis, in the determination information generating step, a component related to the brain-function activation information being extracted as a determination component from the plurality of components, and the determination information being generated from the determination component.

11. The fatigue state determination method according to claim 10, wherein before the predetermined action, the brain-function activation information provision step, the facial-surface change information acquisition step, the facial-surface change information decomposition step, and the determination information generating step are executed to generate the reference information.

12. The fatigue state determination method according to claim 9, wherein the reference information storage memory is installed in a determination information provision device on a network, and the fatigue state determination step includes accessing the determination information provision device when determining the fatigue state level.

13. The fatigue state determination method according to claim 12, wherein the reference correlation value is calculated by providing the brain-function activation information to a person other than the subject.

14. The fatigue state determination method according to claim 9, wherein the predetermined action is an intellectual activity or a physical activity.

* * * * *